United States Patent [19]

Kaneko et al.

[11] Patent Number: 5,556,975
[45] Date of Patent: Sep. 17, 1996

[54] GRISEOLIC ACID DERIVATIVES

[75] Inventors: Masakatsu Kaneko; Yoshinobu Murofushi; Misako Kimura; Mitsuo Yamazaki; Yasuteru Iijima, all of Hiromachi, Japan

[73] Assignee: Sankyo Company, Limited, Tokyo, Japan

[21] Appl. No.: 437,634

[22] Filed: May 9, 1995

Related U.S. Application Data

[62] Division of Ser. No. 130,154, Sep. 30, 1993, Pat. No. 5,498,819, which is a continuation of Ser. No. 916,794, Jul. 17, 1992, abandoned, which is a continuation of Ser. No. 742,287, Aug. 8, 1991, abandoned, which is a continuation of Ser. No. 616,763, Nov. 19, 1990, abandoned, which is a continuation of Ser. No. 361,806, May 30, 1989, abandoned, which is a continuation of Ser. No. 157,112, Feb. 10, 1988, abandoned, which is a continuation of Ser. No. 854,418, Apr. 21, 1986, abandoned.

[30] Foreign Application Priority Data

Apr. 19, 1985 [JP] Japan .................. 60-82132
Apr. 27, 1985 [JP] Japan .................. 60-91987
Apr. 27, 1985 [JP] Japan .................. 60-91989

[51] Int. Cl.$^6$ .................. C07D 473/34; A61K 31/52
[52] U.S. Cl. .................. 544/277; 544/276
[58] Field of Search .................. 544/277, 276; 514/261, 262

[56] References Cited

U.S. PATENT DOCUMENTS

| | | |
|---|---|---|
| 4,035,370 | 7/1977 | Lorincz et al. . |
| 4,167,565 | 9/1979 | Stein et al. . |
| 4,460,765 | 7/1984 | Naito et al. . |
| 4,634,706 | 1/1987 | Kaneko et al. ........... 514/262 |
| 4,783,532 | 11/1988 | Kaneko et al. . |
| 4,803,271 | 2/1989 | Verheyden et al. . |
| 4,822,879 | 4/1989 | Nakagawa et al. . |
| 5,091,431 | 2/1992 | Tulshian et al. . |

FOREIGN PATENT DOCUMENTS 0143557 6/1985 European Pat. Off. .

OTHER PUBLICATIONS

N. D. Goldberg et al, "Biologic Regulation Through Opposing Influences of Cyclic GMP and Cyclic AMP: The Yin Yang Hypothesis", pp. 307–330, 1975, Advances in Cyclic Nucleotide Research, vol. 5.

Joseph Segal, "Opposite Regulatory Effects of cAMP and cGMP on Sugar Uptake in Rat Thymocytes", 1987, pp. E588–E594, AM, J. Physiol., 252.

Daiichi Seiyaku, "Bucladesine Sodium", vol. 10, No. 2, 1985 Drugs of the Future.

M. Hagiwara et al, "Effects of Vinpocetine on Cyclic Nucleotide Metabolism in Vascular Smooth Muscle", vol. 33, No. 3, pp. 453–457, 1984, pp. 453–457, Biochemical Pharmacology.

Tohru Ueda, Kazunobu Miuyra and Tsuguo Kasai, "Synthesis of 6–Thioguanine and 2,6–Diaminopurine Nucleosides and Nucleotides from Adenine Counterparts via a Facile Rearrangement in the Base Portion (Nucleosides and Nucleotides. XIX)".

Chem. Pharm. Bull., 26, 2122–2127 (1978).

Chemical Abstracts, vol. 106, No. 7, 1987, pp. 683–684, Abstract No. 50602a of JP 61–100593 which was published May 1986.

Primary Examiner—Nicholas Rizzo
Attorney, Agent, or Firm—Frishauf, Holtz, Goodman, Langer & Chick, P.C.

[57] ABSTRACT

A compound of the formula (I) is provided

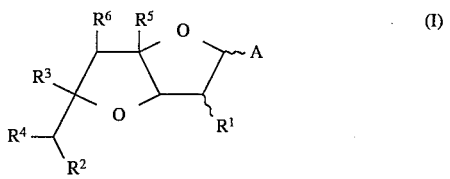

wherein A represents a group of the formula:

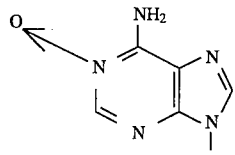

$R^1$ and $R^2$ are independently hydrogen, halogen or a group of the formula —$OR^9$; $R^3$ and $R^4$ are independently carbamoyl or carboxy; $R^5$ and $R^a$ both represent hydrogen or together represent an extra carbon-carbon bond between the carbon atoms to which they are attached; and $R^9$ is hydrogen, alkyl, alkysulfonyl, haloalkylsulfonyl, arylsulfonyl or a hydroxy-protecting group; or a pharmaceutically acceptable salt or ester thereof. The compounds are useful as inhibitors of phosphodiesterases.

6 Claims, No Drawings

GRISEOLIC ACID DERIVATIVES

This is a division of application Ser. No. 08/130,154 filed Sep. 30, 1993, now U.S. Pat. No. 5,498,819, which is a continuation of application Ser. No. 07/916,794 filed Jul. 17, 1992 (abandoned), which is a continuation of application Ser. No. 07/742,287 filed Aug. 8, 1991 (abandoned), which is a continuation of application Ser. No. 07/616,763 filed Nov. 19, 1990 (abandoned), which is a continuation of application Ser. No. 07/361,806 filed May 30, 1989 (abandoned), which is a continuation of application Ser. No. 07/157,112 filed Feb. 10, 1988 (abandoned), which is a continuation of application Ser. No. 06/854,418 filed Apr. 21, 1986 (abandoned).

BACKGROUND TO THE INVENTION

The present invention relates to a series of novel griseolic acid derivatives, and provides processes for preparing these compounds and methods and compositions using them.

Griseolic acid is a nucleoside-type compound having an adenine base and two carboxylic acid groups. It was first disclosed in, inter alia, European Patent Specification No. 29,329A, but its structure was not, at that stage, known. Its structure was first disclosed in U.S. Pat. No. 4,460,765 (assigned to the present assignees). Certain derivatives of griseolic acid were subsequently disclosed in U.S. patent application Ser. No. 664,866, now U.S. Pat. No. 4,634,706, filed on 25th Oct. 1984 by the present assignees and this also discloses the structure of griseolic acid. Other griseolic acid derivatives, specifically dihydrodesoxygriseolic acid and its salts and esters, are disclosed in U.S. Ser. No. 734,868 filed 16 May 1985; now abandoned.

In accordance with the recommendations of the International Union of Pure and Applied Chemistry (IUPAC), the compounds of the present invention are named as derivatives of griseolic acid (or of dihydrodesoxygriseolic acid), taking griseolic acid as the parent structure. The numbering system employed is shown in U.S. Ser. No. 664,866, now U.S. Pat. No. 4,634,706.

Griseolic acid and the griseolic acid derivatives of U.S. Ser. No. 664,866 and U.S. Ser. No. 734,868, now abandoned, as well the derivatives of the present invention, have the ability Lo inhibit the activity of phosphodiesterases specific to various cyclic nucleotides, for example 3',5'-cyclic adenosine monophosphate (cAMP), phosphodiesterase (PDE) or 3',5'-cyclic guanosine monophosphate (cGMP) PDE, and can thus increase the level of the cyclic nucleotide, e.g. cAMP or cGMP, in the cells of a patient treated with such a compound.

It is well known that cAMP, which is very widely distributed in animal tissues, functions as a second messenger for and mediates the effect of a large number of hormones; as a result, cAMP has a variety of very important physiological and biochemical roles. Additionally, it is known to have an effect on or participate in: division, proliferation and differentiation of cells; the systolic system, particularly miocardia; haematopoiesis; various activities of the central nervous system; immune reactions; and the liberation of insulin and histamine. Its concentration in tissues, and hence its effect upon these various functions, depends upon the balance between the enzyme which synthesizes cAMP (i.e. adenylate cyclase) and the enzyme which decomposes cAMP, cAMP PDE. An inhibitor against cAMP PDE would increase the level of cAMP in the cells and is thus expected to have a variety of therapeutic uses, for example: in the treatment of cardiovascular problems; as an antiasthmatic agent; as a smooth muscle relaxant; as a psychotropic or neurotropic agent; as an anti-inflammatory agent; in the therapy of cancer; and as a treatment for diabetes.

The activities of other cyclic nucleotides, e.g. cGMP, have, to date, been less comprehensively investigated. However, it is believed that they have a range of activities similar to, albeit not identical with, those of cAMP. Hence, inhibition of the PDE's specific to such other cyclic nucleotides will give rise to a range of therapeutic effects similar to those arising from the inhibition of cAMP PDE. As the activities of such other cyclic nucleotides are elucidated, the need will arise for inhibitors of the PDE's associated with those other nucleotides, which inhibitors show a greater specificity to one or other of the PDE's of the other nucleotides, rather than cAMP PDE; indeed, development of such inhibitors may even assist or encourage investigation of such other cyclic nucleotides.

In addition to griseolic acid and its derivatives, other compounds known to inhibit the PDE's of cAMP and cGMP include papaverine, dipyridamole and some compounds related to the constituent bases of nucleic acids, such as theophylline or M & B 22,948 [Kukovetz et al., Naunyn-Schmiedeberg's Arch. Pharmakol., 310, 129 (1979)].

We have now discovered a series of compounds which are related to griseolic acid and to dihydrodesoxygriseolic acid and which share the activity of griseolic acid and dihydrodesoxygriseolic acid. Certain of these compounds surprisingly have a greater activity against cGMP PDE than against cAMP PDE. Certain compounds of the invention, whilst retaining the desirable activity are of more value as intermediates in the preparation of other, related compounds.

BRIEF SUMMARY OF INVENTION

It is an object of the present invention to provide, as a new composition of matter, derivatives of griseolic acid and salts and esters thereof.

It is a further, and more specific, object of the invention to provide derivatives of griseolic acid which have the ability to inhibit the activity of PDE's which decompose cyclic nucleotides, e.g. cAMP PDE or cGMP PDE.

It is a further object of the invention to provide for the preparation of these compounds.

The compounds of the present invention are compounds of formula (I):

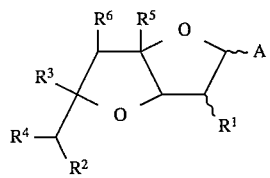

wherein:

A represents a group of formula:

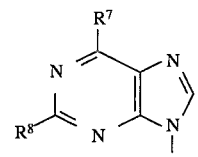

(a)

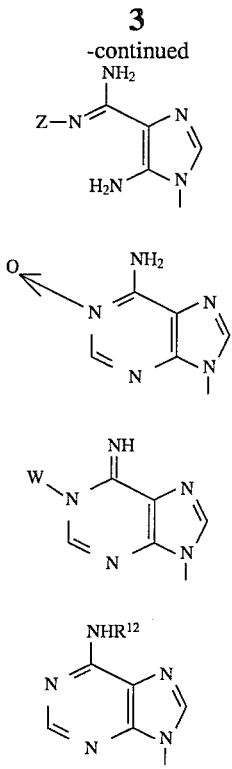

R¹ and R² are independently selected from the group consisting of hydrogen atoms, halogen atoms and groups of formula —OR⁹;

R³ and R⁴ are independently selected from the group consisting of carbamoyl groups and carboxy groups;

R⁵ and R⁶ both represent hydrogen atoms or together they represent an extra carbon-carbon bond between the carbon atoms to which they are attached:

R⁷ represents a hydrogen atom, a halogen atom or a group of formula —OR⁹, —NR¹⁰R¹¹ or —SR⁹;

R⁸ represents a halogen atom or a group of formula —OR⁹, —NR¹⁰R¹¹ or —SR⁹;

R⁹ represents a hydrogen atom, a $C_1-C_6$ alkyl group, an alkylsulfonyl group, a haloalkylsulfonyl group, an arylsulfonyl group or a hydroxy-protecting group;

R¹⁰ and R¹¹ are independently selected from the group consisting of hydrogen atoms, hydroxy groups, $C_1-C_6$ alkyl groups, $C_1-C_6$ hydroxyalkyl groups, $C_1-C_6$ aminoalkyl groups, aralkyl groups, aryl groups, $C_1-C_6$ alkoxy groups, aralkyloxy groups, amine groups, $C_1-C_{20}$ aliphatic acyl groups and aromatic acyl groups; or R¹⁰ and R¹¹ together represent a substituted methylene group, or R¹⁰ and R¹¹, together with the nitrogen atom to which they are attached, represent a heterocyclic group having 5 or 6 ring atoms, of which, in addition to the nitrogen atom shown, 0 or 1 are additional hetero-atoms selected from the group consisting of oxygen, nitrogen and sulfur atoms, said heterocyclic group being unsubstituted or having from 1 to 3 substituents selected from the group consisting of $C_1-C_4$ alkyl and $C_1-C_4$ alkoxy substituents;

R¹² represents a $C_1-C_6$ alkyl group;

Z represents a hydrogen atom, a hydroxy group or a substituted hydroxy group; and W represents an alkoxy group or an aralkoxy group;

provided that, when A represents said group of formula (e), R⁵ and R⁶ both represent hydrogen atoms;

and pharmaceutically acceptable salts and esters thereof.

The invention also provides a pharmaceutical composition comprising a phosphodiesterase inhibitor in admixture with a pharmaceutically acceptable carrier or diluent, wherein said phosphodiesterase inhibitor is selected from the group consisting of compounds of formula (I), as defined above, and pharmaceutically acceptable salts and esters thereof.

The invention further consists in a method of treating an animal, especially a mammal (e.g. human being) suffering from a disorder arising from an imbalance in phosphodiesterase levels, by administering to said animal a phosphodiesterase inhibitor, wherein said phosphodiesterase inhibitor is selected from the group consisting of compounds of formula (I), as defined above, and pharmaceutically acceptable salts and esters thereof.

The compounds of the invention may be prepared from griseolic acid or dihydrodesoxygriseolic acid by replacing the adenine moiety of said griseolic acid or dihydrodesoxygriseolic acid by another appropriate moiety of formula (A) and/or by replacing any of the groups defined above as R¹, R², R³, R⁴, R⁵, R⁶, R⁷, R⁸, R⁹, R¹⁰, R¹¹, R¹², W and Z by any other group within the definitions of said groups.

DETAILED DESCRIPTION OF INVENTION

Where reference is made herein to "aryl" groups, either as such or as part of a larger group (e.g. an arylsulfonyl, aromatic acyl, aralkyl or aralkyloxy group), this is a carbocyclic aryl group preferably having from 6 to 14, more preferably from 6 to 10, ring carbon atoms (e.g. phenyl or 1- or 2-naphthyl) which may be substituted or unsubstituted. Where the group is substituted, the substituents are preferably selected from $C_1-C_4$ alkyl groups, $C_1-C_4$ alkoxy groups, hydroxy groups, halogen atoms, nitro groups, amino groups, $C_1-C_4$ alkylamino groups, dialkylamino groups where each alkyl part is $C_1-C_4$, $C_1-C_4$ haloalkyl groups, $C_2-C_7$ alkoxycarbonyl groups, aryl groups (themselves being as defined herein, preferably phenyl groups, and substituted or unsubstituted, albeit, if substituted, preferably not with aryl groups) and cyano groups.

In the compounds of the invention, where R¹, R², R⁷ or R⁸ represents a halogen atom, this is suitably a fluorine, chlorine, bromine or iodine atom.

Where R¹, R², R⁷ or R⁸ represents a group of formula —OR⁹, R⁹ is as defined above and hence —OR⁹ represents a hydroxy, $C_1-C_6$ alkoxy, alkylsulfonyloxy, haloalkylsulfonyloxy or arylsulfonyloxy group or a protected hydroxy group.

Where the group —OR⁹ represented by R¹, R², R⁷ or R⁸ is said $C_1-C_6$ alkoxy group, this may be a straight or branched chain group and examples include the methoxy, ethoxy, propoxy, isopropoxy, butoxy, isobutoxy, sec-butoxy, t-butoxy, pentyloxy and hexyloxy groups.

Where the group —OR⁹ represented by R¹, R², R⁷ or R⁸ represents an alkylsulfonyloxy group, this is preferably a methanesulfonyloxy, ethanesulfonyloxy or propanesulfonyloxy group.

Where the group —OR⁹ represented by R¹, R², R⁷ or R⁸ represents a haloalkylsulfonyloxy group, the halogen atom may be any one of those defined above in relation to R¹, R², R⁷ and R⁸, but is preferably a fluorine atom. One or more halogen atoms may be present, up to complete perhalogenation. The perfluoroalkylsulfonyloxy groups are particularly preferred and examples of such groups include the trifluoromethanesulfonyloxy and pentafluoroethanesulfonyloxy groups.

Where the group —OR⁹ represented by R¹, R², R⁷ or R⁸ represents an arylsulfonyloxy group, the aryl part is preferably as defined above and examples of such arylsulfonyloxy groups include the benzenesulfonyloxy and p-toluenesulfonyloxy groups.

Where $R^9$ represents a hydroxy-protecting group, the nature of such a group is not critical to the invention, provided that it is "pharmaceutically acceptable" (i.e. it does not, or does not to an unacceptable extent, reduce the activity or increase the toxicity of the compound). Where the compound is to be used for non-therapeutic purposes (e.g. as an intermediate), however, this restriction does not apply. Examples of hydroxy-protecting groups which may be represented by $R^9$ include: substituted ethyl groups; aralkyl groups; alkoxycarbonyl groups; alkenyloxycarbonyl groups; aralkyloxycarbonyl groups; heterocyclic groups having 5 or 6 ring atoms, of which from 1 to 3 are hereto-atoms selected from the group consisting of oxygen, nitrogen and sulfur hereto-atoms, said heterocylic groups being unsubstituted or having from 1 to 3 substituents selected from the group consisting of halogen, $C_1$–$C_4$ alkyl and $C_1$–$C_4$ alkoxy substituents; trialkylsilyl groups in which each alkyl part is $C_1$–$C_4$; $C_1$–$C_{20}$ aliphatic acyl groups; aromatic acyl groups; alkoxymethyl groups; and hydroxy-protecting groups which are easily hydrolized in vivo.

Where the group —$OR^9$ represented by $R^1$, $R^2$, $R^7$ or $R^8$ represents said substituted ethoxy group, the ethoxy group may have one or more, preferably from 1 to 3, substituents selected from the group consisting of $C_1$–$C_4$ alkoxy groups, $C_1$–$C_4$ alkyl groups, halogen atoms, $C_1$–$C_4$ alkylselenyl and arylselenyl groups (in which the aryl part is as defined above). Examples of such groups include the 1-ethoxyethoxy, 1-methyl-1-methoxyethoxy, 1-isopropoxyethoxy, 2,2,2-trichloroethoxy and 2-phenylselenylethoxy groups.

Where the group —$OR^9$ represented by $R^1$, $R^2$, $R^7$ or $R^8$ represents an aralkyloxy group, the aryl part is preferably as defined above and the alkoxy part is preferably a $C_1$–$C_4$, more preferably $C_1$–$C_3$, alkoxy group. The aralkyloxy group may be a monoarylalkoxy group, a diarylalkoxy group or a triarylalkoxy group. Examples of such groups include the benzyloxy, phenethyloxy, p-methoxybenzyloxy, o-nitrobenzyloxy, p-nitrobenzyloxy, p-chlorobenzyloxy, p-cyanobenzyloxy, diphenylmethoxy, triphenylmethoxy, α-naphthylmethoxy, β-naphthylmethoxy, α-naphthyldiphenylmethoxy, p-methoxyphenyl-diphenylmethoxy and 3-phenylpropoxy groups.

Where the group —$OR^9$ represented by $R^1$, $R^2$, $R^7$ or $R^8$ represents an alkoxycarbonyloxy group, this is preferably a $C_2$–$C_7$, more preferably $C_2$–$C_5$, alkoxycarbonyloxy group (i.e. the alkoxy part is $C_1$–$C_6$, more preferably $C_1$–$C_4$) and the alkoxy part may be unsubstituted or may have at least one substituent selected from the group consisting of halogen atoms and tri-substituted silyl groups (e.g. as defined below in relation to the trialkylsilyl groups). Examples of such alkoxycarbonyloxy groups include the methoxycarbonyloxy, ethoxycarbonyloxy, t-butoxycarbonyloxy, 2,2,2-trichloroethoxycarbonyloxy, isobutoxycarbonyloxy and 2-trimethylsilylethoxycarbonyloxy groups.

Where the group —$OR^9$ represented by $R^1$, $R^2$, $R^7$ or R8 represents an alkenyloxycarbonyloxy group, the alkenyl part is preferably a $C_2$–$C_4$ alkenyl group and examples include the vinyloxycarbonyloxy and allyloxycarbonyloxy groups.

Where the group —$OR^9$ represented by $R^1$, $R^2$, $R^7$ or $R^8$ represents an aralkyloxycarbonyloxy group, the aralkyl part is preferably as described above in relation to the aralkyloxy groups which themselves may be represented by —$OR^9$. Examples of such groups include the benzyloxycarbonyloxy, p-methoxybenzyloxycarbonyloxy, 3,4-dimethoxybenzyloxycarbonyloxy, o-nitrobenzyloxycarbonyloxy and p-nitrobenzyloxycarbonyloxy groups.

Where the group —$OR^9$ represented by $R^1$, $R^2$, $R^7$ or $R^8$ represents an alkoxymethoxy group, this may be a mono-alkoxymethoxy or di-alkoxymethoxy group and the alkoxy part is preferably a $C_1$–$C_6$, more preferably $C_1$–$C_4$, alkoxy group which may be unsubstituted or have at least one substituent selected from the group consisting of $C_1$–$C_4$ alkoxy groups and halogen atoms. Examples of such alkoxymethoxy groups include the methoxymethoxy, ethoxymethoxy, propoxymethoxy, isopropoxymethoxy, butoxymethoxy, t-butoxymethoxy, 2-methoxyethoxymethoxy, 2,2,2-trichloroethoxymethoxy and bis(2-chloroethoxy)methoxy groups.

Where the group —$OR^9$ represented by $R^1$, $R^2$, $R^7$ or R8 represents a protected hydroxy group which is easily hydrolized in vivo, the group may fall within a number of different classes, including some classes which overlap with those protected hydroxy groups described above. In general, preferred such protected hydroxy groups include: the aralkyloxycarbonyloxy groups, particularly as defined above; and the acyloxy-substituted alkoxycarbonyloxy, preferably methoxycarbonyloxy, groups, such as the pivaloyloxymethoxycarbonyloxy group.

Where the group —$OR^9$ represented by $R^1$, $R^2$, $R^7$ or $R^8$ represents said heterocyclic-oxy group, this is preferably such a group containing a single oxygen hereto-atom and is more preferably a pyranyloxy, dihydropyranyloxy, tetrahydropyranyloxy or tetrahydrofuryloxy group, or their thiopyran or thiofuran analogs, which may be unsubstituted or have from 1 to 3 substituents selected from the group consisting of $C_1$–$C_4$ alkyl, $C_1$–$C_4$ alkoxy and halogen substituents. Preferred examples of such groups are the tetrahydropyran-2-yloxy, 3-bromotetrahydropyran-2-yloxy, tetrahydrothiopyran-2-yloxy, 4-methoxytetrahydrothiopyran-4-yloxy, tetrahydrofuran-2-yloxy, tetrahydrothiofuran-2-yloxy and 4-methoxytetrahydropyran-4-yloxy groups.

Where the group —$OR^9$ represented by $R^1$, $R^2$, $R^7$ or $R^8$ represents a trialkylsilyloxy group, the three alkyl groups may be the same or different and may be straight or branched chain groups containing from 1 to 4 carbon atoms. Examples of such groups are the trimethylsilyloxy, triethylsilyloxy, diisopropylmethylsilyloxy, di-t-butylmethylsilyloxy, triisopropylsilyloxy, dimethylisopropylsilyloxy and t-butyldimethylsilyloxy groups. Where the group -$OR^9$ represented by $R^1$, $R^2$, $R^7$ or $R^8$ represents an aliphatic acyloxy group, this is an aliphatic carboxylic acyloxy group, which may be saturated or unsaturated (the terms "saturated" and "unsaturated" referring, in this context, to carbon-carbon bonds within said groups) and there is no particular limitation on the chain length of the acyloxy group, both short and long chain acyloxy groups being useful in the present invention. Examples of such acyloxy groups include the formyloxy, acetoxy, chloroacetoxy, dichloroacetoxy, trichloroacetoxy, trifluoroacetoxy, methoxyacetoxy, propionyloxy, butyryloxy, (E)-2-methyl-2-butenoyloxy, isobutyryloxy, valeryloxy, isovaleryloxy, pivaloyloxy, octanoyloxy, lauroyloxy, palmitoyloxy and stearoyloxy groups.

Where the group —$OR^9$ represented by $R^1$, $R^2$, $R^7$ or $R^8$ represents an aromatic acyloxy group, this is an aromatic carboxylic acyloxy group and is preferably an arylcarbonyloxy group in which the aryl part is as defined above. Preferred such aromatic acyloxy groups include the benzoyloxy, p-toluoyloxy, p-anisoyloxy, p-chlorobenzoyloxy, p-nitrobenzoyloxy, o-(dibromomethyl)benzoyloxy, o-(methoxycarbonyl)benzoyloxy, p-phenylbenzoyloxy, 2,4,6- trimethylbenzoyloxy, o-nitrobenzoyloxy and α-naphthoyloxy groups.

Where $R^7$ or $R^8$ represents a group of formula —$SR^9$ these may be the thio analogs of the optionally substituted hydroxy groups of formula —$OR^9$ mentioned above and examples of such groups are the thio analogs of those groups of formula —$OR^9$ exemplified above. Preferred groups of formula —$SR^9$ which may be represented by $R^7$ and $R^8$ include: the mercapto group; $C_1$–$C_6$ alkylthio groups, particularly the methylthio, ethylthio, propylthio, isopropylthio, butylthio, isobutylthio, sec-butylthio, t-butylthio, pentylthio and hexylthio groups; aralkylthio groups, particularly the benzylthio, p-chlorobenzylthio, p-methoxybenzylthio, p-nitrobenzylthio, phenethylthio, and α- and β-naphthylmethylthio groups; aliphatic acylthio groups, such as the acetylthio, propionylthio, butyrylthio and isobutyrylthio groups; and aromatic acylthio groups, such as the benzoylthio, p-toluoylthio, p-anisoylthio, p-chlorobenzoylthio and α- and β-naphthoylthio groups.

Where $R^7$ or $R^8$ represents an amino or substituted amino group of formula —$NR^{10}R^{11}$, $R^{10}$ and $R^{11}$ may be the same or different and each represents a hydrogen atom, a hydroxy group, a $C_1$–$C_6$ alkyl group, a $C_1$–$C_6$ hydroxyalkyl group, a $C_1$–$C_6$ aminoalkyl group, an aralkyl group, an aryl group, a $C_1$–$C_6$ alkoxy group, an aralkyloxy group, an amino group, a $C_1$–$C_{20}$ aliphatic acyl group or an aromatic acyl group; or $R^{10}$ and $R^{11}$ together may form a cyclic amino group; or $R^{10}$ and $R^{11}$ may together represent a substituted methylene group. Except where hereafter otherwise specified, it is preferred that $R^{11}$ represents hydrogen and $R^{10}$ represents hydrogen or one of the above identified groups.

Where $R^{10}$ and/or $R^{11}$ represents an alkyl group, the group represented by —$NR^{10}R^{11}$ may be a mono- or dialkylamino group, particularly the methylamino, dimethylamino, ethylamino, diethylamino, propylamino, dipropylamino, butylamino, isobutylamino, sec-butylamino, t-butylamino, pentylamino and hexylamino groups. Where $R^{10}$ represents a hydroxyalkyl group, preferred examples of groups represented by —$NR^{10}R^{11}$ are the 2-hydroxyethylamino and 3-hydroxypropylamino groups. Where $R^{10}$ represents an aminoalkyl group, preferred examples of the groups represented by —$NR^{10}R^{11}$ are the 2-aminoethylamino and 3-aminopropylamino groups.

Where $R^{10}$ represents an aralkyl group, preferred examples of groups represented by —$NR^{10}R^{11}$ are the benzylamino, p-methylbenzylamino, p-methoxybenzylamino, p-chlorobenzylamino, phenethylamino, α-naphthylmethylamino and β-naphthylmethylamino groups. Where $R^{10}$ represents an aryl group, preferred examples of groups represented by —$NR^{10}R^{11}$ are the anilino, p-toluidino, p-anisidino, p-chloroanilino, α-naphthylamino and β-naphthylamino groups. Where $R^{10}$ represents a hydroxy group, the group —$NR^{10}R^{11}$ is preferably the hydroxyamino group.

Where $R^{10}$ represents an alkoxy group, preferred examples of groups represented by —$NR^{10}R^{11}$ are the methoxyamino, ethoxyamino and propoxyamino groups.

Where $R^{10}$ represents an aralkyloxy group, preferred examples of groups represented by —$NR^{10}R^{11}$ are the benzyloxyamino, p-methylbenzyloxyamino, p-methoxybenzyloxyamino, p-chlorobenzyloxyamino and p-nitrobenzyloxyamino groups.

Where $R^{10}$ represents an amino group, the group represented by —$NR^{10}R^{11}$ is preferably the hydrazino group.

Where $R^{10}$ and/or $R^{11}$ represents an aliphatic acyl group, preferred examples of groups represented by —$NR^{10}R^{11}$ are the acetamido, propionylamido, dipropionylamido, butyrylamido, dibutyrylamido, isobutyrylamido, valerylamido, isovalerylamido, octanoylamido, lauroylamido, palmitoylamido and stearoylamido groups. Where $R^{10}$ and/or $R^{11}$ represents an aromatic acyl group, preferred examples of groups represented by —$NR^{10}R^{11}$ are the benzamido, dibenzamido, p-toluoylamido, di-p-toluoylamido, p-anisoylamido, di-p-anisoylamido, p-chlorobenzamido, di-p-chlorobenzamido and p-nitrobenzamido groups.

Where $R^{10}$ and $R^{11}$ together represent a substituted methylene group, the substituent or substituents may be any group capable of stabilizing a methyleneamino group. Examples include 1 or 2 aryl groups (the aryl groups preferably being as defined above) and amino groups of formula —$NR^{10a}R^{11a}$ where $R^{10a}$ and $R^{11a}$ are any of the hydrogen atoms, alkyl groups, aralkyl groups and aryl groups defined above for $R^{10}$ and $R^{11}$ preferably the alkyl groups. Preferred examples of such substituted methyleneamino groups which may be represented by —$NR^{10}R^{11}$ are the N,N-dimethylaminomethyleneamino, benzylideneamino, p-methoxybenzylideneamino, p-nitrobenzylideneamino, salicylideneamino, 5-chlorosalicylideneamino, diphenylmethyleneamino and (5-chloro-2-hydroxyphenyl)phenylmethyleneamino groups.

Where $R^{10}$ and $R^{11}$ together with the nitrogen atom to which they are attached, represent a cyclic amino group, this may optionally contain at least one other hereto-atom selected from oxygen, nitrogen and sulfur atoms and preferably contains either no other hereto-atom or one other hetero-atom selected from oxygen and nitrogen atoms. Preferred such cyclic amino groups which may be represented by —$NR^{10}R^{11}$ are the 1-pyrrolidinyl, 1-piperazinyl, morpholino and 4-methyl-1-piperazinyl groups.

Where A represents a group of formula (e), $R^{12}$ represents a $C_1$–$C_6$ alkyl group, which may be a straight or branched chain group, and examples include the methyl, ethyl, propyl, isopropyl, butyl, isobutyl, sec-butyl, t-butyl, pentyl, isopentyl, sec-pentyl, neopentyl, t-pentyl, hexyl and isohexyl groups, of which the $C_1$–$C_4$ alkyl groups are preferred.

Where Z represents an optionally substituted hydroxy group, this is preferably a group of formula —$OR^9$, more preferably an alkoxy group or an aralkyloxy group, examples of which are as given in relation to the group —$OR^9$.

Where W represents an alkoxy group or aralkyloxy group, examples of such groups are those given in relation to the group —$OR^9$.

The compounds of formula (I) contain two carboxy groups and can thus form mono- or di-salts and mono- or di-esters. In the case of the di-salts and di-esters, the cationic moieties of the salts or the alcoholic moieties of the esters can be the same or different. In practice, however, it is most easy to prepare di-salts or di-esters, particularly those in which the two cationic moieties or the two alcoholic moieties are the same.

There is no particular limitation upon the nature of the alcoholic moiety of the ester, provided that, where it is intended for therapeutic use, it is "pharmaceutically acceptable", which, as is well-known to those skilled in the art, means that it does not, or does not to an unacceptable extent, reduce the activity of the compound or increase its toxicity and all esters conventionally formed for compounds of this type may be formed with the compounds of the invention. Where the esters are intended for non-therapeutic uses, however, (e.g. as intermediates) even this restriction does not apply. Examples of such esters include: $C_1$–$C_6$ alkyl esters, particularly the methyl, ethyl, propyl, isopropyl, butyl, isobutyl and t-butyl esters; aralkyl esters, particularly the benzyl, p-nitrobenzyl, o-nitrobenzyl, triphenylmethyl, bis(o-nitrophenyl)-methyl, 9-anthrylmethyl, 2.4,6-trimethylbenzyl, p-bromobenzyl, p-methoxybenzyl, piperonyl and benzhydryl esters; $C_1$–$C_6$ haloalkyl esters which may have 1 or more halogen (e.g. chlorine, bromine, fluorine or iodine) atoms up to complete perhalogenation, e.g. the 2,2,2-trichloroethyl, 2-chloroethyl, 2-bromoethyl. 2-fluoroethyl, 2-iodoethyl and 2,2-dibromoethyl esters; alkoxymethyl esters where the alkoxy part is preferably $C_1$–$C_4$, e.g. the methoxymethyl, ethoxymethyl, propoxymethyl, isopropoxymethyl and butoxymethyl esters; aliphatic acyloxyalkyl esters (particularly the acyloxymethyl and acyloxyethyl esters), such as the acetoxymethyl, propionyloxymethyl, butyryloxymethyl, pivaloyloxymethyl, 1-acetoxyethyl, 1-propionyloxyethyl; 1-butyryloxyethyl and 1-pivaloyloxyethyl esters; ($C_1$–$C_4$ alkyl)oxycarbonyloxyethyl esters, such as the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl and 1-isobutoxycarbonyloxyethyl esters; heterocyclic esters, such as the phthalidyl esters; heterocyclyl-methyl esters (in which the heterocyclic group is preferably as defined for $R^9$) for example the (5-methyl-2-oxo-1,3-dioxolen-4-yl)methyl esters; and esters which are easily hydrolized in vivo, a class which includes some of the esters of classes mentioned above [e.g. the aliphatic acyloxyalkyl esters, the lower alkoxycarbonyloxyethyl esters, the (5-methyl-2-oxo-1,3-dioxolen-4-yl)methyl esters and the phthalidyl esters].

There is no particular limitation on the nature of the cations employed to form salts of the compounds of the invention, provided that, where they are intended for therapeutic use, they are pharmaceutically acceptable. Again, if they are to be used for non-therapeutic purposes (e.g. as intermediates), even this restriction does not apply. Preferred salts include salts with alkali metals (such as sodium or potassium) or with alkaline earth metals (such as calcium). Where one or both of $R^7$ and $R^8$ represents an amino group, or where A represents said group of formula (b), (c), (d) or (e), the compounds of the invention will also form acid addition salts. The nature of the acid employed to form such salts is not critical, provided that, where they are intended for therapeutic use, they are pharmaceutically acceptable. Again, if they are to be used for non-therapeutic purposes (e.g. as intermediates), even this restriction does not apply. Examples of such acids include: inorganic acids, such as hydrochloric acid, sulfuric acid and phosphoric acid; organic carboxylic acids, such as acetic acid, oxalic acid, maleic acid, succinic acid, citric acid, tartaric acid, fumaric acid, lauric acid, stearic acid and palmitic acid; and such organic sulfonic acids as methanesulfonic acid, benzenesulfonic acid and p-toluenesulfonic acid.

The compounds of the present invention have a number of asymmetric carbon atoms in their molecules and can therefore, exist in the form of various stereoisomers. The present invention includes both the individual isolated isomers as well as mixtures of these isomers. Griseolic acid, being a natural product, is a single isomer, in which both the 2' and 7' carbon atoms are in the R configuration; compounds prepared from griseolic acid may retain the same configuration or may have the inverted configuration at one or more of the asymmetric carbon atoms. For example, when $R^1$ represents a group or atom other than hydrogen, the configuration of the compounds at the 2'-position may be α or β. When $R^2$ represents a group or atom other than hydrogen, the configuration at the 7'-position may be RS, R or S.

Preferred classes of compound of the present invention are:

1. Compounds of formula (I), in which:
$R^1$ and $R^2$ are independently selected from the group consisting of hydrogen atoms, halogen atoms and groups of formula $-OR^{9a}$.
 where $R^{9a}$ represents a hydrogen atom, an alkoxycarbonyl group, an alkenyloxycarbonyl group, an aralkyloxycarbonyl group, a $C_1$–$C_{20}$ aliphatic carboxylic acyl group or a carbocyclic aromatic carboxylic acyl group,
and their salts and esters.
2. Compounds as defined in 1 above, in which:
$R^3$ and $R^4$ are independently selected from the group consisting of carboxy groups, carbamoyl groups, $C_2$–$C_5$ alkoxycarbonyl groups, (5-methyl-2-oxo-1,3-dioxolan-4-yl)methoxycarbonyl groups, phthalidyloxycarbonyl groups and $C_2$–$C_5$ alkoxycarbonyl groups having at least one substituent selected from the group consisting of aryl groups, $C_1$–$C_6$ aliphatic carboxylic acyloxy groups and $C_1$–$C_4$ alkoxycarbonyloxy groups.
3. Compounds as defined in 1 or 2 above, in which:
A represents a group of formula (a), defined above, in which:
  $R^7$ represents a hydrogen atom, a halogen atom, a group of formula $-OR^a$ where
    $R^a$ represents a hydrogen atom, a $C_1$–$C_6$ alkyl group or a $C_7$–$C_{11}$ aralkyl group,
  a group of formula $-SR^b$ where
    $R^b$ represents a hydrogen atom, a $C_1$–$C_6$ alkyl group, a $C_7$–$C_{11}$ aralkyl group, a $C_2$–$C_4$ aliphatic carboxylic acyl group or a $C_7$–$C_{11}$ arylcarbonyl group,
  or a group of formula $-NR^{10b}R^{11b}$ where
    $R^{10b}$ and $R^{11b}$ are independently selected from the group consisting of hydrogen atoms, hydroxy groups, $C_1$–$C_6$ alkyl groups, $C_1$–$C_6$ hydroxyalkyl groups, $C_1$–$C_6$ aminoalkyl groups, aralkyl groups, aryl groups, $C_1$–$C_6$ alkoxy groups, aralkyloxy groups, amino groups, $C_1$–$C_{20}$ aliphatic acyl groups and aromatic acyl groups, or
    $R^{10b}$ and $R^{11b}$ together form a heterocyclic group as defined for $R^{10}$ and $R^{11}$, or $R^{10b}$ and $R^{11b}$ together form a substituted methylene group; and
$R^8$ represents a halogen atom, a group of formula $-OR^a$ where
  $R^a$ represents a hydrogen atom, a $C_1$–$C_6$ alkyl group or a $C_7$–$C_{11}$ aralkyl group,
a group of formula $-SR^b$ where
  $R^b$ represents a hydrogen atom, a $C_1$–$C_6$ alkyl group, a $C_7$–$C_{11}$ aralkyl group, a $C_2$–$C_4$ aliphatic carboxylic acyl group or a $C_7$–$C_{11}$ arylcarbonyl group,
or a group of formula $-NR^{10b}R^{11b}$ where
  $R^{10b}$ and $R^{11b}$ are independently selected from the group consisting of hydrogen atoms, hydroxy groups, $C_1$–$C_6$ alkyl groups, $C_1$–$C_6$ hydroxyalkyl groups, $C_1$–$C_6$ aminoalkyl groups, aralkyl groups, aryl groups, $C_1$–$C_6$ alkoxy groups, aralkyloxy groups, amino groups, $C_1$–$C_{20}$ aliphatic acyl groups and aromatic acyl groups, or
  $R^{10b}$ and $R^{11b}$ together form a heterocyclic group as defined for $R^{10}$ and $R^{11}$, or $R^{10b}$ and $R^{11b}$ together form a substituted methylene group.
4. Compounds as defined in 1 or 2 above, in which:
A represents a group of formula (b), defined above, in which:
  Z represents a hydrogen atom, a $C_1$–$C_4$ alkoxy group or an aralkyloxy group in which the alkyl part is $C_1$–$C_3$ and the aryl part is a $C_6$–$C_{10}$ carbocyclic aryl group which is unsubstituted or has from 1 to 3 substituents selected from the group consisting of nitro groups, halogen atoms, $C_1$–$C_4$ alkyl groups, $C_1$–$C_4$ alkoxy groups, amino groups, hydroxy groups and cyano groups.

5. Compounds as defined in 1 or 2 above, where A represents a group of formula (c), defined above.

6. Compounds as defined in 1 or 2 above, where A represents a group of formula (d), defined above, in which:

W represents a $C_1$–$C_4$ alkoxy group or an aralkyloxy group in which the alkyl part is $C_1$–$C_3$ and the aryl part is a $C_6$–$C_{10}$ carbocyclic aryl group which is unsubstituted or has from 1 to 3 substituents selected from the group consisting of nitro groups, halogen atoms, $C_1$–$C_4$ alkyl groups, $C_1$–$C_4$ alkoxy groups, amino groups, hydroxy groups and cyano groups.

7. Compounds of formula (I), in which:

$R^1$ and R2 are independently selected from the group consisting of hydrogen atoms, halogen atoms, hydroxy groups, unsubstituted $C_1$–$C_4$ aliphatic acyloxy groups and aromatic acyloxy groups in which the aromatic part is a $C_6$–$C_{10}$ carbocyclic aryl group which is unsubstituted or has from 1 to 3 substituents selected from the group consisting of nitro groups, halogen atoms, $C_1$–$C_4$ alkyl groups, $C_1$–$C_4$ alkoxy groups, amino groups, hydroxy groups and cyano groups.

8. Compounds as defined in 7 above, in which:

$R^3$ represents a carboxy group, a $C_2$–$C_5$ alkoxycarbonyl group, a (5-methyl-2-oxo-1,3-dioxolen-4-yl)methoxycarbonyl group, a phthalidyloxycarbonyl group or a $C_2$–$C_5$ alkoxycarbonyl group having 1 or 2 substituents selected from the group consisting of $C_2$–$C_5$ alkanoyloxy groups, $C_1$–$C_4$ alkoxycarbonyloxy groups and $C_6$–$C_{10}$ carbocyclic aryl groups which are unsubstituted or have from 1 to 3 substituents selected from the group consisting of nitro groups, halogen atoms, $C_1$–$C_4$ alkyl groups, $C_1$–$C_4$ alkoxy groups, amino groups, hydroxy groups and cyano groups; and $R^4$ represents a carbamoyl group, or any one of the groups defined above for $R^3$.

9. Compounds as defined in 7 or 8 above, in which:

A represents a group of formula (a), defined above, in which:

$R^7$ represents a hydrogen atom, a halogen atom, a group of formula —$OR^c$ where $R^c$ represents a hydrogen atom, a $C_1$–$C_4$ alkyl group or a $C_7$ or $C_8$ aralkyl group, a group of formula —$SR^d$ where $R^d$ represents a hydrogen atom, a $C_1$–$C_4$ alkyl group, a $C_7$ or $C_8$ aralkyl group or a $C_2$–$C_4$ aliphatic carboxylic acyl group, a group of formula —NR10c$R^{11c}$ where $R^{10}$c and $R^{11c}$ are independently selected from the group consisting of hydrogen atoms, hydroxy groups, $C_1$–$C_6$ alkyl groups, aralkyl groups, aryl groups, $C_1$–$C_6$ alkoxy groups, aralkyloxy groups, $C_1$–C20 aliphatic carboxylic acyl groups and aromatic carboxylic acyl groups, an (N,N-dimethylamino)methyleneamino group, a benzylideneamino group, a p-methoxybenzylideneamino group, a p-nitrobenzylideneamino group, a salicylideneamino group, a 5-chlorosalicylideneamino group, a diphenylmethyleneamino group or a (5-chloro-2-hydroxyphenyl)phenylmethyleneamino group; and $R^8$ represents a halogen atom, a group of formula —$OR^c$ where $R^c$ represents a hydrogen atom, a $C_1$–$C_4$ alkyl group or a $C_7$ or $C_8$ aralkyl group, a group of formula —$SR^d$ where $R^d$ represents a hydrogen atom, a $C_1$–$C_4$ alkyl group, a $C_7$ or $C_8$ aralkyl group or a $C_2$–$C_4$ aliphatic carboxylic acyl group, a group of formula —$NR^{10c}R^{11c}$ where $R^{10c}$ and $R^{11c}$ are independently selected from the group consisting of hydrogen atoms, hydroxy groups, $C_1$–$C_6$ alkyl groups, aralkyl groups, aryl groups, $C_1$–$C_6$ alkoxy groups, aralkyloxy groups, $C_1$–$C_{20}$ aliphatic carboxylic acyl groups and aromatic carboxylic acyl groups, an (N,N-dimethylamino)methyleneamino group, a benzylideneamino group, a p-methoxybenzylideneamino group, a p-nitrobenzylideneamino group, a salicylideneamino group, a 5-chlorosalicylideneamino group, a diphenylmethyleneamino group or a (5-chloro-2-hydroxyphenyl)phenylmethyleneamino group.

10. Compounds as defined in 7 or 8 above, in which:

A represents a group of formula (b) defined above, in which:

Z represents a hydrogen atom, a $C_1$–$C_4$ alkoxy group or a benzyloxy group which is unsubstituted or has from 1 to 3 ring substituents selected from the group consisting of nitro groups, halogen atoms, $C_1$–$C_4$ alkyl groups, $C_1$–$C_4$ alkoxy group, amino groups, hydroxy groups and cyano groups.

11. Compounds as defined in 7 or 8 above, in which A represents a group of formula (c) defined above.

12. Compounds as defined in 7 or 8 above, in which:

A represents a group of formula (d), defined above, in which:

W represents a $C_1$–$C_4$ alkoxy group or a benzyloxy group which is unsubstituted or has from 1 to 3 ring substituents selected from the group consisting of nitro groups, halogen atoms, $C_1$–$C_4$ alkyl groups, $C_1$–$C_4$ alkoxy groups, hydroxy groups and cyano groups.

13. Compounds of formula (I), in which:

$R^1$ and $R^2$ are independently selected from the group consisting of hydrogen atoms, halogen atoms and hydroxy groups:

$R^5$ and $R^6$ both represent hydrogen atoms; and

A represents a group of formula (e), defined above, where $R^{12}$ represents a $C_1$–$C_6$ alkyl group.

14. Compounds as defined in 13 above, where:

$R^3$ and $R^4$ are as defined in 8 above.

Examples of compounds of the present invention are shown in the following formulae (I-1) to (I-8), in which the substituents are as defined in Tables 1–8, respectively. Where appropriate, the compounds of the invention are hereinafter referred to by the numbers assigned to them in those Tables.

In the Tables, the abbreviations used have the following meanings:

| | |
|---|---|
| Ac | acetyl |
| Boz | benzoyl |
| Bu | butyl |
| Bz | benzyl |
| Bzh | benzhydryl |
| Dox | (5-methyl-2-oxo-1,3-dioxolen-4-yl)methyl |
| Et | ethyl |
| Hx | hexyl |
| Me | methyl |
| Piv | pivaloyl |
| Pn | pentyl |

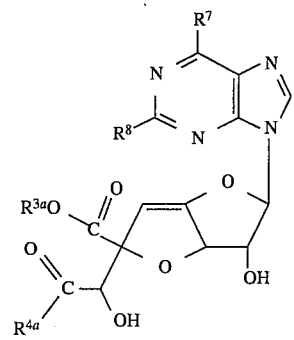 (I-1)

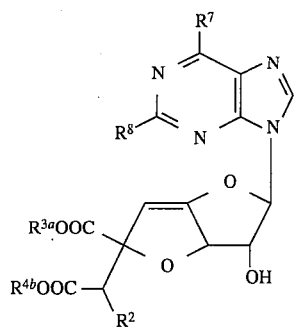 (I-2)

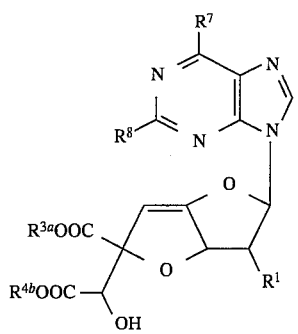 (I-3)

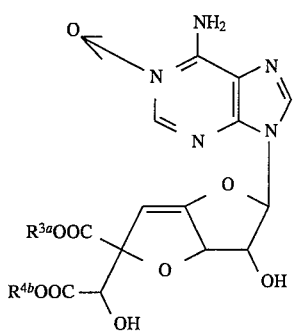 (I-4)

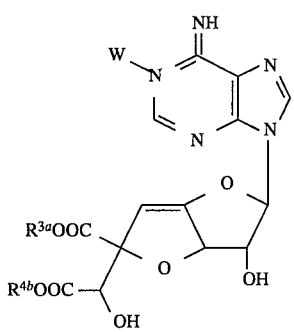 (I-5)

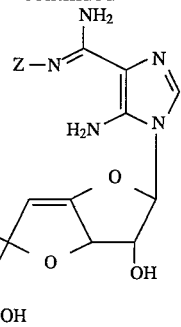 (I-6)

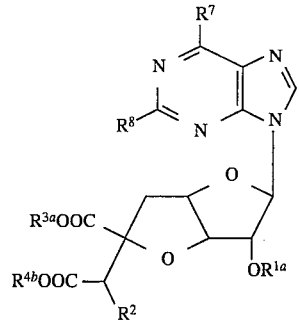 (I-7)

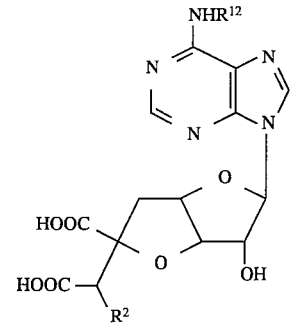 (I-8)

TABLE 1

| Cpd No. | $R^7$ | $R^8$ | $R^{3a}$ | $R^{4a}$ |
|---|---|---|---|---|
| 1 | OH | OH | H | OH |
| 2 | OH | OH | Me | OMe |
| 3 | OH | OH | H | $NH_2$ |
| 4 | OH | OH | PivOMe— | PivOMeO— |
| 5 | OH | $NH_2$ | H | OH |
| 6 | OH | $NH_2$ | Me | OMe |
| 7 | OH | $NH_2$ | H | OMe |
| 8 | OH | $NH_2$ | H | $NH_2$ |
| 9 | OH | SH | H | OH |
| 10 | OH | F | H | OH |
| 11 | OH | Cl | H | OH |
| 12 | OH | Br | Dox | Dox-O— |
| 13 | OH | I | H | OH |
| 14 | $NH_2$ | OH | H | OH |
| 15 | $NH_2$ | OH | Me | OMe |
| 16 | $NH_2$ | OH | Bzh | OBzh |
| 17 | $NH_2$ | OH | PivOMe— | PivOMeO— |
| 18 | $NH_2$ | $NH_2$ | H | OH |
| 19 | $NH_2$ | $NH_2$ | Me | OMe |
| 20 | $NH_2$ | $NH_2$ | Bzh | OBzh |
| 21 | OH | $NH_2$ | PivOMe— | PivOMeO— |
| 22 | NHOMe | $NH_2$ | H | OH |
| 23 | NHOMe | $NH_2$ | Me | OMe |
| 24 | NHOMe | $NH_2$ | Bzh | OBzh |
| 25 | NHOBz | $NH_2$ | H | OH |
| 26 | NHOBz | $NH_2$ | Me | OMe |
| 27 | NHOBz | $NH_2$ | Bzh | OBzh |
| 28 | NHOH | $NH_2$ | H | OH |

TABLE 1-continued

| Cpd No. | R⁷ | R⁸ | R³ᵃ | R⁴ᵃ |
|---|---|---|---|---|
| 29 | NHOH | NH₂ | Me | OMe |
| 30 | NHOH | NH₂ | Bzh | OBzh |
| 31 | BzhNH | NH₂ | H | OH |
| 32 | BzhNH | NH₂ | Me | OMe |
| 33 | BzhNH | NH₂ | Bzh | OBzh |
| 34 | NH₂ | F | H | OH |
| 35 | NH₂ | F | PivOMe— | PivOMeO— |
| 36 | NH₂ | I | H | OH |
| 37 | NH₂ | Cl | H | OH |
| 38 | NH₂ | Cl | Me | OMe |
| 39 | NH₂ | Cl | Bzh | OBzh |
| 40 | NH₂ | Cl | PivOMe— | PivOMeO— |
| 41 | NH₂ | Br | H | OH |
| 42 | NH₂ | Br | Me | OMe |
| 43 | NH₂ | Br | Bzh | OBzh |
| 44 | NH₂ | SH | H | OH |
| 45 | NH₂ | SH | Me | OMe |
| 46 | NH₂ | SH | Bzh | OBzh |
| 47 | NH₂ | SMe | H | OH |
| 48 | NH₂ | SBz | H | OH |
| 49 | SH | OH | H | OH |
| 50 | SMe | OH | H | OH |
| 51 | SBz | OH | H | OH |
| 52 | SH | NH₂ | H | OH |
| 53 | SH | NHOMe | H | OH |
| 54 | SH | NHOBz | H | OH |
| 55 | SH | NHOH | H | OH |
| 56 | SH | BzhNH | H | OH |
| 57 | F | F | H | OH |
| 58 | F | Cl | H | OH |
| 59 | F | Br | H | OH |
| 60 | F | I | H | OH |
| 61 | Cl | F | H | OH |
| 62 | Cl | Cl | H | OH |
| 63 | Cl | Br | H | OH |
| 64 | Cl | I | H | OH |
| 65 | Br | F | H | OH |
| 66 | Br | Cl | H | OH |
| 67 | Br | Br | H | OH |
| 68 | Br | I | H | OH |
| 69 | I | F | H | OH |
| 70 | I | Cl | H | OH |
| 71 | I | Br | H | OH |
| 72 | I | I | H | OH |
| 73 | F | OH | H | OH |
| 74 | Cl | OH | H | OH |
| 75 | Br | OH | H | OH |
| 76 | I | OH | H | OH |
| 77 | F | NH₂ | H | OH |
| 78 | Cl | NH₂ | H | OH |
| 79 | Br | NH₂ | H | OH |
| 80 | I | NH₂ | H | OH |
| 81 | F | SH | H | OH |
| 82 | Cl | SH | H | OH |
| 83 | Br | SH | H | OH |
| 84 | I | SH | H | OH |

TABLE 2

| Cpd No. | R⁷ | R⁸ | R² | R³ᵃ | R⁴ᵇ |
|---|---|---|---|---|---|
| 85 | OH | OH | H | H | H |
| 86 | OH | NH₂ | Cl | H | H |
| 87 | OH | NH₂ | H | H | H |
| 88 | OH | SH | Br | H | H |
| 89 | OH | F | H | H | H |
| 90 | OH | Cl | Cl | H | H |
| 91 | OH | Br | Br | H | H |
| 92 | OH | I | H | H | H |
| 93 | NH₂ | OH | Cl | H | H |
| 94 | NH₂ | OH | H | H | H |
| 95 | NH₂ | NH₂ | Br | H | H |
| 96 | NH₂ | NH₂ | H | H | H |
| 97 | NHOMe | NH₂ | H | H | H |
| 98 | NHOBz | NH₂ | Cl | H | H |
| 99 | NHOBz | NH₂ | H | H | H |
| 100 | NHOH | NH₂ | Br | H | H |
| 101 | BzhNH | NH₂ | H | H | H |
| 102 | NH₂ | F | Cl | H | H |
| 103 | NH₂ | I | Br | H | H |
| 104 | NH₂ | Cl | H | H | H |
| 105 | NH₂ | Br | Cl | H | H |
| 106 | NH₂ | SH | Br | H | H |
| 107 | SH | OH | H | H | H |
| 108 | SH | NH₂ | Cl | H | H |
| 109 | SH | NHOMe | Br | H | H |
| 110 | SH | NHOBz | H | H | H |
| 111 | SH | NHOH | Cl | H | H |
| 112 | SH | BzhNH | Br | H | H |
| 113 | F | F | H | H | H |
| 114 | F | Cl | Cl | H | H |
| 115 | F | Br | Br | H | H |
| 116 | F | I | H | H | H |
| 117 | Cl | F | Br | H | H |
| 118 | Cl | Cl | H | H | H |
| 119 | Cl | Cl | H | H | H |
| 120 | Cl | I | Cl | H | H |
| 121 | Br | F | Br | H | H |
| 122 | Br | Cl | H | H | H |
| 123 | Br | Br | Cl | H | H |
| 124 | Br | I | Br | H | H |
| 125 | I | F | H | H | H |
| 126 | I | Cl | Cl | H | H |
| 127 | I | Br | Br | H | H |
| 128 | I | I | H | H | H |

TABLE 3

| Cpd No. | R⁷ | R⁸ | R¹ | R³ᵃ | R⁴ᵇ |
|---|---|---|---|---|---|
| 129 | OH | OH | H | H | H |
| 130 | OH | NH₂ | Cl | H | H |
| 131 | OH | NH₂ | H | H | H |
| 132 | OH | SH | Br | H | H |
| 133 | OH | F | H | H | H |
| 134 | OH | Cl | Cl | H | H |
| 135 | OH | Br | Br | H | H |
| 136 | OH | I | H | H | H |
| 137 | NH₂ | OH | Cl | H | H |
| 138 | NH₂ | OH | H | H | H |
| 139 | NH₂ | NH₂ | Cl | H | H |
| 140 | NH₂ | NH₂ | H | H | H |
| 141 | NHOMe | NH₂ | H | H | H |
| 142 | NHOBz | NH₂ | H | H | H |
| 143 | NHOH | NH₂ | Br | H | H |
| 144 | BzhNH | NH₂ | H | H | H |
| 145 | NH₂ | F | Cl | H | H |
| 146 | NH₂ | I | Br | H | H |
| 147 | NH₂ | Cl | H | H | H |
| 148 | NH₂ | Br | Cl | H | H |
| 149 | NH₂ | SH | Br | H | H |
| 150 | SH | OH | H | H | H |
| 151 | SH | NH₂ | H | H | H |
| 152 | SH | NHOMe | Cl | H | H |
| 153 | SH | NHOBz | H | H | H |
| 154 | SH | NHOH | Br | H | H |
| 155 | SH | BzhNH | Cl | H | H |
| 156 | F | F | H | H | H |
| 157 | F | Cl | Br | H | H |
| 158 | F | Br | Cl | H | H |
| 159 | F | I | H | H | H |
| 160 | Cl | F | Cl | H | H |
| 161 | Cl | Cl | H | H | H |
| 162 | Cl | Br | H | H | H |
| 163 | Cl | I | Cl | H | H |
| 164 | Br | F | Br | H | H |

TABLE 3-continued

| Cpd No. | R⁷ | R⁸ | R¹ | R³ᵃ | R⁴ᵇ |
|---|---|---|---|---|---|
| 165 | Br | Cl | H | H | H |
| 166 | Br | Br | Cl | H | H |
| 167 | Br | I | Br | H | H |
| 168 | I | F | H | H | H |
| 169 | I | Cl | Cl | H | H |
| 170 | I | Br | Br | H | H |
| 171 | I | I | H | H | H |

TABLE 4

| Cpd No. | R³ᵃ | R⁴ᵇ |
|---|---|---|
| 172 | H | H |
| 173 | Bzh | Bzh |
| 174 | Me | Me |

TABLE 5

| Cpd No. | R³ᵃ | R⁴ᵇ | W |
|---|---|---|---|
| 175 | H | H | OMe |
| 176 | H | H | OBz |
| 177 | H | H | p-NO₂—BzO— |
| 178 | Me | Me | OMe |
| 179 | Me | Me | OBz |
| 180 | Me | Me | p-NO₂—BzO— |
| 181 | Bzh | Bzh | OMe |
| 182 | Bzh | Bzh | OBz |
| 183 | Bzh | Bzh | p-NO₂—BzO— |

TABLE 6

| Cpd No. | R³ᵃ | R⁴ᵇ | Z |
|---|---|---|---|
| 184 | H | H | H |
| 185 | H | H | OH |
| 186 | H | H | OMe |
| 187 | H | H | OBz |
| 188 | H | H | p-NO₂—BzO— |
| 189 | Me | Me | H |
| 190 | Me | Me | OH |
| 191 | Me | Me | OMe |
| 192 | Me | Me | OBz |
| 193 | Bzh | Bzh | H |
| 194 | Bzh | Bzh | OH |
| 195 | Bzh | Bzh | p-NO₂—BzO— |
| 196 | Bzh | Bzh | OBz |

TABLE 7

| Cpd No. | R¹ᵃ | R³ᵃ = R⁴ᵇ | R² | R⁷ | R⁸ |
|---|---|---|---|---|---|
| 197 | Boz | Me | BozO | OH | NHAc |
| 198 | H | H | OH | OH | NHAc |
| 199 | H | H | OH | OH | NH₂ |
| 200 | Boz | Me | H | OH | NHAc |
| 201 | H | H | H | OH | NHAc |
| 202 | H | H | H | OH | NH₂ |
| 203 | Ac | Me | AcO | Cl | NHAc |
| 204 | H | H | OH | Cl | NHAc |
| 205 | H | H | OH | Cl | NH₂ |
| 206 | Ac | Me | H | Cl | NHAc |
| 207 | H | H | H | Cl | NHAc |
| 208 | H | H | H | Cl | NH₂ |
| 209 | Boz | Me | BozO | Cl | Cl |
| 210 | H | H | OH | Cl | Cl |
| 211 | Boz | Me | H | Cl | Cl |
| 212 | H | H | H | Cl | Cl |
| 213 | Ac | Me | AcO | SH | NHAc |
| 214 | H | H | OH | SH | NHAc |
| 215 | H | H | OH | SH | NH₂ |
| 216 | Ac | Me | H | SH | NHAc |
| 217 | H | H | H | SH | NHAc |
| 218 | H | H | H | SH | NH₂ |
| 219 | Boz | Me | BozO | NH₂ | NH₂ |
| 220 | H | H | OH | NH₂ | NH₂ |
| 221 | Boz | Me | H | NH₂ | NH₂ |
| 222 | H | H | H | NH₂ | NH₂ |
| 223 | Boz | Me | BozO | NH₂ | Cl |
| 224 | H | H | OH | NH₂ | Cl |
| 225 | Boz | Me | H | NH₂ | Cl |
| 226 | H | H | H | NH₂ | Cl |
| 227 | Boz | Me | BozO | NH₂ | OH |
| 228 | H | H | OH | NH₂ | OH |
| 229 | Boz | Me | H | NH₂ | OH |
| 230 | H | H | H | NH₂ | OH |
| 231 | Boz | Me | BozO | H | NH₂ |
| 232 | H | H | OH | H | NH₂ |
| 233 | Boz | Me | H | H | NH₂ |
| 234 | H | H | H | H | NH₂ |
| 235 | Boz | Me | BozO | H | OH |
| 236 | H | H | OH | H | OH |
| 237 | Boz | Me | H | H | OH |
| 238 | H | H | H | H | OH |
| 239 | Boz | Me | BozO | SH | OH |
| 240 | H | H | OH | SH | OH |
| 241 | Boz | Me | H | SH | OH |
| 242 | H | H | H | SH | OH |
| 243 | H | H | OH | OH | H |
| 244 | H | H | H | OH | H |
| 245 | H | H | OH | Cl | H |
| 246 | H | H | H | Cl | H |
| 247 | H | H | OH | SH | H |
| 248 | H | H | H | SH | H |
| 249 | H | H | OH | H | SH |
| 250 | H | H | H | H | SH |
| 251 | H | H | OH | NH₂ | SH |
| 252 | H | H | H | NH₂ | SH |

TABLE 8

| Cpd No. | R² | R¹² |
|---|---|---|
| 253 | OH | Me |
| 254 | OH | Et |
| 255 | OH | Pr |
| 256 | OH | Bu |
| 257 | OH | Pn |
| 258 | H | Me |
| 259 | H | Et |
| 260 | H | Pr |
| 261 | H | Bu |
| 262 | H | Pn |
| 263 | H | Hx |
| 264 | OH | Hx |

Of the compounds listed above, the following are preferred: Compounds Nos. 1, 2, 3, 4, 5, 6, 7, 8, 10, 11, 14, 15, 16, 17, 18, 19, 20, 21, 22, 23, 24, 25, 26, 27, 28, 29, 30, 31, 34, 35, 37, 40, 41, 44, 49, 52, 57, 62, 66, 78, 79, 80, 85, 86, 87, 93, 94, 95, 96, 97, 98, 99, 102, 104, 105, 113, 119, 129, 130, 131, 137, 138, 139, 140, 141, 142, 144, 147, 151, 161, 172, 173, 174, 175, 176, 178, 179, 184, 186, 187, 189, 191, 192, 193, 195, 196, 197, 198, 199, 200, 201, 202, 205, 208, 210, 212, 215, 218, 220, 222, 224, 226, 228, 230, 232, 234, 236, 238, 240, 242, 243, 244, 245, 246, 247, 248, 249, 250, 251 and 252.

More preferred compounds are: Compounds Nos. 1, 4, 5, 7, 8, 10, 11, 14, 17, 18, 21, 22, 25, 28, 31, 34, 35, 37, 40, 85, 87, 94, 96, 99, 104, 129, 130, 131, 137, 138, 139, 140, 147, 151, 172, 175, 176, 184, 186, 187, 197, 198, 199, 201, 202, 210 and 224.

The most preferred compounds are: Compounds Nos. 5, 8, 18, 21, 22, 25, 34, 37, 87, 96, 104, 130, 131, 139, 140, 147, 172, 198, 199, 201, 202, 210 and 224, i.e.

5. 2-Amino-6-desamino-6-hydroxygriseolic acid
8. 2-Amino-6-desamino-6-hydroxygriseolic acid 7'-amide
18. 2-Aminogriseolic acid
21. Bis(pivaloyloxymethyl) 2-amino-6-desamino-6-hydroxygriseolate
22. 2-Amino-$N^6$-methoxygriseolic acid
25. 2-Amino-$N^6$-benzyloxygriseolic acid
34. 2-Fluorogriseolic acid
37. 2-Chlorogriseolic acid
87. 2-Amino-6-desamino-6-hydroxy-7'-desoxygriseolic acid
96. 2-Amino-7'-desoxygriseolic acid
104. 2-Chloro-7'-desoxygriseolic acid
130. 2-Amino-6-desamino-6-hydroxy-2'-chloro-2'-desoxygriseolic acid
131. 2-Amino-6-desamino-6-hydroxy-2'-desoxygriseolic acid
139. 2-Amino-2'-chloro-2'-desoxygriseolic acid
140. 2-Amino-2'-desoxygriseolic acid
147. 2-Chloro-2'-desoxygriseolic acid
172. Griseolic acid $N^1$-oxide
198. 2-Acetylamino-6-desamino-6-hydroxy-4',5'-dihydrogriseolic acid
199. 2-Amino-6-desamino-6-hydroxy-4',5'-dihydrogriseolic acid
201. 2-Acetylamino-6-desamino-6-hydroxy-4',5'-dihydro-7'-desoxygriseolic acid
202. 2-Amino-6-desamino-6-hydroxy-4',5'-dihydro-7'-desoxygriseolic acid
210. 2,6-Dichloro-6-desamino-4',5'-dihydrogriseolic acid
224. 2-Chloro-4',5'-dihydrogriseolic acid The compounds of the invention may be prepared as illustrated in the following reaction schemes:

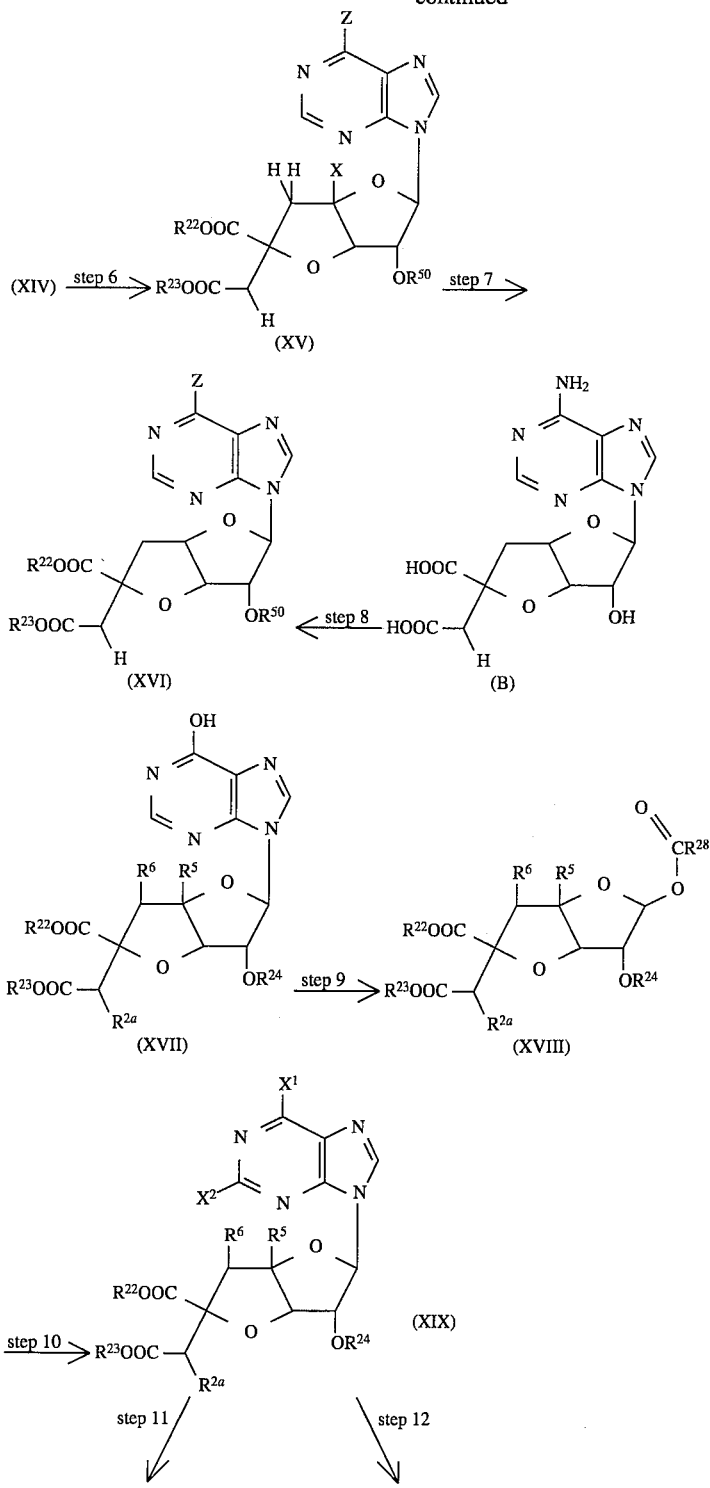

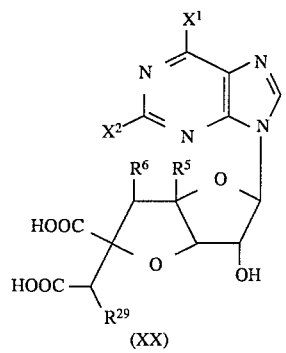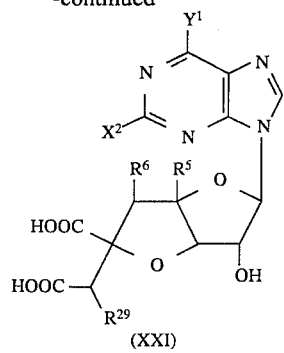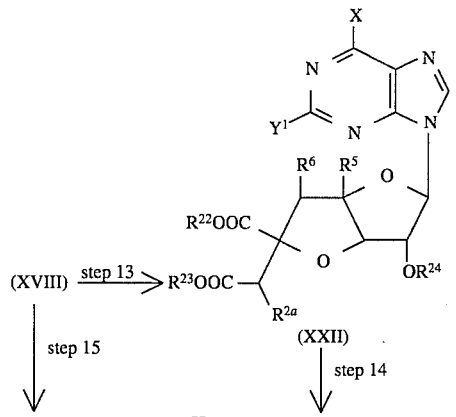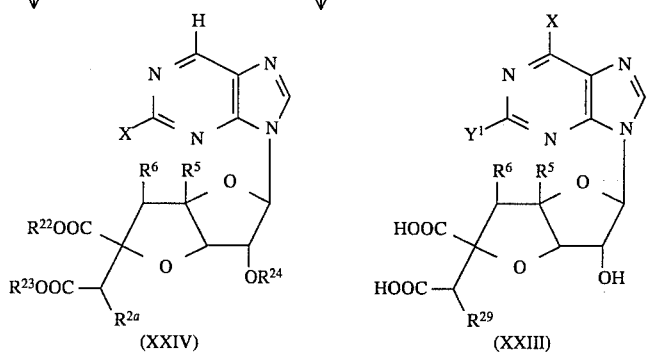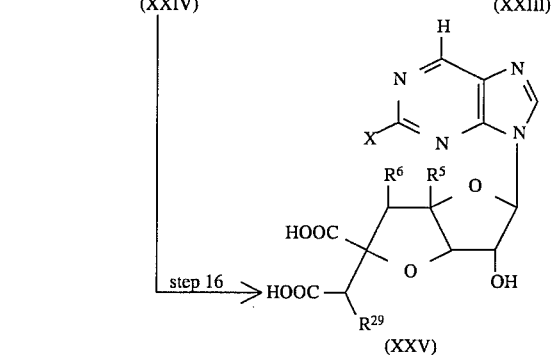

-continued
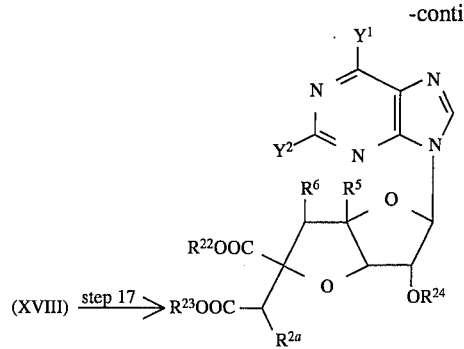
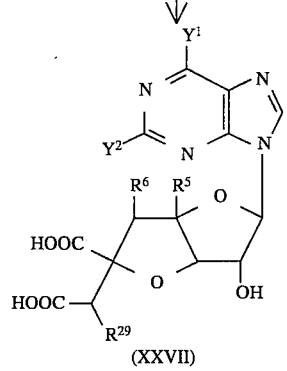
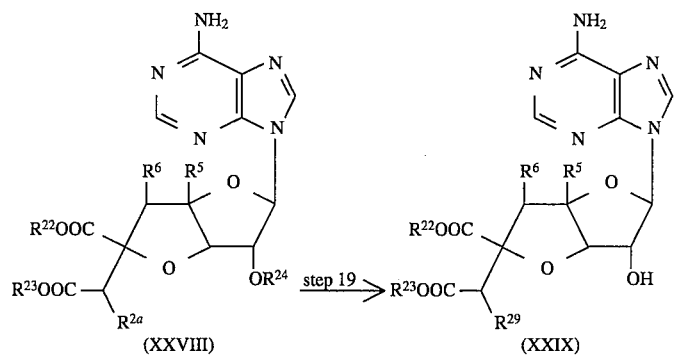
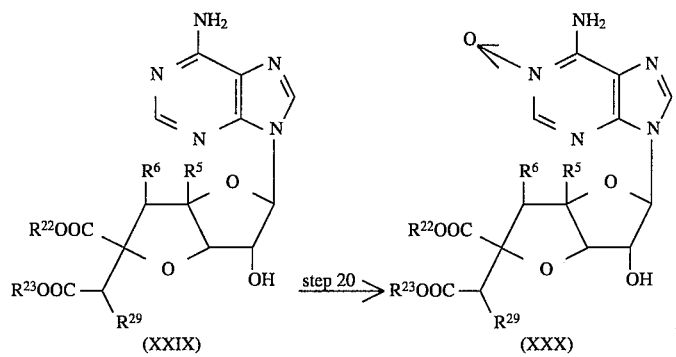

5,556,975
-continued
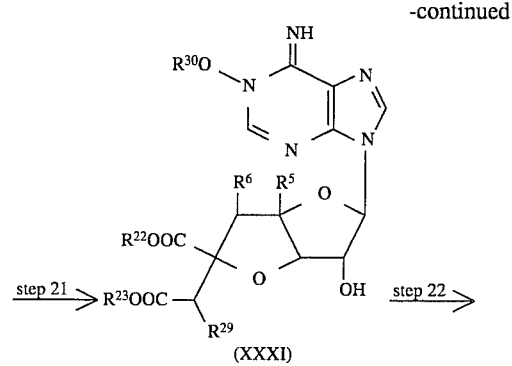
(XXXI)
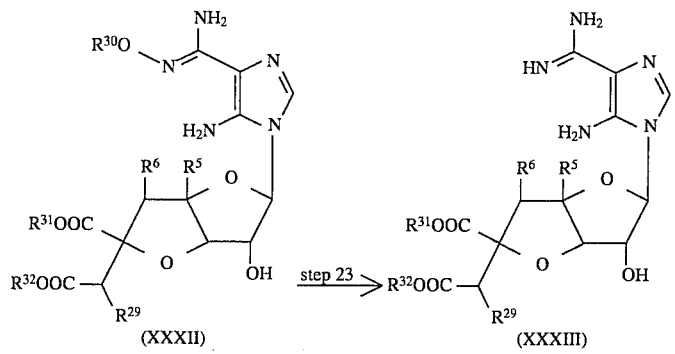
(XXXII)    (XXXIII)
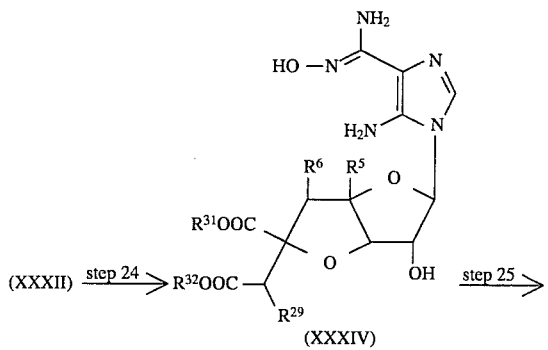
(XXXIV)
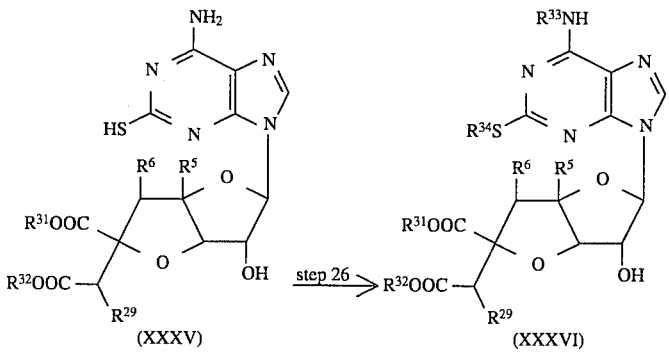
(XXXV)    (XXXVI)

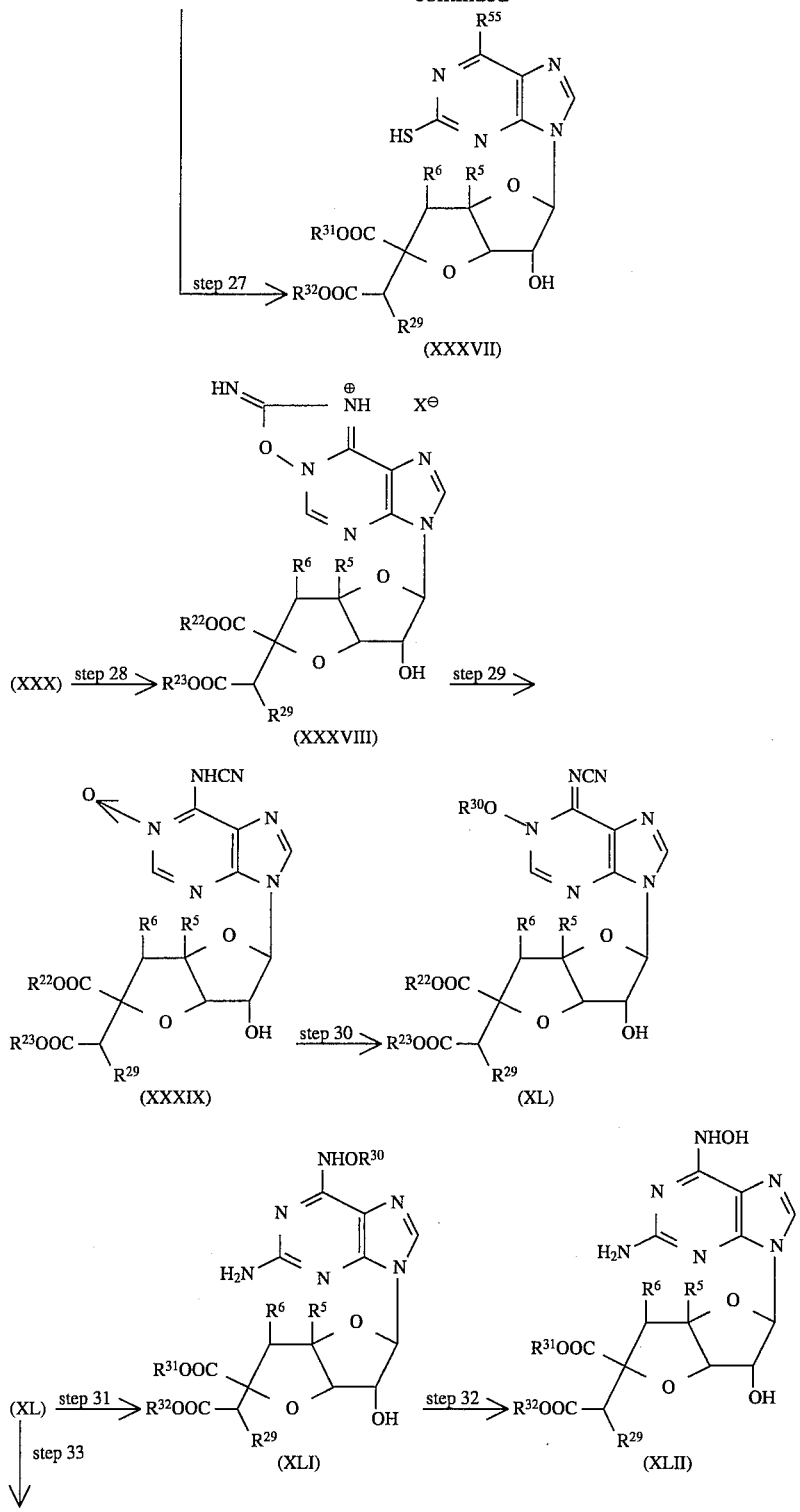

-continued
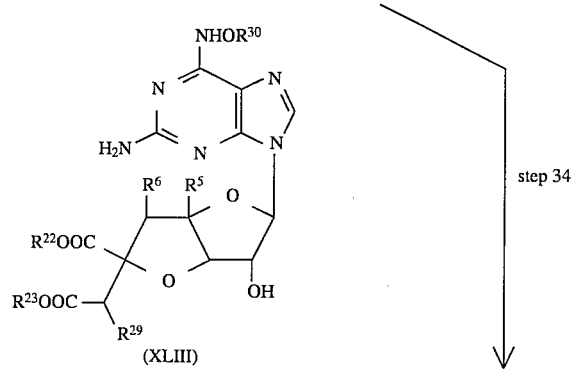
(XLIII)
step 34
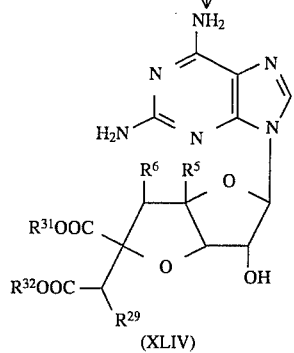
(XLIV)
(XLI) —step 35→ 
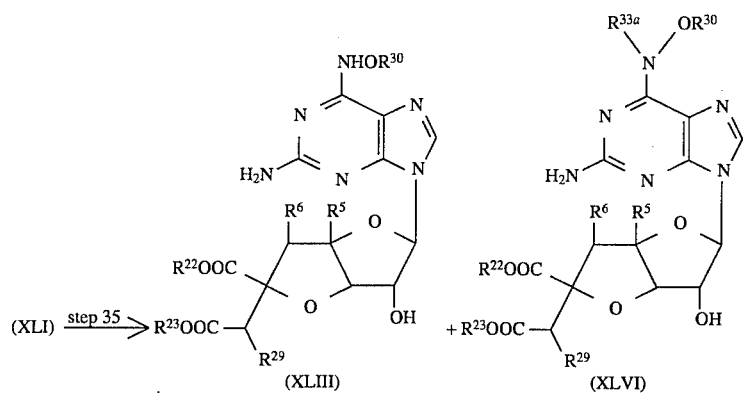
(XLIII) + (XLVI)
step 36→ 
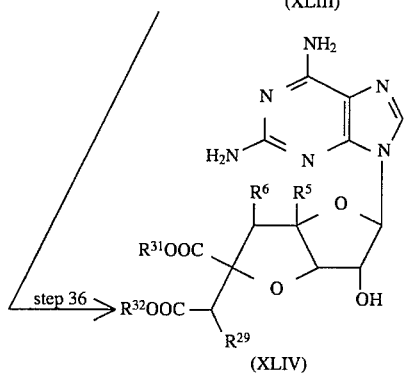
(XLIV)

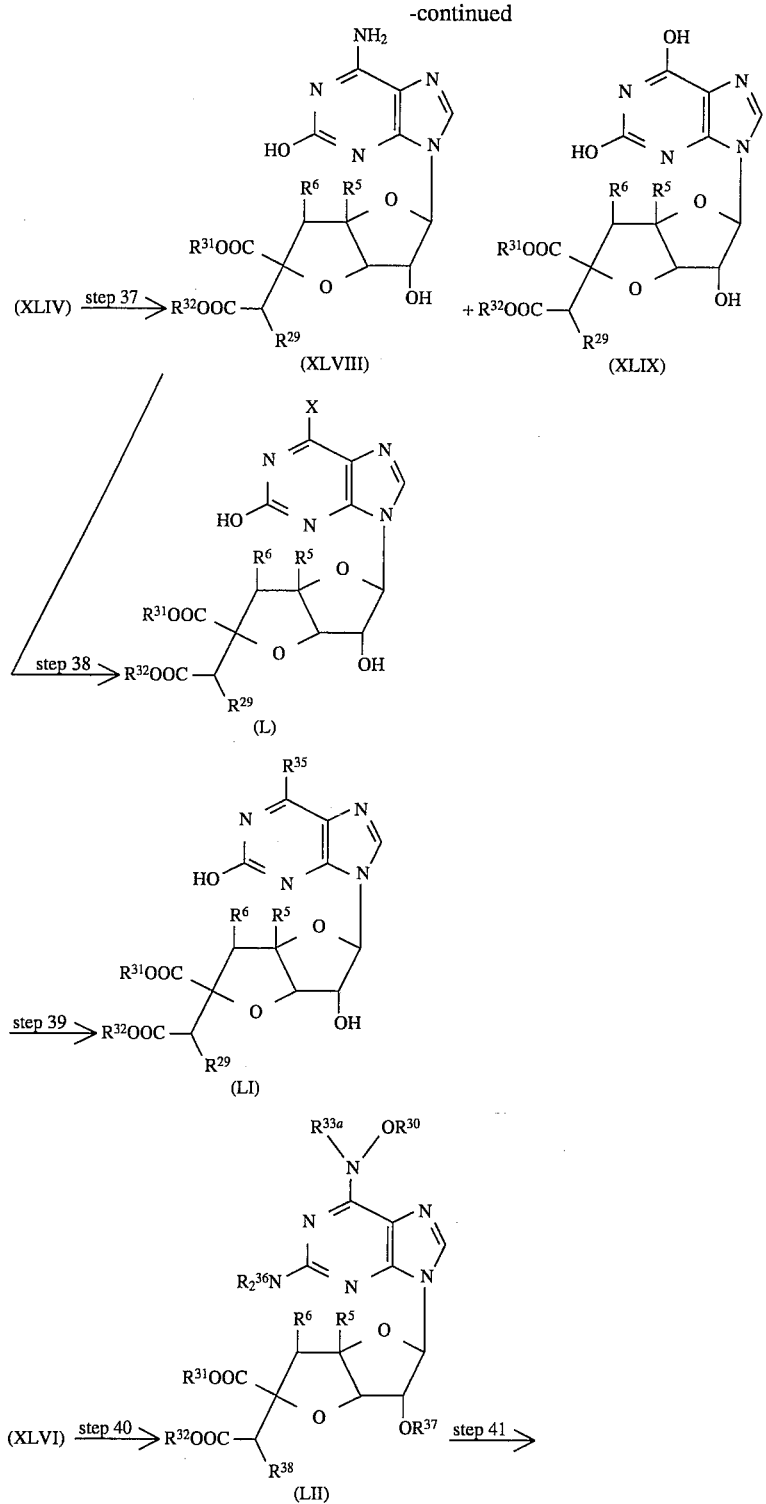

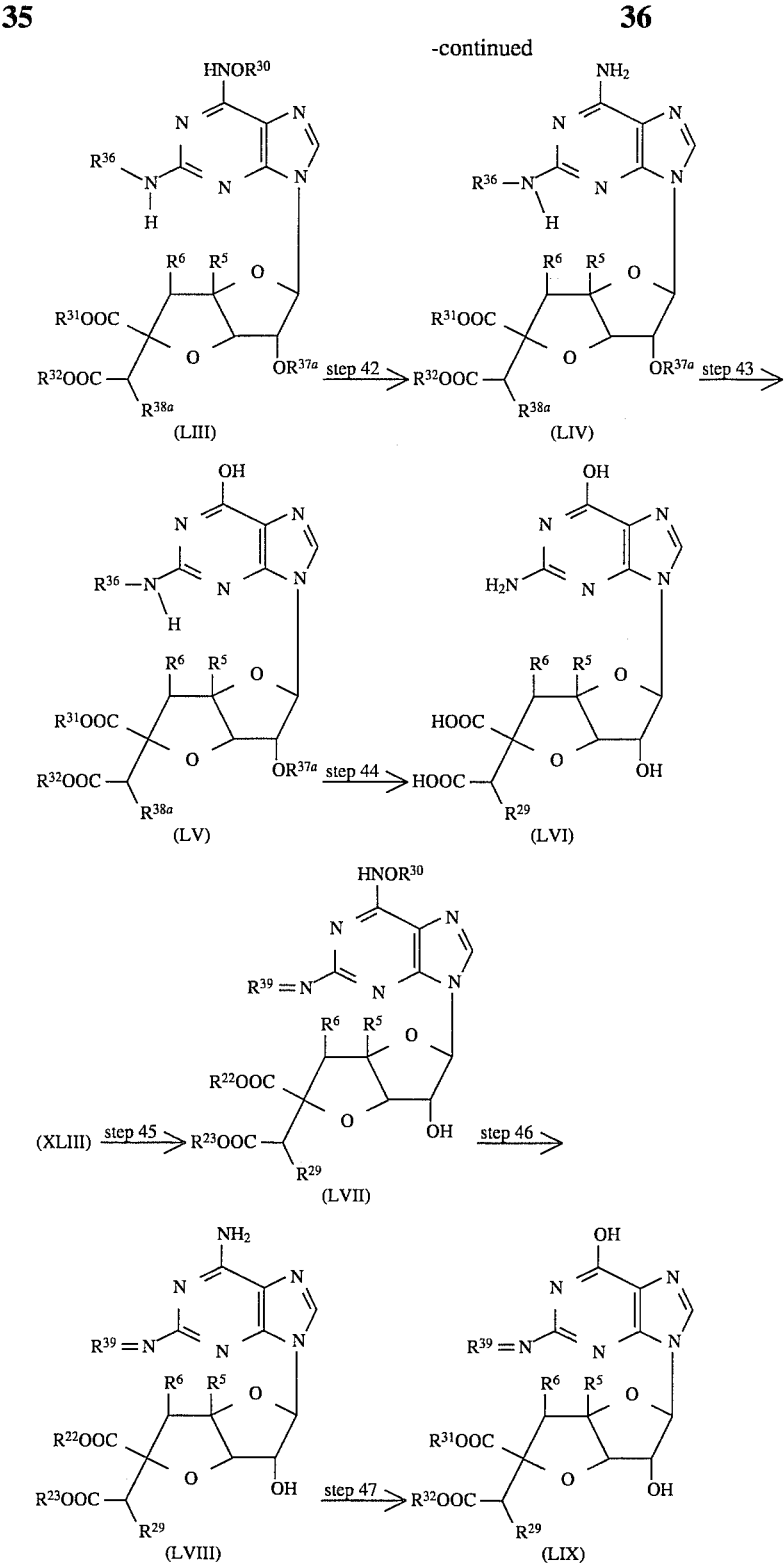

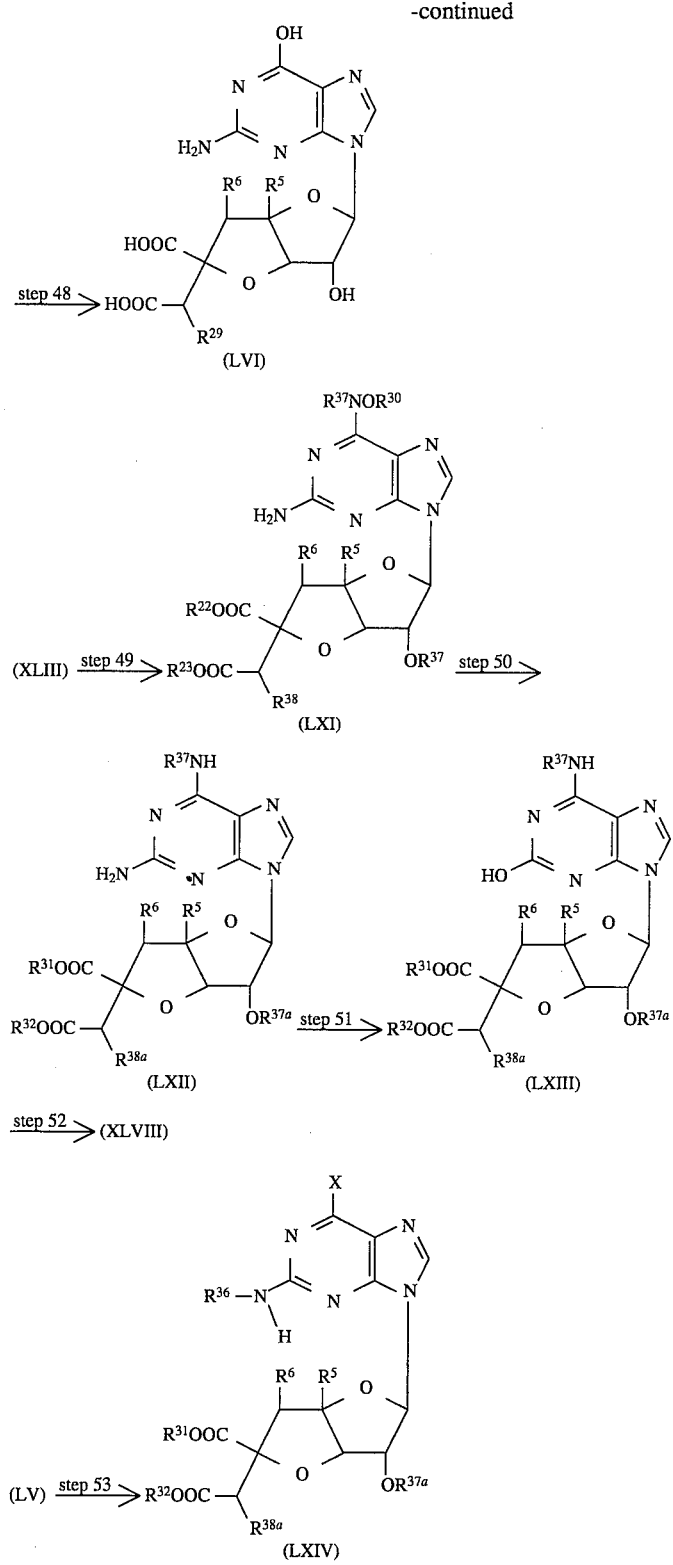

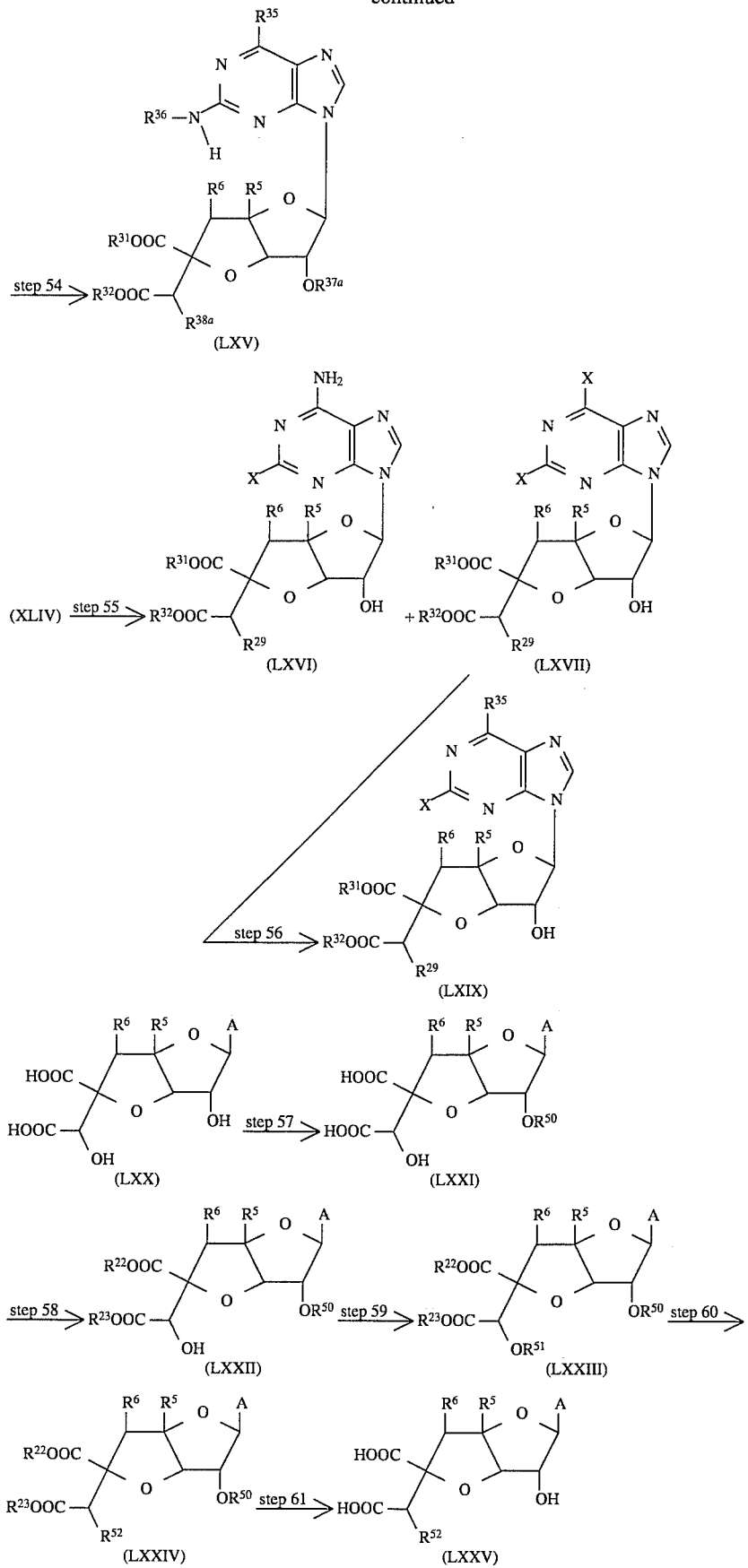

-continued

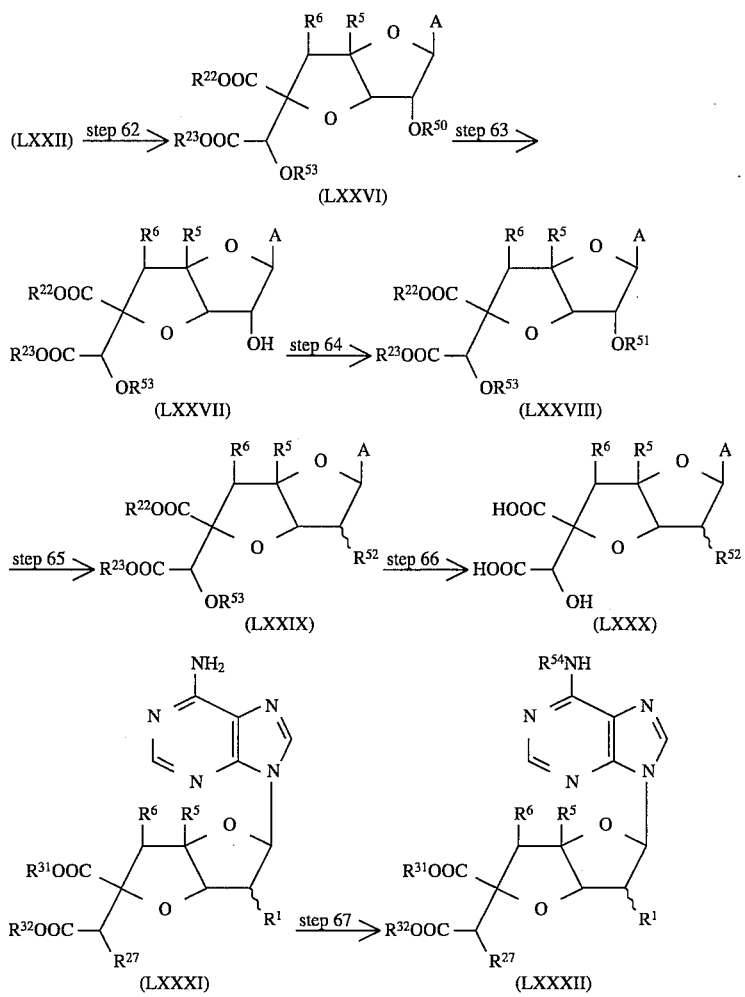

In the above formulae:

$R^1$–$R^{12}$ and A are as defined above;

$R^{2a}$ represents a hydrogen atom or a protected hydroxy group;

$R^{22}$ and $R^{23}$ are the same or different and each represents a carboxy-protecting group;

$R^{24}$ represents a hydroxy-protecting group;

X represents a halogen atom;

$R^{27}$ represents a hydrogen atom, a hydroxy group or a protected hydroxy group;

$R^{28}$ represents a lower alkyl group, e.g. any one of the lower alkyl groups defined in relation to $R^{12}$;

$X^1$ and $X^2$ are the same or different and each represents a halogen atom;

$R^{29}$ represents a hydrogen atom or a hydroxy group;

$Y^1$ and $Y^2$ are the same or different and each represents a hydrogen atom, a hydroxy group, a mercapto group, an amine group, a protected amine group or a group of formula —$SR^{28}$;

$R^{30}$ represents an alkyl group or an aralkyl group;

$R^{31}$ and $R^{32}$ are the same or different and each represents a hydrogen atom or a carboxy-protecting group;

$R^{33}$ represents a hydrogen atom, a $C_1$–$C_6$ alkyl group, an aralkyl group, a $C_1$–$C_{20}$ aliphatic acyl group or an aromatic acyl group, e.g. as defined in relation to $R^{10}$;

$R^{33a}$ represents a $C_1$–$C_6$ alkyl group or an aralkyl group;

$R^{34}$ represents a hydrogen atom, a $C_1$–$C_6$ alkyl group, a $C_1$–$C_{20}$ aliphatic acyl group, an aromatic acyl group or an aralkyl group, e.g. as defined in relation to $R^9$, provided that $R^{33}$ and $R^{34}$ do not both represent hydrogen atoms;

$R^{35}$ represents a group of formula —$OR^9$, —$NR^{10}R^{11}$ or —$SR^9$, e.g as defined in relation to $R^7$;

$R^{36}$ represents a hydrogen atom, a $C_1$–$C_{20}$ aliphatic acyl group, an aromatic acyl group or a trialkylsilyl group;

$R^{37}$ represents a $C_1$–$C_{20}$ aliphatic acyl group, an aromatic acyl group or a trialkylsilyl group;

$R^{37a}$ represents any of the groups defined for $R^{37}$ or a hydrogen atom;

$R^{38}$ represents a hydrogen atom, a $C_1$–$C_{20}$ aliphatic acyloxy group, an aromatic acyloxy group or a trialkylsilyloxy group;

$R^{38a}$ represents any of the groups defined for $R^{38}$ or a hydroxy group;

$R^{39}$ represents a substituted methylene group (e.g. as defined in relation to the substituted methylene group which may be represented by $R^{10}$ and $R^{11}$ together);

Z represents a hydroxy group or an amino group;

$R^{50}$ represents an aliphatic acyl group, an aromatic acyl group or a trialkylsilyl group;

$R^{51}$ represents a $C_1$–$C_6$ alkylsulfonyl group, a $C_1$–$C_6$ fluoroalkylsulfonyl group or an arylsulfonyl group;

$R^{52}$ represents a hydrogen atom or a halogen atom;

$R^{53}$ represents a tetrahydropyranyl group or a trialkylsilyl group (e.g. as defined in relation to $R^9$);

$R^{54}$ represents a $C_1$–$C_6$ alkyl group; and $R^{55}$ represents a hydroxy group, a halogen atom, a hydrazino group, a substituted amino group, an amino group protected by a substituted methylene group or a group of formula —$OR^9$ or —$SR^9$, as defined above.

In these reaction schemes, the starting materials are either griseolic acid, which has the formula (A) or dihydrodesoxygriseolic acid, which has the formula (B), given below:

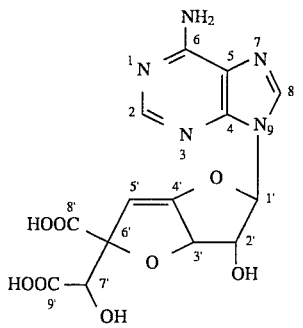

(A)

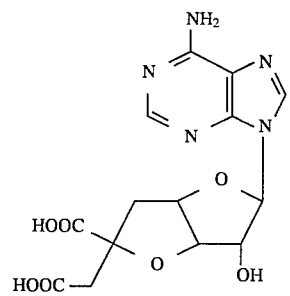

(B)

In the above formula (A), representing griseolic acid, we have indicated, for the avoidance of doubt, the numbering system employed throughout this specification.

As already described above, griseolic acid is a known compound disclosed, for example, in European Patent Specification No. 29,329 or in U.S. Pat. No. 4,460,765. Dihydrodesoxygriseolic acid was disclosed in European Patent Publication No. 0162715, published after the priority hereof. Both griseolic acid and dihydrodesoxygriseolic acid may be produced by cultivating suitable microorganisms of the genus Streptomyces, especially *Streptomyces griseoaurantiacus* SANK 63479 (deposited on 9th Oct. 1979 at the Fermentation Research Institute, Agency of Industrial Science and Technology, Japan, whence it is available under the Accession No. FERM-P5223, and on 22nd Oct. 1980 at the Agricultural Research Service, Peoria, U.S.A., whence it is available under the Accession No. NRRL 12314). Full details of the characteristics of *Streptomyces griseoaurantiacus* SANK 63479 are given in European Patent Publication No. 29,329A and in U.S. Pat. No. 4,460,765.

Step 1

In this step, griseolic acid (A) is reacted to protect its hydroxy and carboxy groups. The nature of the reaction employed will depend upon the nature of the protecting groups which are desired and the following reactions are given purely for illustrative purposes. It will, of course, be understood that any reaction known in the art for protecting carboxy groups or hydroxy groups may equally be employed in this step.

In order to protect the carboxy groups, the griseolic acid (A) is preferably reacted with a diazo compound, for example diazomethane or diphenyldiazomethane, or with a triazene compound, particularly a p-tolyltriazene derivative, such as N-methyl-p-tolyltriazene. The reaction is preferably effected in the presence of a solvent, the nature of which is not critical, provided that it has no adverse effect upon the reaction and provided that the starting materials can be dissolved in the solvent, at least to some extent. Suitable solvents include, for example: ketones, such as acetone; ethers, such as tetrahydrofuran; amides, such as dimethylformamide; and mixtures of water with one or more of the above organic solvents. The reaction will take place over a wide range of temperatures and the particular reaction temperature chosen is not critical, although we generally prefer to carry out the reaction at a temperature of from –20° C. to +50° C. The time required for the reaction will vary, depending upon many factors, notably the nature of the starting materials and the reaction temperature; however, for example, at room temperature, the reaction will normally require a period of from 1 to 24 hours.

Before or after the protection of the carboxy groups, the hydroxy groups of griseolic acid are also protected. This may be achieved, for example, by reacting the griseolic acid or carboxy-protected griseolic acid with an acid halide, such as acetyl chloride or benzoyl bromide, or with an acid anhydride, such as acetic anhydride, in the presence of a base. The reaction is preferably effected in the presence of a solvent, the nature of which is not critical, provided that it has no adverse effect upon the reaction. In general, we prefer to use pyridine, which also serves as the base. The reaction will take place over a wide range of temperatures and the particular reaction temperature chosen is not critical; however, we generally prefer to carry out the reaction at a temperature within the range from –20° C. to room temperature. The time required for the reaction may vary widely, depending upon many factors, notably the nature of the reagents and the reaction temperature; however, at temperatures within the range suggested, a period of from 1 to 15 hours will normally suffice.

If desired, the amino group at the 6-position of the griseolic acid is also converted to a hydroxy group. This reaction is preferably effected by reacting the griseolic acid or protected griseolic acid with a salt of nitrous acid, such as sodium nitrite, in the presence of acetic acid. The reaction is preferably effected in the presence of a solvent, the nature of which is not critical and, accordingly, we normally prefer to employ aqueous acetic acid. If the starting material is only slightly soluble, an acetic acid buffer of pH about 4 may be used. The reaction will take place over a wide range of temperatures, although we generally find it convenient to carry out the reaction at about room temperature. The time required for the reaction may vary widely, depending upon many factors, notably the nature of the reagents and the reaction temperature; however, at the suggested temperature, a period of from 15 to 50 hours will normally suffice.

Step 2

In this step, a hydrogen halide is added across the double bond of the griseolic acid derivative of formula (X), to give the compound of formula (XI). The nature of the hydrogen halide H-X employed in this reaction will depend upon the nature of the halogen atom X which it is desired to introduce, but we generally prefer to use hydrochloric acid, hydrobromic acid or hydroiodic acid. The reaction is preferably effected in the presence of a solvent, the nature of which is not critical, provided that it has no adverse effect upon the reaction and that it can dissolve the starting materials, at least to some degree. An example of a suitable solvent is an organic acid, such as acetic acid. The reaction will take place over a wide range of temperatures, for example from 0° C. to 100° C., although we generally find it convenient either to carry out the reaction at a temperature in the range from 0° C. to room temperature or with heating at a temperature in the range from 80° C. to 100° C. The time required for the reaction may vary widely, depending upon many factors, notably the reaction temperature and the natures of the solvent and reagents, but a period of from 1 to 72 hours will normally suffice.

Step 3

In this step, the halogen atom X at the 4'-position of the compound of formula (XI), prepared in Step 2, is removed by reduction. The reducing agent is preferably either a tri-substituted tin hydride, such as tributyltin hydride, in an aromatic hydrocarbon solvent, such as benzene, or zinc powder, in which case the solvent is preferably a lower aliphatic acid, such as acetic acid, or alcohol, such as methanol or ethanol. When the tri-substituted tin hydride is used as the reducing agent, the reaction is preferably carried out at about the boiling temperature of the solvent and the period required for the reaction is generally from 2 to 10 hours. When zinc powder is the reducing agent, the reaction is preferably effected at a temperature from room temperature to 100° C. and the period required is generally from 2 to 20 hours.

Step 4

In this step, griseolic acid, of formula (A), is converted to a derivative thereof of formula (XIII).

The hydroxy group at the 2'-position may be protected by reaction with an acylating agent, e.g. as also described in Step 1. to introduce the acyl group $R^{50}$, and then the carboxy groups of the griseolic acid may be protected. If desired, the 6-amino group of the griseolic acid may be converted to a hydroxy group, employing the appropriate reactions described Step 1, and this conversion may take place before or after the two above-mentioned protecting steps.

The hydroxy group at the 7'-position is converted to a sulfonyloxy group —$OR^{51}$ by reacting the compound with a sulfonylating agent, for example a lower alkylsulfonyl halide (such as methanesulfonyl chloride), an arylsulfonyl halide (such as p-toluenesulfonyl chloride) or a fluorinated lower alkylsulfonyl halide (such as trifluoromethanesulfonyl chloride). The reaction is preferably effected in the presence of an acid-binding agent, whose function is to remove from the reaction medium the hydrogen halide liberated by reaction. Suitable acid-binding agents include pyridine and dimethylaminopyridine. The reaction is preferably effected in the presence of a solvent, the nature of which is not critical, provided that it does not have any adverse effect upon the reaction. Suitable solvents include halogenated hydrocarbons, especially halogenated aliphatic hydrocarbons, such as methylene chloride or chloroform. The reaction will take place over a wide range of temperatures and there is no particular limitation on the precise temperature chosen; we generally find it convenient to carry out the reaction at a temperature within the range from −10° C. to room temperature. The time required for the reaction will vary widely, depending upon many factors, notably the reaction temperature and the nature of the reagents; however, a period of from 1 to 20 hours will normally suffice.

Step 5

In this step, the sulfonyloxy group at the 7'-position of the compound of formula (XIII) is replaced, by a halogen atom (by reaction with an anhydrous lithium halide in an acid amide such as dimethylformamide) and then by a hydrogen atom (by a reducing agent).

The former reaction is preferably carried out by the same method as described in the under-mentioned Step 60.

The reducing agent is preferably zinc in aqueous acetic acid, in which case the aqueous acetic acid itself may serve as the reaction solvent. The reaction will take place over a wide range of temperatures, for example from 0° C. to 150° C. and the time required for the reaction, which may vary widely, is generally from 1 to 10 hours.

Steps 6 and 7

In these steps, the compound of formula (XIV), prepared as described in Step 5, is first reacted with a hydrogen halide to prepare a compound of formula (XV), and then this compound of formula (XV) is subjected to reduction to give the compound or formula (XVI). The reactions involved in these steps are precisely the same as those described above in relation to Steps 2 and 3 and may be carried out employing the same reagents and reaction conditions.

Step 8

In this step, dihydrodesoxygriseolic acid of formula (B) has its carboxy and hydroxy groups protected and optionally has its 6-amino group converted to a hydroxy group. The reactions involved are precisely the same as described in relation to Step 1 and may be carried out employing the same reagents and under the same reaction conditions.

Step 9

The starting material for this step, the compound of formula (XVII), may be any of the compounds of formulae (XII) or (XVI), prepared as described above. In this step, the nucleic acid base at the 1'-position is converted to an alkanoyloxy group by reacting the compound of formula (XVII) with (i) sulfuric acid or trifluoromethanesulfonic acid, (ii) a lower carboxylic acid and (iii) an anhydride thereof. The reaction is preferably effected in the presence of a solvent, the nature of which is not critical, provided that it has no adverse effect upon the reaction and that the reagents will dissolve in it, at least to some degree. Lower aliphatic carboxylic acids, which also serve as a reagent, are the preferred solvents. The reaction will take place over a wide range of temperatures, for example from 0° C. to 100° C.; in general, we prefer to carry out the reaction either at a temperature from 0° C. to room temperature or, with heating, at a temperature from 80° C. to 100° C. The time required for the reaction will vary, depending upon many factors, notably the reaction solvent and the reaction temperature, but a period of from 1 to 72 hours will normally suffice.

Step 10

In this step, the sugar derivative (XVIII), prepared as described in Step 9, is subjected to a glycosidation reaction with a trimethylsilylated nucleic acid base in the presence of a Lewis acid catalyst by the conventional methods described, for example, by S. Suzaki et al [Chem. Pharm. Bull., 18, 172(1970)] or H. Vorbrueggen et al [Chem. Ber., 106, 3039(197)] to give the compound of formula (XIX).

The nucleic acid base employed is a purine derivative corresponding to the nucleic acid base portion which it is desired to introduce and this may be trimethylsilylated by the conventional method described by A. E. Pierce et al [Silylation of Organic Compounds, 434 (1968)].

There is no particular limitation on the nature of the Lewis acid employed in the glycosidation reaction and an example of a suitable Lewis acid is tin tetrachloride trimethylsilyl trifluoromethanesulfonate. The reaction is preferably effected in the presence of a solvent, the nature of which is critical, provided that it has no adverse effect upon the reaction. Suitable solvents are polar solvents, such as 1,2-dichloroethane or acetonitrile. The reaction will take place over a wide range of temperatures and the precise reaction temperature chosen is not particularly critical. We generally prefer to carry out the reaction at a temperature of from room temperature to 150° C. The time required for the reaction may vary widely, depending upon many factors, notably the nature of the reagents and the reaction temperature; however, at a temperature within the suggested range, a period of from 24 hours to 72 hours will normally suffice.

Where the substituent on the nucleic acid base to be silylated is a hydroxy group, a mercapto group, an alkylthio group, a halogen atom or a hydrogen atom, the nucleic acid base is silylated directly. Where the nucleic acid base has an amino substituent, we prefer that this amino substituent should first be protected by acylation, prior to silylation. The ratio of yields of the substitutional isomers at the 7- and 9-positions varies depending on the reaction temperature. For example, glycosidation of bistrimethylsilyl $N^2$-acetylguanine at room temperature yields more of the compound substituted at the 7-position than of the compound substituted at the 9-position. On the other hand, the same reaction at 80° C. yields more of the 9-isomer than of the 7-isomer.

Step 11

In this step, the acyl group or groups at the 2'-position and possibly also at the 7'-position are removed to give free hydroxy groups and the carboxy-protecting groups are also removed. The compound of formula (XIX) is preferably dissolved in a dilute aqueous alkaline solution, for example a 0.1–1 N aqueous alkaline solution, preferably a solution of sodium hydroxide or potassium hydroxide, and allowed to stand to remove the protecting groups. This reaction will take place over a wide range of temperatures, but we generally find it convenient to carry out the reaction at about room temperature. The time required for the reaction may vary widely, but, at the suggested temperature, a period of from 1 to 10 hours will normally suffice.

Step 12

In this step, the compound of formula (XIX), prepared as described in Step 10, is subjected to a reaction to convert selectively the halogen atom at the 6-position to an optionally substituted mercapto group with an alkyl group, or a hydrogen atom or a hydroxy group or an amino group or a protected amino group. The reaction employed may be carried out, for example, as described by L. B. Townsend [Nucleic Acid Chemistry, 2, 693 (1978)], by reacting the compound of formula (XIX) with various nucleophiles, such as sodium bisulfide, a sodium alkanethiolate, sodium hydroxide, alcoholic ammonia, methylamine or dimethylamine. The reaction is preferably effected in the presence of a solvent, the nature of which is not critical, provided that it has no adverse effect upon the reaction. Suitable solvents include lower alcohols, such as methanol or ethanol. The reaction will take place over a wide range of temperatures, although we generally find it convenient to carry out the reaction at a temperature within the range from room temperature to 150° C., preferably in a sealed tube. The time required for the reaction may vary widely, depending upon many factors, notably the nature of the nucleophile and the reaction temperature; however, at temperatures within the range suggested, a period of from 2 to 20 hours will normally suffice.

This reaction will normally result in removal of protecting groups.

Step. 13

This is a glycosidation reaction and is essentially the same as that described in Step 10 and may be carried out employing the same reaction conditions, to give a compound of formula (XXII).

Step 14

In this step, hydroxy-protecting groups and carboxy-protecting groups are removed, and this may be carried out essentially as described in Step 11, employing the same reagents and reaction conditions. Where the group $Y^1$ represents a protected amino group, for example an acetylamino group, the protecting group may be removed by hydrolysis. This is accomplished by using an alkali, for example methanolic ammonia (preferably about 20% methanolic ammonia). The reaction will take place over a wide range of temperatures, although we generally find it convenient to carry out the reaction at about room temperature. The time required for the reaction may vary widely; however, at the suggested temperature, a period of from 24 to 50 hours will normally suffice.

Step 15

In this step, the sugar derivative of formula (XVIII) is reacted with a trimethylsilylated nucleic acid base, in accordance with the glycosidation reaction described in Step 10, to give a compound of formula (XXIV). The reaction conditions and reagents are essentially as described in relation to Step 10.

Step 16

In this step, the protecting groups are removed to give a compound of formula (XXV). This reaction is essentially the same as that described in Step 11 and may be carried out employing the same reagents and reaction conditions.

Step 17

In this step, the sugar derivative of formula (XVIII) is subjected to a glycosidation reaction with a trimethylsilylated nucleic acid base, to give a compound of formula (XXVI). The reagents and reaction conditions are essentially as described above in relation to Step 10.

Step 18

In this step, the compound of formula (XXVI) prepared in Step 17, is subjected to a reaction to remove protecting groups and give the compound of formula (XXVII). The reactions involved are essentially as described in Step 11 and may be carried out employing the same reagents and reaction conditions.

Step 19

In this step, the protected 2'-hydroxy and 7'-hydroxy groups (where $R^{2a}$ is a protected hydroxy group) of the compound of formula (XXVIII), which may be any of the compounds of formulae (X), (XII), (XIV) or (XVI), prepared as described above, are deprotected to give the compound of formula (XXIX). This may be effected by the hydrolysis reaction described in Step 11 and may be carried out under the same conditions and employing the same reagents, although care should be taken not to effect hydrolysis also of the carboxy-protecting groups. If these are hydrolized, then they may be reinstated by the esterification method described in Step 1.

Step 20

In this step, the compound of formula (XXIX) is converted into the $N^1$-oxide of formula (XXX).

The reaction is preferably effected by reacting the compound of formula (XXIX) with a peroxide, preferably in a solvent. The nature of the solvent employed for this reaction is not particularly critical, provided that it has no adverse effect upon the reaction and provided that it can dissolve the reagents, at least to some extent. Examples of preferred solvents are the lower alcohols, such as methanol or ethanol. There is also no particular limitation on the nature of the peroxide to be employed and examples include hydrogen peroxide and organic peracids, such as m-chloroperbenzoic acid. The organic peracids, such as m-chloroperbenzoic acid, are preferred. The reaction will take place over a wide range of temperatures, although we generally prefer to carry out the reaction at a temperature from 0° C. to 60° C., more preferably at about room temperature. The time required for the reaction may vary widely, depending upon many factors, notably the reaction temperature and the nature of the reagents; however, at a temperature within the range suggested, a period of from 5 to 48 hours will normally suffice.

Step 21

In this step, the $N^1$-oxide is converted to an $N^1$-alkoxy or $N^1$-aralkyloxy compound of formula (XXXI) by reacting the $N^1$-oxide (XXX) with a lower alkyl halide or aralkyl halide in the presence of an organic base and preferably in the presence of a solvent. The nature of the solvent employed is not particularly critical, provided that it has no adverse effect upon the reaction and provided that it can dissolve the reagents, at least to some extent. Suitable solvents include acid amides, such as dimethylformamide or dimethylacetamide. Suitable organic bases include trialkylamines, such as triethylamine. There is no particular limitation on the nature of the halide, provided that it is capable of alkylating or aralkylating a hydroxy group. Suitable lower alkyl halides include methyl iodide, whilst suitable lower aralkyl halides include benzyl bromide and p-nitrobenzyl bromide. The reaction will take place over a wide range of temperatures, although we generally find it convenient to carry out the reaction at a temperature of from 0° C. to 100° C., more preferably at about room temperature. The time required for the reaction may vary widely, depending upon many factors, notably the nature of the reagents and the reaction temperature; however, a period of from 1 to 20 hours will normally suffice.

Step 22

In this step, a compound of formula (XXXII) is prepared by a ring-opening reaction of the $N^1$-alkoxy or $N^1$-aralkyloxy compound of formula (XXXI), followed by removal of the resulting formyl group.

These reactions are preferably effected by reacting the compound of formula (XXXI) with an aqueous alkaline solution. Suitable aqueous alkaline solutions include aqueous solutions of alkali metal hydroxides, such as sodium hydroxide. A preferred solution is a 1.5 N aqueous solution of sodium hydroxide. The reaction will take place over a wide range of temperatures, for example from $-10°$ C. to $+100°$ C. The time required for the reaction may vary widely, depending upon many factors, notably the nature and concentration of the reagents and the reaction temperature; however, employing the reagents and temperatures suggested, a period of from 6 minutes to 10 days will normally be required. This reaction will simultaneously remove the carboxy-protecting groups $R^{22}$ and $R^{23}$. Accordingly if these groups are required, they must subsequently be reinstated by the esterification reaction described in Step 1. In general, we prefer for subsequent steps that these carboxy groups should be protected and hence that $R^{31}$ and $R^{32}$ should both represent carboxy-protecting groups.

Step 23

In this step, the compound of formula (XXXII) is reduced to give the compound of formula (XXXIII) and, if desired, carboxy-protecting groups are removed and/or converted to amides and/or converted to salts and/or to other carboxy-protecting groups.

Reduction of the compound of formula (XXXII) to remove the group —$OR^{30}$ is preferably effected by treating the compound with an active metal in the presence of a solvent. The nature of the solvent is not particularly critical, provided that it has no adverse effect upon the reaction and that it is capable of dissolving the starting materials at least to some extent. A suitable solvent is a mixture of a dilute aqueous acid, such as dilute aqueous hydrochloric acid, and a water-miscible organic solvent, such as acetone. A preferred solvent is a mixture of equal volumes of 1N aqueous hydrochloric acid and acetone. There is equally no particular restriction on the nature of the active metal employed, provided that it can be used for a reduction reaction where an acid serves as the proton donor. Such active metals as Raney nickel are preferred. The reaction will take place over a wide range of temperatures, although we generally find it convenient to carry out the reaction at a temperature from 0° C. to 50° C. The time required for the reaction may vary widely, depending upon many factors, notably the nature of the reagents and the reaction temperature; however, under the conditions suggested above, a period of from 1 to 10 hours will normally suffice.

If desired, the protecting groups may be removed, the nature of the removal reaction depending upon the nature of the protecting group, as is well known in the art.

Where a lower alkyl group is employed as a carboxy-protecting group, it may be removed by treating the compound with a base, particularly an alkali metal hydroxide, such as sodium hydroxide. Preferably, we employ an aqueous solution of the alkali metal hydroxide, for example a 1N aqueous solution of sodium hydroxide. The reaction is preferably effected in the presence of a solvent, the nature of which is not critical to the invention, provided that it has no adverse effect upon the reaction. In general, an aqueous solution is effective. The reaction will take place over a wide range of temperatures, although we generally find it convenient to carry out the reaction at about room temperature. The time required for the reaction may vary widely, depending upon many factors, notably the nature of the reagents and reaction temperature; however, under the conditions suggested above, a period of from 1 to 15 hours will normally suffice.

When the carboxy-protecting group is a diaryl-substituted methyl group, such as a diphenylmethyl (i.e. benzhydryl) group, it is preferably removed under acidic conditions in the presence of a solvent. The solvent employed in this reaction is not particularly critical, provided that it has no adverse effect upon the reaction. Examples of suitable solvents include aromatic hydrocarbons and aromatic ethers, such as anisole. The acid is preferably a fluorinated organic acid, such as trifluoroacetic acid. The reaction will take place over a wide range of temperatures, although we generally find it convenient to carry out the reaction at about room temperature. The time required for the reaction may vary widely, but a period of from 30 minutes to 10 hours will normally suffice.

Where the carboxy-protecting group is an aralkyl group or a lower haloalkyl group, it is preferably removed by reduction. Preferred reducing agents are: in the case of lower haloalkyl groups, zinc/aqueous acetic acid; and, in the case of aralkyl groups, hydrogen and a catalyst (such palladium-on-carbon or platinum) or an alkali metal sulfide (such as potassium sulfide or sodium sulfide). The reaction is preferably effected in the presence of a solvent, the nature of which is not critical, provided that it has no adverse effect upon the reaction. Examples of suitable solvents include: alcohols, such as methanol or ethanol; ethers, such as tetrahydrofuran or dioxane; fatty acids, such as acetic acid; or a mixture of one or more of these organic solvents with water. The time required for the reaction is not particularly critical, although we generally prefer to carry out the reaction at a temperature between 0° C. and room temperature. At such a temperature, the reaction will normally require a period of from 5 minutes to 12 hours.

When the carboxy-protecting group is an alkoxymethyl group, it may be removed by treating the compound with an acid in a solvent. Preferred acids include: hydrochloric acid; a mixture of acetic acid with sulfuric acid; or a mixture of p-toluenesulfonic acid with acetic acid. There is no particular restriction upon the nature of the solvent to be employed in this reaction, provided that it has no adverse effect upon the reaction. Suitable solvents include: alcohols, such as methanol or ethanol; ethers, such as tetrahydrofuran or dioxane; and mixtures of one or more of these solvents with water. There is no particular restriction on the reaction temperature, although we generally find it convenient to carry out the reaction at a temperature of from 0° C. to 50° C., at which a period of from 10 minutes to 18 hours will normally suffice.

If the carboxy-protecting group is removed by treatment with aqueous ammonia, this will generally result in conversion of the carboxy groups at the 8' and 7' positions to carbamoyl groups.

If desired, the free carboxylic acid may be converted to a salt, for example an alkali metal salt, by conventional means. For example, a suitable reaction comprises dissolving the acid in a mixture of water and a water-immiscible organic solvent, such as ethyl acetate, adding an aqueous solution of the appropriate alkali metal carbonate or bicarbonate (such as potassium carbonate or sodium bicarbonate) at an appropriate temperature (e.g. from 0° C. to room temperature) and then adjusting the pH (e.g. to a value of about 7) to allow the salt to be separated by precipitation.

The resulting salt or the carboxylic acid compound can, if desired, be converted to an ester in which the carboxy groups are protected with easily hydrolizable in vivo protecting groups. The salt or acid is first dissolved in an appropriate solvent, for example: an ether, such as tetrahydrofuran; or a polar solvent, such as dimethylformamide, dimethyl sulfoxide, hexamethylphosphoric triamide or triethyl phosphate. It is then allowed to react with at least 2 equivalents of a base, for example an organic base (such as triethylamine or dicyclohexylamine), an alkali metal hydride (such as sodium hydride) or an alkali metal carbonate or bicarbonate (such as sodium carbonate, potassium carbonate or sodium bicarbonate) to form a salt, and the resulting salt is allowed to react with a lower aliphatic acyloxymethyl halide (such as acetoxymethyl chloride or propionyloxymethyl bromide), with a lower alkoxycarbonyloxyethyl halide, (such as 1-methoxycarbonyloxyethyl chloride or 1-ethoxycarbonyloxyethyl iodide), with a phthalidyl halide or with a (2-oxo-5-methyl-1,3-dioxolen-4-yl)methyl halide. The reaction is preferably effected in the presence of a solvent, the nature of which is not critical, provided that it has no adverse effect upon the reaction. Suitable solvents include the polar solvents referred to above. The reaction will take place over a wide range of temperatures, although we generally find it convenient to carry out the reaction at a temperature from 0° to 100° C. The time required for the reaction may vary widely; however, under the conditions suggested above, a period of from 30 minutes to 10 hours will normally suffice. The desired step above may also be employed, if desired, in steps 24, 25 and 26 and also in each step of Steps 27, 32, 33, 34, 36, 37, 38, 50 and 54.

Step 24

In this step, the compound of formula (XXXII) prepared as described in Step 22 is subjected to catalytic reduction to remove the alkyl or aralkyl group $R^{30}$ and yield the hydroxyimino compound of formula (XXXIV). The reaction is preferably effected in the presence of a solvent, the nature of which is not critical, provided that it has no adverse effect upon the reaction and that it can dissolve the starting materials, at least to some extent. Organic carboxylic acids, particularly fatty acids such as acetic acid, are preferred. There is no particular restriction on the nature of the catalyst and any catalyst commonly used for catalytic reduction processes may equally be employed here. We prefer platinum oxide, platinum-on-carbon or palladium-on-carbon, more preferably palladium chloride adsorbed onto active charcoal. The reaction is preferably carried out by stirring a mixture of the catalyst and the compound of formula (XXXII) in the chosen solvent under an atmosphere of hydrogen. The reaction will take place over a wide range of temperatures and the particular temperature chosen is not critical. In general, we find it convenient to carry out the reaction at a temperature of from 5° to 60° C. The time required for the reaction may vary widely, depending upon many factors, including the nature of the compound (XXXII) and the reaction conditions, especially reaction temperature; however, under the conditions suggested above, a period of from 1 to 10 hours will normally suffice. If desired, the optional process described in Step 23 may be carried out with the resulting compound.

Step 25

In this step, the compound of formula (XXXIV) prepared as described in Step 24 is reacted with carbon disulfide to cause cyclization and produce the compound of formula (XXXV). The reaction is preferably effected in the presence of a solvent, the nature of which is not critical, provided that it has no adverse effect upon the reaction and that it can dissolve the starting materials, at least to some degree. We prefer to employ a mixture of a mildly basic solvent (such as pyridine) with a lower alcohol (such as methanol), preferably a mixture of equal volumes of these two components. The preferred amount of carbon disulfide is about one fifth that of the solvent. The reaction will take place over a wide range of temperatures, and we generally find it convenient to carry out the reaction at a temperature from 0° C. to 150° C., more preferably at about 80° C. The time required for the reaction will vary, depending upon many factors, notably the nature of the starting material and the reaction temperature; however, under the conditions suggested above, a period of from 10 to 30 hours will normally suffice. If desired, the optional process described in Step 23 may be carried out with the resulting compound.

Step 26

In this step, the mercapto compound of formula (XXXV) is reacted with an alkyl halide, aralkyl halide, aliphatic acyl halide or aromatic acyl halide of formula $R^{33}X$ and/or $R^{34}X$ in order to introduce such an alkyl, aralkyl or acyl group onto the mercapto group or the 6-amino group. The reaction is preferably effected in the presence of a solvent, the nature of which is not critical, provided that it has no adverse effect upon the reaction and that it can dissolve the starting materials, at least to some degree. We prefer to use either water or a lower alcohol (such as methanol) or a mixture of water and such an alcohol. The reaction is preferably effected in the presence of an acid-binding agent, the nature of which is not critical, provided that it is capable of removing the hydrogen halide HX generated by the reaction. Suitable acid-binding agents include: inorganic bases, particularly alkali metal hydroxides, such as sodium hydroxide or potassium hydroxide; and organic bases, particularly organic amines and more particularly trialkylamines such as triethylamine. In general, we particularly prefer to use an aqueous solution of an alkali metal hydroxide, such as sodium hydroxide. The reagent $R^{33}X$ or $R^{34}X$ may be: a lower alkyl halide, such as methyl iodide; an aralkyl halide, such as benzyl bromide; a lower aliphatic acyl halide, such as acetyl chloride; or an aromatic acyl halide, such as benzoyl bromide. The reaction will take place over a wide range of temperatures, although we generally prefer to carry out the reaction at a temperature in the range from 0° C. to 80° C., more preferably at about room temperature. The time required for the reaction may vary widely, depending upon many factors, notably the nature of the reagents and the reaction temperature; however, under the conditions suggested above, a period of from 1 to 10 hours will normally suffice.

Where the reaction is carried out employing an alkyl halide or aralkyl halide, the mercapto group at the 2-position is preferentially alkylated or aralkylated. On the other hand, if the reagent is an aliphatic acyl halide or aromatic acyl halide, the 6-amino group is preferentially acylated. Accordingly, it is possible to introduce the same or different groups into the compound as the groups $R^{33}$ and $R^{34}$.

If desired, the optional process described in Step 23 may be carried out with the resulting compound.

Step 27

In this step, the 6-amino group of the compound of formula (XXXV) is converted into a hydroxy group and, if desired, the hydroxy group is halogenated to replace it by a halogen atom; if desired, this halogen atom may then be replaced by a hydrazino group, a substituted amino group, an amino group protected by a substituted methylene group or a group of formula —$OR^9$ or —$SR^9$. In addition, if desired, the reaction of the optional steps of Step 23 may also be carried out in each process and/or if desired, removal of mercapto-protecting, amino-protecting or hydroxy-protecting groups may be carried out in a final process.

The conversion of the amino group to a hydroxy group is carried out as described in relation to the same reaction involved in Step 1 and may be effected using the same reaction conditions and reagents.

Halogenation go replace the hydroxy group by a halogen atom may be carried out using any conventional halogenating agent capable of converting a hydroxy group on a heterocyclic compound to a halogen atom. Examples include phosphorus oxyhalides, such as phosphorus oxychloride or phosphorus oxybromide; and thionyl halides, such as thionyl chloride; of these, phosphorus oxychloride is preferred. The reaction is preferably effected in the presence of an acid-binding agent, for example: and acid amide, such as dimethylformamide; an aromatic tertiary amine, such as diethylaniline or dimethylaniline; or a lower trialkylamine, such as triethylamine.

The reaction is preferably effected in the presence of a solvent, the nature of which is not critical, provided that it does not interfere with the reaction and generally we prefer to use an excess of the halogenating agent itself as the solvent; alternatively, it is possible to use an excess of the halogenating agent in admixture with another organic solvent, for example: an ester, such as ethyl acetate; or a halogenated hydrocarbon, preferably halogenated aliphatic hydrocarbon, such as methylene chloride. The reaction will take place over a wide range of temperatures and the precise temperature chosen is not particularly critical to the reaction; in general, we prefer to carry out the reaction at about the boiling point of the solvent employed. The time required for the reaction may vary widely, depending upon many factors, notably the nature of the reagents and the reaction temperature; however, under the conditions suggested above, a period of from 10 minutes to 5 hours will normally suffice.

The resulting halogen atom at the 6-position can then, if desired, be converted to one of the substituents mentioned above by reaction with a nucleophilic reagent belonging to one of the following classes: hydrazines; mono- and dialkylamines, such as methylamine or dimethylamine; amines protected with a substituted methylene group, such as benzylideneamine or the other amines corresponding to the substituted methyleneimino groups referred to above; hydroxy-substituted lower alkylamines, such as 2-hydroxyethylamin; amino-substituted lower alkylamines, such as 2-aminoethylamine; aralkylamines, such as benzylamine; arylamines, such as aniline, α-naphthylamine or β-naphthylamine; hydroxylamine; lower alkoxyamines, such as methoxyamine; aralkyloxyamines; such as benzyloxyamine; alkali metal hydroxides, such as sodium hydroxide; alkali metal hydrosulfides, such as sodium hydrosulfide; alkali metal alkanethiolates, such as sodium methanethiolate; and alkali metal alkoxides, such as sodium methoxide. When the nucleophilic reagent employed is an amine, the reaction can be carried out using an excess of the amine without any added acid-binding agent. However, when one of the above nucleophilic agents other than an amine is used, the reaction is preferably effected in the presence of an acid-binding agent which is not itself a nucleophile; trialkylamines, such as triethylamine are suitable. The reaction is preferably effected in the presence of a solvent, the nature of which is not critical, provided that it has no adverse effect upon the reaction. Suitable solvents include, for example: lower alcohols, such as methanol or ethanol; acid amides, such as dimethylformamide or dimethylacetamide; and polar solvents, such as trimethyl sulfoxide, hexamethylphosphoric triamide or triethyl phosphate. The reaction will take place over a wide range of temperatures and the precise reaction temperature chosen is not particularly critical; we generally prefer to carry out the reaction at a temperature within the range from room temperature to the boiling point of the solvent employed. The time required for the reaction may vary widely, depending upon many factors, notably the nature of the reagents and the reaction temperature; however, at a temperature within the suggested range, a period of from 6 to 20 hours will normally suffice.

If desired, protecting groups may be removed in this step and the reactions employed to remove such protecting groups will vary in a conventional manner, depending upon the precise nature of the protecting group.

If a trialkylsilyl group is employed as a hydroxy-protecting group, it may be removed by treating the compound with a compound capable of producing fluorine anions, for example tetrabutylammonium fluoride. The reaction is preferably effected in the presence of a solvent, the nature of which is not particularly critical, provided that it has no adverse effect upon the reaction. Suitable solvents include, for example, ethers, such as tetrahydrofuran or dioxane. The reaction temperature is not particularly critical, although we generally prefer to carry out the reaction at about room temperature. The time required may vary widely, depending upon many factors; however, under the conditions suggested, a period of from 10 to 18 hours will normally suffice.

When an aralkyloxycarbonyl group or aralkyl group is employed as a hydroxy-protecting group, it may be removed by contacting the compound with a reducing agent, for example: using a catalyst such as palladium-on-activated carbon or platinum in the presence of hydrogen, preferably at room temperature; or by using an alkali metal sulfide, such as sodium sulfide or potassium sulfide. The reaction is preferably effected in the presence of a solvent, the nature of which is not critical, provided that it has no adverse effect upon the reaction. Suitable solvents include, for example: alcohols, such as methanol or ethanol; ethers, such as tetrahydrofuran or dioxane; fatty acids, such as acetic acid; or a mixture of one or more of these organic solvents with water. The reaction will take place over a wide range of temperatures, although we generally find it convenient to employ room temperature or below, for example from 0° C. to room temperature. The time required for the reaction may vary widely, depending upon many factors, notably the nature of the starting materials and reducing agents; however, a period of from 5 minutes to 12 hours will normally suffice.

When an aliphatic acyl group, aromatic acyl group or alkoxycarbonyl group is employed as the hydroxy-protecting group, it may be removed by treating the compound with a base in the presence of an aqueous solvent. There is no particular limitation on the nature of the solvent to be employed and any such solvent commonly used in hydrolysis may equally be used here. Examples of preferred solvents include water and mixtures of water with one or more organic solvents, for example: alcohols, such as methanol, ethanol or propanol; or ethers, such as tetrahydrofuran or dioxane. There is equally no particular limitation upon the nature of the base, provided that it does not affect other parts of the molecule. Examples of suitable bases include: alkali metal carbonates, such as sodium carbonate or potassium carbonate; alkali metal hydroxides, such as sodium hydroxide or potassium hydroxide; and methanolic ammonia. The more preferred bases fur removal of protecting groups from nucleic acid bases are methanolic ammonia; for other cases, a 1 N aqueous solution of sodium hydroxide is preferred. The reaction will take place over a wide range of temperatures and the particular reaction temperature chosen is not critical; however, we generally prefer carry out the reaction at room temperature or below, for example an a temperature of from 0° C. to room temperature. The time required for the reaction may vary widely, depending upon many factors, notably the nature of the starting materials and the reaction temperature; however, under the conditions suggested above, the reaction will normally be complete within a period of from 1 to 10 hours.

When a tetrahydropyranyl group, tetrahydrofuranyl group, their thio analogs, an alkoxymethyl group or a substituted ethyl group is employed as a hydroxy-protecting group, it may be removed by treating the compound with an acid in a solvent. Examples of preferred acids include: hydrochloric acid; a mixture or acetic acid with sulfuric acid; or a mixture of p-toluenesulfonic acid with acetic acid. The reaction is preferably effected in the presence of a solvent, the nature of which is not critical, provided that it has no adverse effect upon the reaction. Suitable solvents include, for example: alcohols, such as methanol or ethanol; ethers, such as tetrahydrofuran or dioxane; or mixtures of water with one or more of these organic solvents. The reaction will take place over a wide range of temperatures, for example at a temperature from 0° C. to 50° C. The time required for the reaction may vary widely, depending upon many factors, notably the nature of the starting materials and acids; however, under the conditions suggested above, a period of from 10 minutes to 18 hours will normally suffice.

When an alkenyloxycarbonyl group is employed as the hydroxy-protecting group, it may be removed by treating the compound with a base. This reaction can be conducted under the same conditions as are employed for elimination of a hydroxy-protecting group when that hydroxy-protecting group is an aliphatic acyl, aromatic acyl or alkoxycarbonyl group. When the hydroxy-protecting group is an allyloxycarbonyl group, it may be removed simply by using palladium and triphenylphosphine or nickel tetracarbonyl and this reaction has the advantage that few side reactions occur.

The reactions described for removing hydroxy-protecting groups may be accompanied by simultaneous elimination of carboxy-protecting groups, mercapto-protecting groups and amino-protecting groups, depending upon the nature of those groups.

After completion of these reactions, the desired compounds may be recovered from the reaction mixture by conventional means, for example by purifying the resulting compound by recrystallization, preparative thin layer chromatography or column chromatography.

When an aliphatic acyl or aromatic acyl group is employed as the mercapto-protecting group, it may be removed by treatment with a base. The reaction conditions employed are the same as those employed for removal of an aliphatic acyl or aromatic acyl group employed as a hydroxy-protecting group. This may be accompanied by simultaneous elimination of a carboxy-protecting group, a hydroxy-protecting group or an amino-protecting group.

After completion of the reaction, the desired compounds, may, if required, be recovered from the reaction mixture by conventional means, and, for example, purified by recrystallization, preparative thin layer chromatography or column chromatography.

When an aliphatic acyl group, aromatic acyl group or substituted methylene group is employed as an amino-protecting group, it may be removed by treating the compound with a base. The reagents and reaction conditions employed are the same as those used to remove aliphatic acyl and aromatic acyl groups when they are used as hydroxy-protecting groups. Accordingly, other protecting groups may be removed simultaneously.

When a trialkylsilyl group is employed as an amino-protecting group, it may be removed by the same reactions as are employed to remove a trialkylsilyl group when used as a hydroxy-protecting group.

These reactions for removing amino-protecting groups may be accompanied by simultaneous elimination of carboxy-protecting groups, hydroxy-protecting groups or mercapto-protecting groups. After completion of the reactions, the desired compounds may, if required, be recovered from the reaction mixture by conventional means and, if desired, purified by recrystallization, preparative thin layer chromatography or column chromatography.

The order in which the elimination of the hydroxy-protecting groups, carboxy-protecting groups, amino-protecting groups and mercapto-protecting groups are carried out is not critical and removal of these groups may be accomplished in any order, sequentially or simultaneously.
Step 2

In this step, the $N^1$-oxide of formula (XXX), prepared as described in Step 20, is converted to a polycyclic compound of formula (XXXVIII) by reaction with a cyanogen halide, such as cyanogen bromide. The reaction is preferably effected in the presence of a solvent, the nature of which is not critical, provided that it has no adverse effect upon the reaction and that it can dissolve the starting materials, at least to some extent. Suitable solvents include, for example: lower alcohols, such as methanol or ethanol. The reaction temperature is not particularly critical, although we generally prefer to carry out the reaction at a temperature within the range from −10° C. to +50° C., more preferably at about room temperature. The time required for the reaction may vary widely, depending upon many factors, notably the nature of the reagents and the reaction temperature; however, under the conditions suggested above, a period of from 1 to 10 hours will normally suffice.
Step 29

In this reaction, the polycyclic compound of formula (XXXVIII) is converted to the $N^6$-cyano $N^1$-oxide of formula (XXXIX) by reaction with a basic compound in a solvent. The nature of the solvent employed is not particularly critical, provided that it has no adverse effect upon the reaction and that it can dissolved the starting materials at least to some extent. Examples of preferred solvents include $C_1$–$C_4$ alcohols, such as methanol or ethanol. There is no particular limitation upon the nature of the basic compound to be employed, although we generally find it convenient to use a solvent saturated with ammonia gas, preferably methanolic ammonia. The reaction will take place over a wide range of temperatures, for example from −10° C. to +50° C., more preferably at about room temperature. The time required for the reaction may vary widely, depending upon many factors, notably the natures of the starting materials, solvents and basic compounds; however, under the conditions suggested above, a period of from 1 to 5 hours will normally suffice.

Step 30

In this step, the $N^1$-oxide (XXXIX) is converted to an $N^1$-alkoxy or $N^1$-aralkyloxy compound (XL). The reactions employed are identical with those described above in Step 21 and may be carried out employing the same reagents and reaction conditions.

Step 31

In this step, the compound of formula (XL), prepared as described in Step 30, is converted to the compound of formula (XLI). The reaction is preferably effected as follows. First, the compound of formula (XL) is treated with an alkali in a solvent at a pH value of from 12 to 13 to open its pyrimidine ring (and, incidentally, also remove the carboxy-protecting groups). The pH value of the reaction mixture is then re-adjusted to 7.0 and the mixture is heated to cause re-cyclization, thus giving a compound of formula (XLI) in which the carboxy groups are not protected (i.e. $R^{31}$ and $R^{32}$ both represent hydrogen atoms). Preferred alkalis for the first stage of this reaction include aqueous solutions of alkali metal hydroxides, such as sodium hydroxide or potassium hydroxide. There is no particular restriction upon the nature of the solvent employed, provided that it does not interfere with the reaction and that it can dissolve the starting materials, at least to some extent. We prefer to use water or a mixture of water with a lower alcohol (such as methanol or ethanol). Both reactions will take place over a wide range of temperatures and the precise temperature chosen is not particularly critical. A temperature of about room temperature is preferred for the ring-opening reaction and, at such temperature and at a pH value of about 12, the reaction will normally be complete within from 30 to 60 minutes. The cyclization reaction is preferably effected at a temperature of from 0° to 150° C. and, at such a temperature, the reaction will generally be complete within a period of from 1 to 5 hours.

If desired, following these reactions, the carboxy-protecting groups may be reinstated by the esterification reactions described in Step 1.

Step 32

In this step, the alkyl or aralkyl group $R^{30}$ is removed and replaced by a hydrogen atom. The reaction is the same as that described in Step 24 and may be carried out under the same reaction conditions and employing the same reagents. If desired, the process described in Step 23 may be carried out with the resulting compound.

Step 33

In this step, a ring-opening and re-cyclization reaction is carried out, similar to that described in Step 31, but keeping the carboxy-protecting groups intact. The reaction is preferably effected in the presence of a solvent, the nature of which is particularly critical, provided that it does not interfere with the reaction and that it can dissolve the starting material at least to some extent. We prefer that the solvent should be able to maintain the reaction solution at a pH value in the range from 6 to 8 and, accordingly, we prefer to use a mixture of a pH 6 to 8 buffer solution with a lower alcohol (such as methanol or ethanol), preferably a mixture of a pH 7.0 buffer and methanol. The reaction will take place over a wide range of temperatures, for example from 30° to 150° C. The time required for the reaction may vary, depending upon many factors, notably the reaction temperature, pH and the natures of the starting materials and solvents; however, under the conditions suggested above, a period of from 3 to 10 hours will normally suffice. If desired, the optional process described in Step 23 may be carried out with the resulting compound.

Step 34

In this step, the alkoxy or aralkyloxy group —$OR^{30}$ is replaced by a hydrogen atom. The reactions employed are similar to those described in Step 23 and may be carried out employing the same reagents and under the same reaction conditions, to give the desired compound of formula (XLIV). If desired, the optional process described in Step 23 may be carried out with the resulting compound.

Step 35

In this step, where the compound of formula (XLI) has free carboxy groups (i.e. $R^{31}$ and $R^{32}$ are hydrogen atoms), these may be protected by reactions similar to those described in Step 1. In particular, we prefer that benzhydryl groups should be introduced as carboxy-protecting groups by reacting the compound with diphenyldiazomethane. Under the conditions employed for this reaction, the protecting group, e.g. benzhydryl group, may also be introduced into the 6-amino group, to give the compound of formula (XLVI).

The reaction is preferably effected in a solvent comprising a mixture of water and a water-miscible organic solvent, such as acetone, having a pH of from 1 to 2. The reaction is preferably effected at room temperature and will generally require from 1 to 10 hours.

Step 36

In this step, the alkoxy or aralkyloxy group —$OR^{30}$ is removed; the reaction and reaction conditions involved are similar to those described in relation to Step 23. If desired, the optional process described in Step 23 may be carried out with the resulting compound.

Step 37

In this step, the compound of formula (XLIV), prepared as described in Step 34 or 36, is converted to a mono-hydroxy compound (XLVIII) or a dihydroxy compound of formula (XLIX) by reaction with a nitrite, for example as described in Step 1. If desired, the optional process described in Step 23 may be carried out with the resulting compound.

Step 38

In this step, the 6-amino group of the compound of formula (XLVIII) is converted to a halogen atom by reaction with a nitrite in a hydrohalic acid or haloboric acid as described in Step 1. Preferred hydrohalic acids include, for example hydroiodic acid, hydrobromic acid or hydrochloric acid. Preferred haloboric acids include, for example, fluoroboric acid. The reaction will take place over a wide range of temperatures, for example from −30° C. to +50° C. The time required for the reaction may vary widely, depending upon the nature of the starting materials and the reaction temperature; however, a period of from 1 to 20 hours will normally suffice. If desired, the optional process described in Step 23 may be carried out with the resulting compound.

Step 39

In this step, a group $R^{35}$ (i.e. a group of formula —$OR^9$, —$NR^{10}R^{11}$ or —$SR^9$) is introduced into the 6-position of the purine base. The reaction involved is similar to that described in Step 27, if desired, carrying out the optional reactions also described in Step 27.

Step 40

In this step, two groups $R^{36}$ are introduced into the 2-amino group and $R^{37}$ is introduced into the 2'-hydroxy group by reactions similar to those described hereafter in Step 49, to give a compound of formula (LII).

Steps 41–43

These steps involve: first, removal of one of the groups $R^{36}$ introduced in the previous snap and removal of the group $R^{33a}$ from the $N^6$-position; in this step, the 2'-hydroxy protecting group and/or the 7'-hydroxy protecting group and/or the carboxy protecting group may be removed. If desired, the carboxy group may be protected as described in Step 1, whilst hydroxy groups may be protected as described in Step 40. Next, there is effected; removal of the alkoxy or arylkyloxy group —$OR^{30}$ from the $N^6$-position; and conversion of the 6-amino group to a 6-hydroxy group. These reactions may be carried out as described previously employing the same reactions and reaction conditions.

Step 44

In this step all protecting groups are removed, for example as described in step 27.

Step 45

In this step, the compound of formula (XLIII), prepared as described in Step 33 is reacted with an acetal of dimethylformamide or with an aldehyde, such as benzaldehyde, and with an organic base (such as triethylamine) in order to protect the amino group at the 2-position by a substituted methylene group, such as an N,N-dimethylaminomethylene, benzylidene, p-methoxybenzylidene, p-nitrobenzylidene, salicylidene, 5-chlorosalicylidene, diphenylmethlene or (5-chloro-2-hydroxyphenyl)phenylmethylene. The reaction is preferably effected in the presence of a solvent, the nature of which is not critical, provided that it has no adverse effect upon the reaction and that it can dissolve the starting materials, at least to some extent. Suitable solvents include acid amides, such as dimethylformamide or dimethylacetamide. The reaction will take place over a wide range of temperatures, although we generally find it convenient to carry out the reaction at about room temperature. The time required for the reaction may vary widely, depending upon many factors, notably the nature of the reagents and the reaction temperature; however, under the conditions suggested above, a period of from 15 minutes to 5 hours will normally suffice.

Step 46

In this step, the alkoxy or aralkyloxy group —$OR^{30}$ is removed by a process similar to that described in Step 23, to give the compound of formula (LVIII).

Step 47

In this step, the 6-amino group is converted to a hydroxy group by reaction with a nitrite, similar to the corresponding step described in Step 1, to give the compound of formula (LIX).

Step 48

In this step, the substituted methylene group protecting the 2-amino group on the purine base is removed, together with both carboxy-protecting groups $R^{31}$ and $R^{32}$, by processes analogous to those described in relation to the optional processes in Step 27, to give the compound of formula (LVI).

Step 49

In this step, the compound of formula (XLIII) is converted to a compound of formula (LXI) by protecting the nitrogen atom at the 6-position of the purine base and the hydroxy groups in the sugar moiety with the protecting groups defined previously. This may be effected by acylation, for example by reacting the compound (XLIII) with an acylating agent, such as: an acyl halide, e.g. an aromatic acyl halide (such as benzyl chloride) or a lower aliphatic acyl halide (such as acetyl bromide or propionyl chloride); or an acid anhydride, e.g. an aromatic acid anhydride (such as benzoic anhydride) or a lower aliphatic acid anhydride (such as acetic anhydride or propionic anhydride). The reaction will take place over a wide range of temperatures, for example from $-30°$ C. to $+100°$ C. The time required for the reaction may vary widely, depending upon many factors, notably the nature of the acylating agent and the reaction temperature; however, under the conditions indicated above, a period of from 30 minutes to 50 hours will normally suffice.

Step 50

In this step, the protected compound of formula (LXI) prepared as described in Step 49 is converted to a compound of formula (LXII) by a process analagous to that of the main process of Step 23 and, if desired, the optional steps described in Step 27.

Step 51

In this step, the compound of formula (LXII) is converted to a compound of formula (LXIII) by the process described in Step 37 and, if desired, the optional steps described in Step 27.

Step 52

In this step, the compound of formula (LXIII), prepared as described in Step 51, is converted to a compound of formula (XLVIII) by removing the protecting groups from the 6-amino group on the purine base and the 2'-hydroxy group on the sugar moiety by the optional processes described in Step 27. The carboxy-protecting groups may be simultaneously removed under these conditions.

Step 53

In this step, a compound of formula (LV), prepared as described in Step 43, is converted to a compound of formula (LXIV), having a group X at the 6-position of the purine base by a procedure similar to that described in the second process of Step 27 and, if desired, the optional processes of Step 27.

Step 54

In this step, the group X at the 6-position of the purine base is replaced by a group $R^{35}$ by a process similar to that described in Step 39 and, if desired, the optional processes of Step 27.

Step 55

In this process, a compound of formula (XLIV), which may have been prepared as described in Step 34 or 36, is converted to a monohalo or dihalo compound (LXVI) or (LXVII), respectively, by processes similar to that described in Step 38, and, if desired, the optional processes described in Step 23.

Step 56

In this step, the dihalo compound (LIVII) is converted to a compound of formula (LXIX) by a process similar to that described in Step 39 and, if desired, the optional steps of Step 27.

Step 57

In this step, only the hydroxy group at the 2'-position of the sugar part of the griseolic acid derivative of formula (LXX), which can have been prepared by any of the processes described above, is acylated. This can be achieved either by:
(i) slowly adding a base (such as sodium hydroxide) to the griseolic acid derivative (LXX), followed by the addition of an acylating agent (any of those described in relation to previous acylation steps, but particularly an aromatic acyl halide, such as benzoyl chloride) to the reaction solution, whilst keeping its pH at a value of from 10 to 13; or
(ii) dissolving the griseolic acid derivative (LXX) in a buffer solution of pH from 10 to 13, followed by the addition of an acylating agent.

The reaction is preferably effected in the presence of a solvent the nature of which is not critical, provided that it has no adverse effect upon the reaction and that it can dissolve the reagents at least to some degree. A mixture of water and a water-immiscible solvent (particularly an ester, such as ethyl acetate) is preferred. The reaction will take place over a wide range of temperatures, for example from −20° C. to +50° C. The time required for the reaction may vary widely, depending upon many factors, notably the nature of the reagents and the reaction temperature; however, a period of from 1 to 10 hours will normally suffice.

Step 58

In this step, the free carboxy groups of the griseolic acid derivative of formula (LXXI) (prepared as described in Step 57) are protected by a procedure similar to the esterification described in Step 1.

Step 59

In this step, the compound of formula (LXXII), prepared as described in Step 58, is converted to a compound of formula (LXXIII) by sulfonylation. The reaction is achieved by reacting the compound of formula (LXXII) with a lower alkylsulfonyl halide (such as methanesulfonyl chloride), an arylsulfonyl halide (such as p-toluenesulfonyl chloride) or a fluorinated lower alkylsulfonyl halide (such as trifluoromethanesulfonyl chloride) and with an acid-binding agent, such as pyridine or dimethylaminopyridine. The reaction is preferably effected in the presence of a solvent, the nature of which is not critical, provided that it has no adverse effect upon the reaction. Suitable solvents include: halogenated hydrocarbons, particularly halogenated aliphatic hydrocarbons, such as methylene chloride or chloroform. The reaction will take place over a wide range of temperatures, although we generally prefer a relatively low temperature. e.g. from −10° C. to room temperature. The time required for the reaction may vary, depending upon many factors, notably the nature of the reagents and the reaction temperature; however, a period of from 1 to 20 hours will normally suffice.

Step 60

In this step, the sulfonyloxy group at the 7'-position of the compound of formula (LXXIII) is replaced by a halogen atom (by reaction with an anhydrous lithium halide in an acid amide such as dimethylformamide) and/or by a hydrogen atom (by reduction using zinc/aqueous acetic acid as described in Step 5). The former reaction is preferably effected in the presence of a solvent, the nature of which is not critical, provided that it has no adverse effect upon the reaction. Suitable solvents include such polar solvents as dimethylformamide, dimethyl sulfoxide, triethyl phosphate or hexamethylphosphoric triamide. The reaction will take place over a wide range of temperatures, for example from 0° to 150° C. The time required for the reaction may vary widely, depending upon many factors, but a period of from 1 to 10 hours will normally suffice.

Step 61

In this step, the protecting groups are removed from the compound of formula (LXXIV) by methods appropriate to the nature of the protecting group. When, for example, a pyranyl group is employed as the hydroxy-protecting group, it may be removed by treatment with an acid, such as acetic acid or p-toluenesulfonic acid, preferably with pyridine p-toluenesulfonate, in a mixed solvent comprising a lower alkanol (such as ethanol) and a halogenated hydrocarbon (such as methylene chloride). When a trialkylsilyl group is employed as the hydroxy-protecting group, it can be removed by treatment with a compound generating a fluorine anion, such as tetrabutylammonium fluoride, with an ether (such as tetrahydrofuran) serving as solvent. The reaction will take place over a wide range of temperatures, for example from room temperature to 100° C. The time required for the reaction may vary widely, depending upon many factors, but a period of 5 to 20 hours will normally suffice. Carboxy-protecting groups and/or other hydroxy-protecting groups may be removed as described in Step 27.

Step 62

In this step, the hydroxy group at the-7'-position of the compound of formula (LXXII) (prepared as described in Step 58) is protected by various methods appropriate to the particular protecting group which it is desired to introduce. If it is desired to protect the group by means of a pyranyl group, then the compound (LXXII) is allowed no react with a suitable pyran derivative, for example 3,4-dihydro-α-pyran, in the presence of an acid catalyst, such as hydrochloric acid. If the group is to be protected by means of a lower trialklsilyl group, then the compound (LIXII) is allowed to react with a trialkylsilyl halide, such as dimethyl-t-butylsilyl chloride, and with imidazole. The reactions are preferably effected in the presence of a solvent, the nature of which is not critical, provided that it has no adverse effect upon the reaction. Suitable solvents include, for example: halogenated hydrocarbons, particularly halogenated aliphatic hydrocarbons, such as chloroform; esters, such as ethyl acetate; ethers, such as dioxane; and acid amides, such as dimethylformamide. The reaction will take place over a wide range of temperatures and the particular temperature chosen is not critical to the invention. We normally find it convenient no carry out the reaction at about room temperature. The time required for the reaction may vary widely, depending upon many factors, notably the natures of the reagents and solvents and the reaction temperature; however, under the conditions suggested above, a period of from 1 to 30 hours will normally suffice.

Step 63

In this step, the 2'-hydroxy group is deprotected by removing the acyl or silyl group $R^{50}$ from the compound of formula (LXXVI) to give the compound of formula (LXXVII). The reaction is preferably effected by contacting the protected compound with an aqueous solution of an alkali metal hydroxide, such as a 1N aqueous solution of sodium hydroxide, or with 20% v/v methanolic ammonia. The reaction will take place over a wide range of temperatures, for example from −20° to +50° C. The time required for the reaction may vary widely, depending upon many factors, notably the nature of the reagents and the reaction temperature. However, under the conditions suggested, a period of from 10 minutes to 3 hours will normally suffice.

Step 64

In this step, the compound of formula (LXXVII) is sulfonylated by a process analogous to that described in Step 59, and the reaction may be carried out under the same reaction conditions and employing the same reagents, to give the compound of formula (LXXVIII).

Step 65

In this step, the sulfonyloxy group at the 2'-position of the compound of formula (LXXVIII) is replaced by a halogen atom or by a hydrogen atom. The reactions involved are similar to those described in Step 60 and may be carried out employing the same reagents and under the same reaction conditions.

Step 66

In this step, the compound of formula (LXXIX), prepared as described in Step 65, is deprotected to give the compound of formula (LXXX). The reactions involved are similar to those described in Step 61 and may be carried out employing the same reagents and under the same reaction conditions.

Since each of the substitution reactions of Steps 60 and 65 involves a Walden inversion, it affords a compound of inverted steric configuration, as compared with the initial compound. Any compound having the inverse configuration of that of the compound obtained above (i.e. the naturally occuring configuration) can be prepared, if desired, as follows: in the procedure of Step 60 or Step 65, a lower alkanoyloxy group is introduced into the starting material as $R^{52}$; this lower alkanoyloxy group is then removed by the procedure described in Step 61; and then the resulting compound is subjected again to the sequence of steps from Step 59 or to the sequence steps from Step 64, respectively.

Step 67

In the first part of Step 67, the griseolic acid or derivative thereof of formula (LXXXI) is subjected to alkylation or aralkylation with an alkylating or aralkylating agent in an inert solvent. The nature of the solvent is not particularly critical, provided that it has no adverse effect upon the reaction. Examples of suitable solvents include: alcohols, such as methanol, ethanol, isopropanol, butanol and t-butanol; ethers, such as diethyl ether, tetrahydrofuran, dioxane or ethylene glycol dimethyl ether; nitriles, such as acetonitrile; amides, such as dimethylformamide, dimethylacetamide or hexamethylphosphoric triamide; and sulfoxides, such as dimethyl sulfoxide. The preferred solvents are amides or sulfoxides.

The reaction will take place over a wide range of temperatures, but we prefer to carry out the reaction at a temperature of from 0° C. to 100° C., more preferably from room temperature to 70° C.

The time required for the reaction may vary widely, depending upon many factors, notably the reaction temperature and the natures of the solvents and reagents employed. In general, a period of from 30 minutes to 10 days will suffice. If, for example, the reaction is carried out at room temperature, it is generally complete within from 1 to 7 days; on the other hand, at 70° C., it will normally be complete within from 1 to 20 hours.

The intermediate product thus produced may be obtained from the reaction mixture by evaporating off the solvent under reduced pressure and then the product may be subjected to the next part of the Step without further isolation, in the same reaction vessel. Alternatively, if desired, the intermediate may be isolated by conventional means before being subjected to the next part of the Step.

In the second part of Step 67, the intermediate compound is subjected to a ring-opening, rearrangement and ring-closure reaction involving the pyrimidine ring and the free amino group.

In this step, the residue obtained from the alkylation or aralkylation reaction is dissolved or suspended in a suitable solvent and the pH of the resulting solution or suspension is adjusted or maintained at a value not less than 4, to effect the aforesaid ring-opening, rearrangement and ring-closure reactions. The pH value employed for these reactions is more preferably at least 5 and still more preferably at least 7.

Maintenance of the chosen pH value may be achieved, for example, either (1) by conducting the reactions in a buffer solution previously adjusted to an appropriate pH value or (2) by standing or heating the residue in an excess of an aqueous solution of an alkali metal or alkaline earth metal hydroxide or a solution containing an organic base in water or in a suitable organic solvent.

There is no particular limitation upon the nature of the buffer solution to be employed, provided that it is capable of maintaining an appropriate pH value throughout the reaction. Any conventional buffer solution, for example an acetate, phosphate, borate, ammonium bicarbonate, phthalate or citrate buffer, may be used.

Examples of suitable alkali metal and alkaline earth metal hydroxides which may be used in the aqueous solution include sodium hydroxide, potassium hydroxide, lithium hydroxide and calcium hydroxide. Examples of suitable organic bases include, for example, lower alkylamines, such as monomethylamine, dimethylamine or trimethylamine.

In general, the pH of the reaction solution is preferably maintained within the range from 4 to 12, although higher pH values may also be employed.

There is no particular limitation on the nature of the solvent employed in this reaction, provided that it does not interfere with the reactions. Suitable solvents include, for example: water; alcohols, such as methanol, ethanol or propanol; and other water-miscible solvents, such as acetone, tetrahydrofuran, dioxane, dimethylformamide or dimethyl sulfoxide. A single such solvent or a mixture of any two or more thereof may be employed. In some cases, the organic base may also act as the reaction solvent.

The reaction may take place over a wide range of temperatures, for example from 0° C. to 150° C., more preferably from 20° C. to 100° C. The temperature chosen may depend upon various factors. For example, heating may be preferable when the reaction is carried out at a pH value within the range from 4 to 10; on the other hand, the reaction will generally proceed satisfactorily at ambient temperature at a pH of 10 or above.

The time required for the reaction may vary widely, depending upon many factors, notably the nature of the substrates, the reaction temperature and the pH and nature of the buffer or other medium used, especially the temperature and pH; however, within the preferred ranges indicated above, a period of from 5 minutes to 50 hours will normally suffice. If desired, the optional steps of Step 27 may then be carried out.

After completion of any of the reactions described above, the desired product of each step may be separated from the reaction mixture by conventional means. For example, the reaction mixture is, if necessary, washed with water, and then the solvent is distilled off under reduced pressure. The residue can be purified by various means, such as recrystallization or the various chromatography techniques, such as column chromatography or preparative thin layer chromatography, to afford the desired compound.

Phosphodiesterase (PDE) inhibitory activity

Certain of the compounds of the invention were tested, identified by the numbers of the Examples hereinafter, together with theophylline as a comparison.

The test was carried out following essentially the same method of A. L. Pitnard and W. Y. Cheung [Journal of Bilogical Chemistry, 251, 5726–5737 (1976)]. A crude enzymatic solution derived from rat brains was used as the source of cAMP PDE.

$^{14}$C-labeled cAMP was used as the substrate. It was employed in a 0.2M Tris-hydrochloric acid buffer solution (pH 8.0) in an amount sufficient to provide a final concentration of 0.14 μM. "Tris" is tris-(hydroxymethyl)aminomethane. The substrate solution was mixed with an appropriate amount of the compound under test dissolved in 2.0 to 5.0 μl of dimethyl sulphoxide and with 20 μl of a snake venom solution and 40 μl of the crude enzyme solution. Sufficient Tris-hydrochloric acid buffer was added to make a total volume of 100 μl. The mixture was allowed to react at 30° C. for 20 minutes. At the end of this time, the reaction mixture was treated with an Amberlite (trade mark) IRP-58 resin and the level of residual adenosine radioactivity in the product was determined. The experiment was carried out an a number of concentration levels of each active compound and from this was calculated the 50% inhibition values ($I_{50}$).

The experiment was repeated, except that cyclic guanosine monophosphate (cGMP) was employed as the substrate instead of cAMP. The $I_{50}$ value against cGMP PDE was also calculated.

The results are shown in Table 9. where the $I_{50}$ values are given in μmoles.

TABLE 9

| Compound of Ex. No. | $I_{50}$ (μmoles) | |
| --- | --- | --- |
| | cAMP PDE | cGMP PDE |
| 4 | 50.6 | 1.5 |
| 30 | 3.3 | 0.91 |
| 34 | 0.049 | 0.014 |
| 36 | 3.4 | 0.39 |
| theophylline | 360 | 196 |

The known compound used for comparison is theophylline, which is known to inhibit both cAMP PDE and cGMP PDE and is employed therapeutically for this purpose. The least effective of those compounds of the invention tested has an $I_{50}$ value which is about an order of magnitude smaller than the corresponding value for theophylline, whilst the most effective of those compounds of the invention tested has an $I_{50}$ value some 3–4 orders of magnitude lower, indicating that the activities of the compounds of the invention as PDE inhibitors are extraordinarily strong. The differences in the activities against cAMP PDE and cGMP PDE are also clearly shown.

The compounds thus show a variety of therapeutic uses, for example: in the treatment of cardiovascular problems; as an antiasthmatic agent; as a smooth muscle relaxant; as a psychotropic or neurotropic agent; as an anti-inflammatory agent; in the therapy of cancer; and as a treatment for diabetes.

The compounds of the invention may accordingly be used as therapeutic agents for various cerebral circulatory disorders, such as cerebral apoplexy sequelae and cerebral infarction sequelae, and as brain metabolism activators, for example for the therapy of senile dementia or traumatic brain infarction. The compounds of the invention may be administered orally or non-orally (for example by subcutaneous or intramuscular injection).

The compounds of the invention may be administered orally in the form of solid preparations which may, if necessary, contain various conventional additives. Such additives include: diluents, such as sugars and cellulose preparations; binders, such as starch, gums and methylcellulose; and disintegrating agents. The dosage will vary depending upon the symptoms, age and body weight of the patient. For example, in the case of an adult human patient, a suitable daily does would be from 0.1 to 100 mg/kg of the active compound, which may be administered in a single dose or in divided doses.

The preparation of various compounds of the present invention is illustrated in the following Examples. The preparation of certain starting materials is illustrated in the subsequent Preparation.

EXAMPLE 1

1(a) Dimethyl 1'-deadenino-1'β-acetoxy-4',5'-dihydro-O$^{2'}$, O$^{7'}$-diacetylgriseolate 2 ml of concentrated sulfuric acid were added to a solution of 500 mg of dimethyl 6-desamino-6-hydroxy-4'β,5'-dihydro-O$^{2'}$,O$^{7'}$-diacetylgriseolate (prepared as described in Preparation 6) in 100 ml of a 4:1 by volume mixture of acetic acid and acetic anhydride, and the mixture was allowed to stand at room temperature for 14 hours in a nitrogen atmosphere. 15 g of sodium acetate were added to the reaction mixture, and the solvent was evaporated off under reduced pressure. The residue was dissolved in a saturated aqueous solution of sodium bicarbonate, and the solution was extracted three times with methylene chloride. The methylene chloride extracts were combined and dried over anhydrous magnesium sulfate. The solvent was then evaporated off under reduced pressure. The residue was purified by silica gel column chromatography eluted with a 2:1 by volume mixture of cyclohexane and ethyl acetate. Evaporation of the solvent from the second fraction to be eluted gave 292 mg of the title compound.

Nuclear Magnetic Resonance Spectrum (CDCl$_3$) δ ppm:
  2.44 [1H, doublet of doublets, J=6.4 & 14.7Hz];
  2.65 [1H, doublet of doublets, J=14.7 & 3.0Hz];
  4.98 [1H, doublet of doublets, J=2.5 & 6.4Hz];
  5.02 [1H, doublet of doublets, J=2.9 & 4.0Hz];
  5.15 [1H, doublet of doublets, J=4.0 & 2.5Hz];
  5.72 [1H, singlet];
  6.29 [1H, doublet, J=2.9Hz].

Mass spectrum (m/e): 474 (M+43).
Fast Atom Bombardment mass spectrum (m/e): 431 (M$^+$).

1(b) Dimethyl 1'-deadenino-1'α-acetoxy-4',5'-dihydro-O$^{2'}$,O$^{7'}$-diacetylgriseolate The first fraction separated from the column chromatography described in Example 1(a) was concentrated by evaporation under reduced pressure, to give 33 mg of the title compound.

Nuclear Magnetic Resonance Spectrum (CDCl$_3$) δ ppm:
  2.67 [1H, doublet of doublets, J=7.4 & 15.1Hz];
  2.98 [1H, doublet of doublets, J=15.1 & 2.9Hz];
  4.94–4.99 [2H, multiplet];
  5.05–5.07 [1H, multiplet];
  5.61 [1H, singlet];
  6.38 [1H, doublet, J=4.9Hz].

Mass spectrum (m/e): 474 (M+43).
Fast Atom Bombardment mass spectrum (m/e): 431 (M$^+$).

1(c) Dimethyl 1'-deadenino-1'β-acetoxy-4',5'-dihydro-O$^{2'}$,O$^{7'}$-dibenzoylgriseolate 2 ml of concentrated sulfuric acid were added, whilst ice-cooling, to a solution of 400 mg of dimethyl 6-desamino-6-hydroxy-4',5'-dihydro-O$^{2'}$,O$^{7'}$-dibenzoylgriseolate (prepared by a procedure similar to that described in Preparations 1–3, 5 and 7, but employing benzoyl chloride in place of acetic anhydride in Preparation 2) dissolved in 80 ml of a 4:1 by volume mixture of acetic acid and acetic anhydride, and the mixture was allowed to stand at room temperature for 14 hours. The reaction mixture was then mixed with 15 g of sodium acetate and concentrated by evaporation under reduced pressure. The residue was dissolved in a mixture of methylene chloride and a saturated aqueous sodium bicarbonate solution and extracted three times with methylene chloride. The methylene chloride extracts were combined and dried over anhydrous magnesium sulfate, and then the solvent was evaporated off under reduced pressure. The residue was purified by silica gel column chromatography, eluted with a 2:1 by volume mixture of cyclohexane and ethyl acetate, and the fractions containing the title compound were concentrated by evaporation under reduced pressure, to give 243 mg of the title compound.

Nuclear Magnetic Resonance Spectrum (CDCl$_3$) δ ppm:
  2.50–2.60 [1H, multiplet];
  2.96–3.04 [1H, multiplet];
  5.06–5.16 [2H, multiplet];
  5.48–5.52 [1H, multiplet];
  5.88 [1H, singlet];
  6.50–6.58 [1H, multiplet].

Elemental Analysis:
  Calculated for C$_{27}$H$_{26}$O$_{12}$: C, 59.78%; H, 4.83%; N, 0%.
  Found: C, 59,59%; H, 4.80%; N, 0.01%.

Mass spectrum (m/e): 585 (M+43).

EXAMPLE 2

Dimethyl 6-deamino-6-hydroxy-2-acetylamino-2-dehydro-4',5'-dihydro-O$^{2'}$,O$^{7'}$-dibenzoylgriseolate 200 mg of dimethyl 1'-deadenino-1'β-acetoxy-4',5'-dihydro-O$^{2'}$,O$^{7'}$-dibenzoylgriseolate [prepared as described in Example 1(c)] and 200 mg of bistrimethylsilyl-N$^2$-acetylguanine were placed in a two-necked flask, under an atmosphere of nitrogen. 0.4 ml of trimethylsilyl trifluoromethanesulfonate was added to a solution of the mixture dissolved in 40 ml of 1,2-dichloroethane, whilst ice-cooling, and then the mixture was allowed to stand at room temperature for 4 days. The reaction mixture was worked up in a similar manner to that described in Example 3. It was purified by silica gel column chromatography, eluted with methylene chloride containing 3% v/v of methanol, to give 54.8 mg of the title compound which was isolated from the second fraction to be eluted.

Nuclear Magnetic Resonance Spectrum [(CD$_3$)$_2$SO] δ ppm:
  2.59–2.96 [2H, multiplet];
  5.12–5.32 [1H, multiplet];
  5.32–5.63 [1H, multiplet];
  5.83 [1H, singlet];
  6.11 [1H, doublet of doublets. J=4.5 & 3.9Hz];
  6.47 [1H, doublet, J=4.5Hz];
  8.32 [1H, singlet].

Elemental Analysis:
  Calculated for C$_{32}$H$_{29}$N$_5$O$_{12}$·1/2H$_2$O: C, 56.14%; H, 4.50%; N, 10.23%.
  Found: C, 56.28%; H, 4.53%; N, 9.93%.

EXAMPLE 3

6-Desamino-6-hydroxy-2-acetylamino-2-dehydro-4',5'-dihydrogriseolic acid 40 mg of dimethyl 6-desamino-6-hydroxy-2-acetylamino- 2-dehydro-4',5'-dihydro-O$^{2'}$,O$^{7'}$-dibenzoylgriseolate (prepared as described in Example 2) were dissolved in 5 ml of a 1N aqueous solution of sodium hydroxide, whilst ice-cooling, and the mixture was allowed to stand at room temperature for 4 hours. The mixture was then adjusted to a pH value of 1 with a 1N aqueous solution of hydrochloric acid, and subjected to column chromatography using an RP-18 prepacked column (reverse phase type, Merck), eluted with water containing 5% v/v acetonitrile. The main fractions were lyophilized to afford 22.0 mg of the title compound.

Nuclear Magnetic Resonance Spectrum (D$_2$O) δ ppm:
  2.58 [1H, doublet of doublets, J=6.5 & 15.4Hz];
  2.76 [1H, doublet of doublets, J=15.4 & 1.5Hz];
  4.60–4.75 [3H, multiplet];
  5.10–5.16 [1H, multiplet];
  5.97 [1H, doublet, J=6.8Hz];
  8.20 [1H, singlet].

EXAMPLE 4

6-Deamino-6-hydroxy-2-amino-2-dehydro-4',5'-dihydrogriseolic acid 21 mg of 6-deamino-6-hydroxy-2-acetylamino-2-dehydro- 4',5'-dihydrogriseolic acid (prepared as described in Example 3) were placed in a round-bottomed flask under a nitrogen atmosphere. 10 ml of methanol containing 20% v/v ammonia were added to it. The mixture was then allowed to stand at room temperature for 1 day in a tightly stoppered vessel. The solvent was evaporated off under reduced pressure and the residue was dissolved in a 0.5N aqueous solution of hydrochloric acid. This solution was subjected to column chromatography using an RP-18 prepacked column (reverse phase type; Merck). Elution with water containing 3% v/v acetonitrile, followed by lyophilization gave 16 mg of the title compound.

Nuclear Magnetic Resonance Spectrum (D$_2$O) δ ppm:
  2.49 [1H, doublet of doublets, J=6.3 & 15.5HZ];
  2.64 [1H, doublet of doublets, J=15.5 & 1.5Hz];
  4.54–4.77 [3H, multiplet];
  5.01–5.05 [1H, multiplet];
  5.89 [1H, doublet, J=7.3Hz];
  8.00 [1H, singlet].

EXAMPLE 5

Dimethyl griseolate N$^1$-oxide 8.14 g of dimethyl griseolate (prepared as described in Preparation 1) were suspended in methanol. 6.90g of m-chloroperbenzoic were added, and the mixture was stirred at room temperature for 24 hours, The solvent was then distilled off under reduced pressure. When the solvent was almost removed, 300 ml of diethyl ether were added and lumps in the solution were pulverized with a spatula until they disappeared. The mixture was filtered, and then the residue was washed with 100 ml of diethyl ether and dried to give 7.81 g of a white powdery substance. This powder was dissolved in 200 ml of methanol and 300 ml of methylene chloride as thoroughly as possible, with heating, and then the solvent was distilled off under reduced pressure with an aspirator to reduce the volume of the remaining solution to about 50 ml. The resulting crystals were filtered off, to give 6.31 g of the title compound as white powdery crystals.

Nuclear Magnetic Resonance Spectrum [(CD$_3$)$_2$SO] δ ppm:
  3.68 [3H, singlet];
  3.78 [3H, singlet];
  4.60 [1H, doublet, J=5.0Hz];
  4.67 [1H, singlet];
  5.15 [1H, doublet, J=2.2Hz];
  5.90 [1H, doublet of doublets, J=2.2 & 5.0Hz];
  6.53 [1H, singlet];
  8.53 [1H, singlet];
  8.72 [1H, singlet].

EXAMPLE 6

Griseolic acid N$^1$-oxide 1.1 g of dimethyl griseolate N$^1$-oxide (prepared as described in Example 5) was dissolved in 15 ml of a 0.5N aqueous solution of sodium hydroxide, and the mixture was allowed to stand at room temperature for 2 hours. The pH of the resulting solution was adjusted to a value of 2.3, and then the solution was subjected to column chromatography, using an RP-8 prepacked column (Merck) and washed with water. The main fractions obtained by elution with water containing 5% v/v acetonitrile, were collected and lyophilized to give 300 mg of the title compound as a white powdery substance.

Nuclear Magnetic Resonance Spectrum [(CD$_3$)$_2$SO] δ ppm:
  4.53 [1H, singlet];
  4.61 [1H, doublet, J=5.0Hz];
  5.15 [1H, doublet, J=2.2Hz];
  5.90 [1H, doublet of doublets, J=2.2 & 5.0Hz];
  6.52 [1H, singlet];
  8.51 [1H, singlet];
  8.67 [1H, singlet].

EXAMPLE 7

Dimethyl N$^1$-p-nitrobenzyloxygriseolate 35 ml of dimethylformamide were added to 1.48 g of dimethyl griseolate N$^1$-oxide (prepared as described in Example 5) and 2.27 g of p-nitrobenzyl bromide, and the mixture was stirred at room temperature overnight. The solvent was distilled off under reduced pressure, and the residue was crystallized by the addition of diethyl ether. The mixture was then filtered, and the residue was dissolved in a mixture of ethyl acetate and a 10% w/v aqueous solution of sodium bicarbonate. The organic layer which separated was washed with water and dried over anhydrous magnesium sulfate. The drying agent was filtered off, and the solvent was distilled from the filtrate, which was then purified by silica gel column chromatography, eluted with methylene chloride containing 3% v/v methanol, to give 1.5 g of the title compound.

Nuclear Magnetic Resonance Spectrum [(CD$_3$)$_2$SO] δ ppm:
  3.65, 3.73 [together 3H, each singlet];
  4.56 [1H, doublet, J=5.0Hz];
  4.63 [1H, singlet];
  5.17 [1H, doublet, J=2.2Hz];
  5.45 [2H, singlet];
  5.87 [1H, doublet of doublets, J=2.2 & 5.0Hz];
  6.41 [1H, singlet];
  7.6–8.43 [6H, multiplet].

EXAMPLE 8

Dimethyl N$^1$-benzyloxygriseolate 5.35 g of dimethyl griseolate N$^1$-oxide (prepared as described in Example 5) and 7.6 ml of benzyl bromide were allowed to react overnight in 90 ml of dimethylformamide at room temperature. The mixture was then treated by the same procedure as described in Example 7. The resulting solution was poured into 1 litre of hexane and 0.5 litre of diethyl ether, whilst stirring. The resulting powdery substance was filtered to give 5.4 g of the title compound as a crude powder.

Nuclear Magnetic Resonance Spectrum [(CD$_3$)$_2$SO] δ ppm:
  3.64, 3.71 [together 3H, each singlet];
  4.54 [1H, doublet, J=5.0Hz];
  4.63 [1H, singlet];
  5.17 [1H, doublet, J=2.2Hz];
  5.33 [2H, singlet];
  5.83 [1H, doublet of doublets, J=2.2 & 5.0Hz];
  6.46 [1H, singlet];
  7.3–7.7 [5H, multiplet];
  8.31, 8.39 [together 1H, each singlet].

EXAMPLE 9

Dibenzhydryl 1'-deadenino-1'β-[5-amino-4-(N$^2$-p-nitrobenzyloxyamidino)imidazol- 1-yl]griseolate 0.7 g of dimethyl N$^1$-p-nitrobenzyloxygriseolate (prepared as described in Example 7) was dissolved in 6.2 ml of a 1.5N aqueous solution of sodium hydroxide, and the mixture was stirred at room temperature for 3 days. The reaction mixture was then acidified with a 3N aqueous solution of hydrochloric acid, and 20 ml of acetone and 2.5 g of diphenyldiazomethane were added. The mixture was reacted to esterify the acid at room temperature for 60 minutes, whilst stirring. At the end of this time, acetone was distilled off and 30 ml of methylene chloride were added. The organic layer which separated was washed with a 10% w/v aqueous solution of sodium bicarbonate and a saturated aqueous solution of sodium chloride. The solvent was distilled off and the residue was dissolved in 2 ml of acetone. The resulting solution was poured into 300 ml of hexane, whilst stirring. The powdery substance thus obtained was purified by silica gel column chromatography, eluted with a 1:2 by volume mixture of cyclohexane and ethyl acetate, to give 0.35 g of the title compound.

Nuclear Magnetic Resonance Spectrum [(CD$_3$)$_2$SO] δ ppm:

4.51 [1H, doublet, J=5.0Hz];
4.87 [1H, singlet];
5.07 [2H, singlet];
5.25 [1H, doublet, J=2.2Hz];
5.56 [1H, broad singlet];
6.15 [1H, singlet];
6.66, 6.72 [together 1H, each singlet];
7.15–7.4 [21H, multiplet];
7.66, 8.20 [together 2H, each doublet].

EXAMPLE 10

Dibenzhydryl 1'-deadenino-1'β-[5-amino-4-($N^2$-benzyloxyamidino)imidazol-1-yl]griseolate 5.4 g of dimethyl $N^1$-benzyloxygriseolate (prepared as described in Example 8) were dissolved in 53 ml of a 1.5N aqueous solution of sodium hydroxide, and the mixture was stirred at room temperature for 3 days. The reaction mixture was then acidified with concentrated hydrochloric acid, and then 15 g of diphenyldiazomethane and 100 ml of acetone were added and the same procedure as described in Example 9 was followed. The resulting mixture was purified by silica gel column chromatography, eluted with methylene chloride containing 1% v/v methanol, to give 3.9 g of the title compound.

Nuclear Magnetic Resonance Spectrum [$(CD_3)_2SO$] δ ppm:
4.54 [1H, doublet, J=5.0Hz];
4.90 [1H, singlet];
4.94 [2H, singlet];
5.26 [1H, doublet, J=2.2Hz];
5.59 [1H, doublet of doublets, J=2.2 & 5.0Hz];
6.20 [1H, singlet];
6.69, 6.76 [together 1H, each singlet];
7.1–7.5 [26H, multiplet].

EXAMPLE 11

1'-Deadenino-1'β-(5-amino-4-amidinoimidazol-1-yl)griseolic acid 1.05 g of dibenzhydryl 1'-deadenino-1'β-[5-amino- 4-($N^2$-benzyloxyamidino)imidazol-1-yl]griseolate (prepared as described in Example 10) was dissolved in 60 ml of acetone. 30 ml of a 1N aqueous solution of hydrochloric acid and 6 ml of Raney nickel (W-2) were added to the resulting solution, with stirring. The mixture was then stirred at room temperature for a further 60 minutes. At the end of this time, the Raney nickel was removed by filtration, the acetone was distilled off, and the residue was extracted twice with ethyl acetate. The extract was washed with water, with a 10% w/v aqueous solution of sodium bicarbonate, and then with a saturated aqueous solution of sodium chloride. The extract was then dried over anhydrous magnesium sulfate. The drying agent was filtered off and the solvent was distilled off from the filtrate to give 0.67 g of the residue. This residue was then dissolved in 20 ml of acetone and 20 ml of water and the resulting mixture was acidified with concentrated hydrochloric acid. 1 g of diphenyldiazomethane was added, and the mixture was stirred at room temperature for 60 minutes. Acetone was distilled off, and the residue was extracted twice with ethyl acetate. The extract was washed with a 10% w/v aqueous solution of sodium bicarbonate and a saturated aqueous solution of sodium chloride and dried over anhydrous magnesium sulfate, which was then filtered off. The solvent was distilled off from the filtrate, and the residue was dissolved in 10 ml of acetone. The resulting mixture was poured into 200 ml of hexane, whilst stirring. The resulting powdery substance was filtered off and the residue was purified by silica gel column chromatography, eluted with methylene chloride containing 10% v/v methanol, to give 0.15 g of benzhydryl ester of the title compound.

0.06 g of this benzhydryl ester was dissolved in 0.8 ml of anisole, and 0.8 ml of trifluoroacetic acid were added, whilst ice-cooling. 10 ml of toluene were added to the resulting mixture, and the solvent was distilled off. 5 ml of acetone and 10 ml of toluene were added to the residue and the solvent was distilled off. This procedure was repeated twice, and then the residue was dissolved in 1 ml of acetone and 20 ml of hexane were added. The resulting powdery substance was filtered off and dissolved in a 10% w/v aqueous solution of sodium bicarbonate. The pH of the resulting solution was adjusted to a value of 1.9 with a 1N aqueous solution of hydrochloric acid. The solution was purified by column chromatography using an RP-8 prepacked column (reverse phase type, Merck), eluted with water, to give 24 mg of the title compound.

Nuclear Magnetic Resonance Spectrum [$(CD_3)_2SO$] δ ppm:
4.08 [1H, singlet];
4.42 [1H, doublet, J=5.0Hz];
4.83 [1H, doublet, J=2.2Hz];
5.44 [1H, doublet of doublets, J=2.2 & 5.0Hz];
6.20 [1H, singlet];
7.67 [1H, singlet].

EXAMPLE 12

Dibenzhydryl 1'-deadenino-1'β-[5-amino-4-($N^2$-hydroxyamidino)imidazol-1-yl]griseolate 1.0 g of dibenzhydryl 1'-deadenino-1'β-[5-amino-4-($N^2$-benzyloxyamidino)imidazol-1-yl]griseolate (prepared as described in Example 10) was dissolved in 20 ml of acetic acid, and then 0.6 g of 10% w/w palladium-on-carbon were added, after replacing the air in the container with nitrogen. The mixture was then stirred at room temperature in a stream of hydrogen for 2 hours. The palladium-on-carbon was filtered off, and the solvent was distilled from the filtrate. The residue was dissolved in a mixture of 30 ml of ethyl acetate and 20 ml of a 10% w/v aqueous solution of sodium bicarbonate. The organic layer which separated was washed with water and dried over anhydrous magnesium sulfate. After filtration of the drying agent, the solvent was distilled off, and the residue was purified by silica gel column chromatography, eluted with methylene chloride containing 5% v/v methanol, to give 0.26 g of the title compound.

Nuclear Magnetic Resonance Spectrum [$(CD_3)_2SO$] δ ppm:
4.57 [1H, doublet, J=5.0Hz];
4.90 [1H, singlet];
5.27 [1H, doublet, J=2.2Hz];
5.60 [1H, doublet of doublets, J=2.2 & 5.0Hz];
6.21 [1H, singlet];
6.70, 6.76 [together 1H, each singlet];
7.2–7.6 [21H, multiplet];
8.95 [1H, singlet].

EXAMPLE 13

Dibenzhydryl 2-mercaptogriseolate 0.25 g of dibenzhydryl 1'-deadenino-1'β-[5-amino-4-($N^2$-hydroxyamidino)imidazol-1-yl]griseolate (prepared as described in Example 12) was dissolved in a mixture of 2 ml of methanol, 2 ml of pyridine and 1 ml of carbon disulfide. The mixture was allowed to react at 80° C. in a steel cylinder for 14.5 hours. The solvent was then distilled off. Toluene was added to the residue and this process was repeated. The residue was purified by silica gel column chromatography, eluted with methylene chloride containing 4% v/v methanol, to give 0.062 g of the title compound.

Nuclear Magnetic Resonance Spectrum [(CD$_3$)$_2$SO] δ ppm:
- 4.63 [1H, doublet, J=5.0Hz];
- 4.88 [1H, singlet];
- 5.26 [1H, doublet, J=2.2Hz];
- 6.03 [1H, doublet of doublets, J=2.2 & 5.0Hz];
- 6.39 [1H, singlet];
- 6.69, 6.74 [together 1H, each singlet];
- 6.9–7.5 [20H, multiplet];
- 8.24 [1H, singlet].

EXAMPLE 14

Dimethyl 1'-deadenino-1'β-(2-imino-[1,2,4]oxadiazolo-[3,2-i]purin-7-yl)griseolate hydrobromide 8.46 g of dimethyl griseolate N$^1$-oxide (prepared as described in Example 5) were suspended in 400 ml of methanol. 2.52 g of cyanogen bromide were added and the mixture was stirred at room temperature for 1.5 hours, and then stirred for a further hour after adding an additional 630 mg of cyanogen bromide. The solvent was distilled off under reduced pressure to leave a volume of about 100 ml of solution remaining. 100 ml of ethyl acetate were added and the distillation under reduced pressure was continued until the liquid volume reached 100 ml. 1000 ml of ethyl acetate were gradually added to the residual solution, whilst stirring. The suspension, containing crystals, was placed in a refrigerator overnight. The crystals were filtered off to give 9.77 g of the title compound.

Nuclear Magnetic Resonance Spectrum [(CD$_3$)$_2$SO] δ ppm:
- 3.67 [3H, singlet];
- 3.73 [3H, singlet];
- 4.67 [1H, doublet, J=5.0Hz];
- 4.66 [1H, singlet];
- 5.26 [1H, doublet, J=2.2Hz];
- 5.84 [1H, doublet of doublets, J=2.2 & 5.0Hz];
- 6.76 [1H, singlet];
- 9.07 [1H, singlet];
- 10.23 [1H, singlet].

EXAMPLE 15

Dimethyl N$^6$-cyanogriseolate N$^1$-oxide 9.77 g of dimethyl 1'-deadenino-1'β-(2-imino-[1,2,4]oxadiazolo[3,2-i]purin-7-yl)griseolate hydrobromide [prepared as described in Example 14] were dissolved in 50 ml of methanol. 50 ml of 20% v/v ammonia in methanol were added to the mixture, which was then allowed to stand at room temperature for 60 minutes. 200 ml of ethyl acetate were added to the reaction mixture and the solvent was distilled off under reduced pressure with an aspirator. When the liquid volume became about 100 ml, 200 ml of ethyl acetate were added and then distilled off under reduced pressure. When the liquid volume reached 200 ml, the resulting mixture was placed in a refrigerator overnight. The crystals thus produced in the solution were filtered off to give 8.53 g of the title compound as yellowish white fine crystals.

Nuclear Magnetic Resonance Spectrum [(CD$_3$)$_2$SO] δ ppm:
- 3.67 [3H, singlet];
- 3.74 [3H, singlet];
- 4.63 [1H, doublet, J=5.0Hz];
- 4.66 [1H, singlet];
- 5.16 [1H, doublet, J=2.2 Hz];
- 5.93 [1H, doublet of doublets, J=2.2 & 5.0Hz];
- 6.50 [1H, singlet];
- 8.33 [1H, singlet];
- 8.49 [1H, singlet].

EXAMPLE 16

Dimethyl N$^1$-benzyloxy-N$^6$-cyanogriseolate 8.53 g of dimethyl N$^6$-cyanogriseolate N$^1$-oxide [prepared as described in Example 15] were dissolved in 100 ml of dimethylformamide. 10 ml of benzyl bromide and 10 ml of triethylamine were added and the mixture was stirred at room temperature for 4 hours. The solvent was distilled off under reduced pressure. 30 ml of ethanol and 30 ml of toluene were added to the residue and then distilled off. This procedure was repeated 4 times. The oily substance thus obtained was mixed with 500 ml of diethyl ether, subjected to ultrasonic treatment, whilst stirring with a spatula, to give a pale yellow powdery substance. This substance was filtered off and dissolved in 300 ml of water and 500 ml of ethyl acetate. The organic layer which separated was washed with 100 ml each of a saturated aqueous solution of sodium chloride, a 0.2N aqueous solution of hydrochloric acid, a 10% w/v aqueous solution of sodium bicarbonate and a saturated aqueous solution of sodium chloride, in that order, and dried over anhydrous magnesium sulfate. After treatment of the solution with active carbon, the solvent was distilled off under reduced pressure to give 8.8 g of the title compound as a yellow caramel-like substance.

Nuclear Magnetic Resonance Spectrum [(CD$_3$)$_2$SO] δ ppm:
- 3.68 [3H, singlet];
- 3.76 [3H, singlet];
- 4.61 [1H, doublet, J=5.0Hz];
- 4.67 [1H, singlet];
- 5.26 [1H, doublet, J=2.2Hz];
- 5.37 [2H, singlet];
- 5.83 [1H, doublet of doublets, J=2.2 & 5.0Hz];
- 6.57 [1H, singlet];
- 7.2–7.8 [5H, multiplet];
- 8.56 [1H, singlet];
- 8.81 [1H, singlet].

EXAMPLE 17

Dimethyl N$^6$-cyano-N$^1$-methoxygriseolate 8.3 ml of triethylamine and 3.9 ml of methyl iodide were added to 40 ml of dimethylformamide containing 4.5 g of dimethyl N$^6$-cyanogriseolate N$^1$-oxide (prepared as described in Example 15), whilst ice-cooling. The mixture was stirred at room temperature for 4.5 hours. The solvent was then distilled off, and 100 ml of diethyl ether were added to the residue to yield a powder by pulverizing the mixture with a spatula. The insoluble substance was filtered off, washed with 30 ml of diethyl ether and dissolved in a mixture of 80 ml of ethyl acetate and 20 ml of water, and then the solution was extracted repeatedly with ethyl acetate. The ethyl acetate layer was dried over anhydrous magnesium sulfate. After filtering off the drying agent, the solvent was distilled off, to give 3 g of the title compound.

Nuclear Magnetic Resonance Spectrum [(CD$_3$)$_2$SO] δ ppm:
- 3.60, 3.73 [together 3H, each singlet];
- 4.14 [3H, singlet];
- 4.58 [1H, doublet, J=5.0Hz];
- 4.64 [1H, singlet];
- 5.21 [1H, doublet, J=2.2Hz];
- 5.83 [1H, doublet of doublets, J=2.2 & 5.0Hz];
- 6.55 [1H, singlet];
- 8.53, 8.93 [together 1H, each singlet].

EXAMPLE 18

2-Amino-N$^6$-benzyloxygriseolic acid 100 ml of a 0.2N aqueous solution of sodium hydroxide were added to 400 ml of methanol containing 8.8 g of dimethyl $N^1$-benzylox $N^6$-cyanogriseolate (prepared as described in Example 16), whilst stirring. The reaction solution was adjusted to a pH value of 12–12.5 by the addition of a 1N aqueous solution of sodium hydroxide, and it was then allowed to stand at room temperature for 60 minutes. The solvent was distilled off until the remaining liquid volume reached about 100 ml. The resulting solution was mixed with 50 ml of water and 150 ml of ethanol and heated under reflux for 2 hours. The solvent was then distilled off again under reduced pressure until the liquid volume was reduced to about 100 ml. 100 ml of a 2N aqueous solution of sodium hydroxide were added, and the resulting solution was allowed to stand at room temperature for 60 minutes. 200 ml of ethyl acetate were added to the solution, and the pH value was adjusted to 0.5 with concentrated hydrochloric acid, whilst stirring. The aqueous and organic layers were separated, and the organic layer was washed with 50 ml of a 0.1N aqueous solution of hydrochloric acid, and then combined with the aqueous layer and treated with active carbon. The pH of the solution was adjusted to 2.3 by then addition of solid sodium bicarbonate with vigorous stirring. The insoluble precipitate resulting in the solution was placed in a refrigerator overnight. The resulting powdery substance was filtered off and dried, to give 5.29 g of the title compound as a yellowish white powder.

Nuclear Magnetic Resonance Spectrum $[(CD_3)_2SO]$ δ ppm:
 4.54 [1H, singlet];
 4.55 [1H, doublet, J=5.0Hz];
 5.06 [2H, singlet];
 5.08 [1H, doublet, J=2.2Hz];
 5.83 [1H, doublet of doublets, J=2.2 & 5.0Hz];
 6.27 [1H, singlet];
 7.2–7.6 [5H, multiplet];
 7.79 [1H, singlet].

EXAMPLE 19

2-Amino-$N^6$-methoxygriseolic acid 50 ml of a 0.2N aqueous solution of sodium hydroxide were added to 70 ml of methanol containing 3 g of dimethyl $N^6$-cyano-$N^1$-methoxygriseolate (prepared as described in Example 17). The resulting mixture was stirred at room temperature for 1.5 hours and then its pH value was adjusted to 11.7 with 2 ml of a 1N aqueous solution of sodium hydroxide, and the mixture was stirred for further 30 minutes. The solution was adjusted to a pH value of 7.0 with concentrated hydrochloric acid and methanol was distilled off. The remaining solution was mixed with 70 ml of ethanol and heated for 1.5 hours under reflux. The solvent was distilled off until about 50 ml of the solution remained, and the resulting solution was mixed with 50 ml of a 1N aqueous solution of sodium hydroxide and stirred at room temperature for 60 minutes. The resulting mixture was adjusted to a pH value of 1 with concentrated hydrochloric acid and then washed with ethyl acetate. The aqueous layer was adjusted to a pH value of 2.3 with a 10% w/v aqueous solution of sodium bicarbonate. It was then purified by column chromatography using an RP-8 prepacked column (reverse phase type Merck), eluted with an aqueous solution containing 5% v/v acetonitrile and 0.02% v/v acetic acid, to give 1.91 g of the title compound.

Nuclear Magnetic Resonance Spectrum $[(CD_3)_2SO]$ δ ppm:
 3.77 [3H, singlet];
 4.51 [1H, singlet];
 4.54 [1H, doublet, J=5.0Hz];
 5.07 [1H, doublet, J=2.2Hz];
 5.87 [1H, doublet of doublets, J=2.2 & 5.0Hz];
 6.26 [1H, singlet];
 7.77 [1H, singlet].

EXAMPLE 20

2-Amino-$N^6$-hydroxygriseolic acid 200 mg of 2-amino-$N^6$-benzyloxygriseolic acid (prepared as described in Example 18) were heated with 20 ml of methanol and 20 ml of water. The solution was then allowed to stand at room temperature, whilst ice-cooling. 50 mg of 10% w/w palladium-on-carbon were added and the mixture was stirred under a stream of hydrogen. Since the reaction solution became turbid due to the production of a white substance in about 30 minutes, it was clarified with 5 ml of a 1N aqueous solution of hydrochloric acid and the resulting solution was stirred for 1.5 hours. The catalyst was removed by filtration, methanol was distilled off under reduced pressure, and the pH of the solution was adjusted to 2.2 by adding a saturated aqueous solution of sodium bicarbonate, whilst stirring. The reaction mixture was allowed to stand in an ice-bath for 30 minutes, and the resulting yellowish solid was filtered off, to give 100 mg of the title compound.

Nuclear Magnetic Resonance Spectrum $[(CD_3)_2SO]$ δ ppm:
 4.54 [1H, singlet];
 4.57 [1H, doublet, J=5.0Hz];
 5.11 [1H, doublet, J=2.2Hz];
 5.95 [1H, doublet of doublets, J=2.2 & 5.0Hz];
 6.31 [1H, singlet];
 7.83 [1H, singlet].

EXAMPLE 21

Dimethyl 2-amino-$N^6$-benzyloxygriseolate 5.4 g of dimethyl $N^1$-benzyloxy-$N^6$-cyanogriseolate (prepared as described in Example 16) were dissolved in 100 ml of methanol. 100 ml of a 0.25M phosphate buffer solution were added and the mixture was heated for 4 hours under reflux. Crystals deposited when the methanol was distilled off. When methanol was almost distilled off, the pH value of the solution was adjusted to 9 with a 10% w/v aqueous solution of sodium bicarbonate. The mixture was treated with ultrasonic waves for 15–20 minutes, and the resulting crystals were filtered off and dried to give 2.14 g of the title compound. Then the mother liquor was adjusted to a pH value of 11 with a 2N aqueous solution of sodium hydroxide, and allowed to stand at room temperature overnight. The pH value of the resulting solution was adjusted to 0.1 with concentrated hydrochloric acid, and the solution was treated with active carbon, adjusted to a pH value of 2.3 with a 2N aqueous solution of sodium hydroxide and allowed to stand at 5° C. overnight. The deposited substance was filtered off, to give 2.0 g of the title compound of Example 18.

Nuclear Magnetic Resonance Spectrum $[(CD_3)_2SO]$ δ ppm:
 3.63, 3.69 [together 3H, each singlet];
 4.51 [1H, doublet, J=5.0Hz];
 4.62 [1H, singlet];
 5.03 [2H, singlet];
 5.09 [1H, doublet, J=2.2Hz];
 5.83 [1H, doublet of doublets, J=2.2 & 5.0Hz];
 6.23 [1H, singlet];
 7.2–7.6 [5H, multiplet];
 7.70 [1H, singlet].

EXAMPLE 22

2-Aminogriseolic acid 100 mg of 2-amino-$N^6$-benzyloxygriseolic acid (prepared as described in Example 18) were dissolved in a mixture of 20 ml of a 1N solution of hydrochloric acid and 20 ml of acetone. 1 ml of Raney nickel (W-2) was added, and the mixture was stirred at room temperature for 2.5 hours. The Raney nickel was filtered off, and the pH value of the reaction mixture was adjusted to 2.3. It was then purified by column chromatography using an RP-8 prepacked column (Merck), eluted with a 3% v/v aqueous solution of acetonitrile. The main fraction was lyophilized to give 12 mg of the title compound as a white powder.

Nuclear Magnetic Resonance Spectrum [$(CD_3)_2SO$] δ ppm:
  4.46 [1H, singlet];
  4.55 [1H, doublet, J=5.0Hz];
  5.02 [1H, doublet, J=2.2Hz];
  5.87 [1H, doublet of doublets, J=2.2 & 5.0Hz];
  6.28 [1H, singlet];
  7.90 [1H, singlet].

Thin layer chromatography (Ratio of the Rf value to that of griseolic acid, taken as 1.0).
  Silica gel plate (Merck):
  0.80 (developing solvent, water: methanol: acetonitrile= 70:15:15 by volume).
  Plate RP-8 for reverse phase:
  0.79 (developing solvent, water containing 2% v/v acetonitrile and 0.02% v/v acetic acid).

EXAMPLE 23

Dibenzhydryl-amino-$N^6$-benzyloxygriseolate 1.0 g of 2-amino-$N^6$-benzyloxygriseolic acid (prepared as described in Example 18) was suspended in 100 ml of acetone and 100 ml of water. Diphenyldiazomethane was added until no further disappearance of its red color was observed. The reaction mixture was then stirred during the addition of 4 ml of a 1N aqueous solution of hydrochloric acid; and diphenyldiazomethane was added again until no further disappearance of its red color could be observed. The mixture was then stirred for 60 minutes. Acetone was removed by distillation under reduced pressure and water was removed by decantation. The residue was dissolved in a mixture of 50 ml of ethyl acetate and 50 ml of water, and the organic layer was washed with 30 ml of a 5% w/v aqueous solution of sodium bicarbonate and 30 ml of a saturated aqueous solution of sodium chloride and then dried over anhydrous magnesium sulfate. The solvent was distilled off under reduced pressure and the residue was dissolved in 30 ml of ethyl acetate, and the resulting solution was poured into 500 ml of hexane, whilst stirring. The resulting insoluble substance was collected by filtration and purified using a silica gel prepacked chromatography column (Merck) and an eluent consisting of methylene chloride containing 2.5% v/v methanol. Of the two main fractions, the fraction eluted later was collected, evaporated to dryness and lyophilized from benzene, to give 430 mg of the title compound as a white powder.

Nuclear Magnetic Resonance Spectrum [$(CD_3)_2SO$] δ ppm:
  4.63 [1H, doublet, J=5.0Hz];
  4.99 [1H, singlet];
  5.07 [2H, singlet];
  5.31 [1H, doublet, J=2.2Hz];
  5.97 [1H, doublet of doublets, J=2.2 & 5.0Hz];
  6.33 [1H, singlet];
  6.75 [1H, singlet];
  6.81 [1H, singlet];
  7.74 [1H, singlet].

EXAMPLE 24

Dibenzhydryl-amino-$N^6$-benzyloxy-$N^6$-benzhydrylgriseolate

Following the same procedure as described in Example 23, the reaction mixture was purified by silica gel column chromatography. The first main fraction was collected, evaporated to dryness and lyophilized from benzene to give 420 mg of the title compound.

Nuclear Magnetic Resonance Spectrum [$(CD_3)_2SO$] δ ppm:
  4.53 [2H, broad singlet];
  4.72 [1H, doublet, J=5.0Hz];
  4.96 [1H, singlet];
  5.31 [1H, doublet, J=2.2Hz];
  6.10 [1H, doublet, J=2.2 & 5.0Hz];
  6.46 [1H, singlet];
  6.75 [1H, singlet];
  6.82 [1H, singlet];
  7.69 [1H, singlet];
  8.13 [1H, singlet].

EXAMPLE 25

Dibenzhydryl 2-aminogriseolate 83 mg of dibenzhydryl 2-amino-$N^6$-benzyloxygriseolate (prepared as described in Example 23) were dissolved in a mixture of 20 ml of acetone and 10 ml of a 1N aqueous solution of hydrochloric acid. 1 ml of Raney nickel (W-2) was added to the mixture, which was then stirred vigorously at room temperature for 45 minutes. The Raney nickel was removed by filtration, and the solvent was distilled off under reduced pressure until acetone could be no longer smelled. The resulting mixture was mixed with 30 ml of ethyl acetate and separated. The organic layer was washed with 20 ml of a 10% w/v aqueous solution of sodium bicarbonate and 20 ml of a saturated aqueous solution of sodium chloride, and dried over anhydrous magnesium sulfate. The solvent was distilled off under reduced pressure, and the residue was purified using a prepacked silica gel chromatography column (Merck) and an eluent consisting of methylene chloride containing 5% v/v methanol. The main fraction was collected and lyophilized from benzene to give 73 mg of the title compound as a white powder.

Nuclear Magnetic Resonance Spectrum [$(CD_3)_2SO$] δ ppm:
  4.67 [1H, doublet, J=5.0Hz];
  4.92 [1H, singlet];
  5.27 [1H, doublet, J=2.2Hz];
  6.03 [1H, doublet of doublets, J=2.2 & 5.0Hz];
  6.37 [1H, singlet];
  6.73 [1H, singlet];
  6.77 [1H, singlet];
  7.97 [1H, singlet].

EXAMPLE 26

2-Aminogriseolic acid 0.56 g of dibenzhydryl 2-aminogriseolate (prepared as described in Example 25) was suspended in 5 ml of anisole and solubilized by adding 5 ml of trifluoroacetic acid, whilst ice-cooling, and the mixture was allowed to stand at room temperature for 10–15 minutes. 15 ml of toluene were added to the reaction mixture and then the solvent was distilled off. The procedure comprising the addition of a mixed solvent of 5 ml of acetone and 15 ml of toluene and its removal by distillation was repeated twice and the residue was suspended in 2 ml of acetone. The resulting suspension was poured into 200 ml of hexane, whilst stirring. The resulting powdery substance was filtered off and dissolved in a 10% w/v aqueous solution of sodium bicarbonate. The pH value of the resulting solution was adjusted to a value of 0.6 with concentrated hydrochloric acid, and the solution was treated with active carbon. The pH value of the resulting mixture was adjusted to 2 with a 10% w/v aqueous solution of sodium bicarbonate, and the mixture was allowed to stand at 5° C. overnight. The deposited crystals were filtered off and dried, to give 0.15 g of the title compound. The mother liquor was purified by reverse phase column chromatography using an RP-8 prepacked column (Merck), eluted with a 3% v/v aqueous solution of acetonitrile, to give 0.04 g of the title compound, whose properties were the same as those of the product of Example 22.

EXAMPLE 27

Dibenzhydryl 2-hydroxygriseolate 0.6 g of dibenzhydryl 2-aminogriseolate (prepared as described in Example 25) was dissolved in 50 ml of 80% v/v aqueous acetic acid. After replacing the air in the container with nitrogen, 1 g of sodium nitrite was added to the mixture, whilst ice-cooling, and the mixture was allowed to react at room temperature for 1.5 hours. The solvent was distilled off, and the residue was mixed with water and the water was distilled off again. The deposited substance was suspended in water and collected by filtration. The residue was dissolved in 15 ml of acetone and the pH value of the solution was adjusted to 9–10 by the addition of concentrated aqueous ammonia. The resulting solution was allowed to stand at room temperature for 20 minutes and then the acetone was distilled off. The residue was mixed with 50 ml of ethyl acetate and 50 ml of water and stirred thoroughly. The resulting precipitate was filtered off and purified by silica gel column chromatography (eluted with 10% v/v methanol in methylene chloride) to give 0.35 g of the title compound. The separated ethyl acetate layer was washed with a 10% w/v aqueous solution of sodium bicarbonate and a saturated aqueous solution of sodium chloride and dried over anhydrous magnesium sulfate. The drying agent was removed by filtration and the solvent was distilled off. The resulting residue was purified by silica gel column chromatography, using methylene chloride containing 10% v/v methanol as the eluent, to give 0.04 g of the title compound.
Nuclear Magnetic Resonance Spectrum [$(CD_3)_2SO$] δ ppm:
  4.59 [1H, doublet, J=5.0Hz];
  4.90 [1H, singlet];
  5.25 [1H, doublet, J=2.2Hz];
  6.05 [1H, doublet of doublets, J=2.2 & 5.0Hz];
  6.30 [1H, singlet];
  6.67, 6.73 [together 1H, each singlet];
  7.0–7.5 [20H, multiplet];
  7.93 [1H, singlet].

EXAMPLE 28

Dibenzhydryl 6-desamino-2,6-dihydroxygriseolate

In the procedure described in Example 27, the deposited substance filtered off from the mixture of ethyl acetate and water was subjected to silica gel column chromatography. First, the title compound of Example 27 was eluted with 10% v/v methanol in methylene chloride; a subsequent fraction was eluted with methanol to give 0.06 g of the title compound.
Nuclear Magnetic Resonance Spectrum [$(CD_3)_2SO$] δ ppm:
  4.47 [1H, doublet, J=5.0Hz];
  4.85 [1H, singlet];
  5.19 [1H, doublet, J=2.2Hz];
  6.04 [1H, doublet of doublets, J=5.0 & 2.2Hz];
  6.22 [1H, singlet];
  6.65, 6.73 [together 1H, each singlet];
  7.15–7.45 [20H, multiplet];
  7.56 [1H, singlet].

EXAMPLE 29

2-Hydroxygriseolic acid 0.37 g of dibenzhydryl 2-hydroxygriseolate (prepared as described in Example 27) was dissolved in 3 ml of anisole. 3 ml of trifluoroacetic acid were added, whilst ice-cooling and the mixture was allowed to stand at room temperature for 10 minutes. Toluene was then added and then the solvent was distilled off. A mixture of acetone and toluene was then added and subsequently distilled off. This procedure was repeated twice and the resulting mixture was suspended in 2 ml of acetone and poured into 100 ml of hexane, whilst stirring. The deposited substance was collected by filtration. The residue was dissolved in a 10% w/v aqueous solution of sodium bicarbonate and the solution was adjusted to a pH value of 1.2 with concentrated hydrochloric acid. The resulting mixture was purified by column chromatography using an RP-8 prepacked column (Merck), eluted with water, to give 0.17 g of the title compound.
Nuclear Magnetic Resonance Spectrum [$(CD_3)_2SO$] δ ppm:
  4.46 [1H, singlet];
  4.47 [1H, doublet, J=5.0Hz];
  5.05 [1H, doublet, J=2.2Hz];
  5.89 [1H, doublet of doublets, J=2.2 & 5.0Hz];
  6.24 [1H, singlet):
  7.95 [1H, singlet].
Thin layer chromatography (Ratio of the Rf value to that of griseolic acid, taken as 1.0):
  Plate RP-8 for reverse phase (Merck)
  1.32 (developing solvent: water containing 2% v/v acetonitrile and 0.02% v/v acetic acid).

EXAMPLE 30

6-Desamino-2,6-dihydroxygriseolic acid 40 mg of dibenzhydryl 6-desamino-2,6-dihydroxygriseolic acid (prepared as described in Example 28) were dissolved in 1 ml or anisole. 1 ml of trifluoroacetic acid was added, whilst ice-cooling, and the mixture was allowed to stand at room temperature for 10–15 minutes. The procedure of adding and distilling off toluene and then adding and distilling off a mixture of acetone and toluene was repeated twice, and the residue was suspended in 0.5 ml of acetone. After the addition of 20 ml of hexane, the deposited substance was collected by filtration. The residue was dissolved in a 10% w/v aqueous solution of sodium bicarbonate. The solution was adjusted to a pH value of 0.6 with concentrated hydrochloric acid. The resulting solution was purified by column chromatography using an RP-8 prepacked column (reverse phase type Merck), eluted with water, to give 25 mg of the title compound.
Nuclear Magnetic Resonance Spectrum [$(CD_3)_2SO$] δ ppm:
  4.49 [1H, singlet];
  4.58 [1H, doublet, J=5.0Hz];
  5.12 [1H, doublet, J=2.2Hz];
  5.53 [1H, doublet of doublets, J=2.2 & 5.0Hz];
  6.41 [1H, singlet];
  7.91 [1H, singlet].
Thin layer chromatography (Ratio of the Rf value to that of griseolic acid, taken as 1.0):
  Silica gel plate (Merck)
  0.57 (developing solvent: water: methanol: acetonitrile= 70:15:15 by volume):
  Plate RP-8 for reverse phase (Merck)
  1.65 (developing solvent: water containing 2% v/v acetonitrile and 0.02% v/v acetic acid).

EXAMPLE 31

Dimethyl $N^6$-benzyloxy-2-(N',N'-dimethylaminomethylene)aminogriseolate 528 mg of dimethyl 2-amino-$N^6$-benzyloxygriseolate (prepared as described in Example 21) were dissolved in 10 ml of dimethylformamide. 0.24 ml of dimethylformamide dimethylacetal was added, and the mixture was allowed to stand at room temperature for 2 hours. After the disappearance of the starting substance had been confirmed by thin layer chromatography, the solvent was distilled off under reduced pressure. The residue was dissolved in 40 ml of methylene chloride and 40 ml of water, and the organic layer was washed with 20 ml of a saturated aqueous solution of sodium chloride. All the aqueous layers were combined and then mixed with 2 ml of a 5% w/v aqueous solution of sodium bicarbonate and extracted with 20 ml of methylene chloride twice. The organic layers were combined, dried over anhydrous magnesium sulfate and the solvent was distilled off under reduced pressure. The residue was subjected to silica gel column chromatography (Merck), eluted with methylene chloride containing 3% v/v methanol. After purification, the substance obtained was lyophilized from benzene to give 322 mg of the title compound as a white powder.

Nuclear Magnetic Resonance Spectrum [$(CD_3)_2SO$] δ ppm:
  3.04 [3H, singlet];
  3.19 [3H, singlet];
  3.67 [3H, singlet];
  3.72 [3H, singlet];
  4.47 [1H, doublet, J=5.0Hz];
  4.63 [1H, singlet];
  5.01 [2H, singlet];
  5.12 [1H, doublet, J=2.2Hz];
  6.00 [1H, doublet of doublets, J22.2 & 5.0Hz];
  6.38 [1H, singlet];
  7.2–7.6 [5H, multiplet];
  7.83 [1H, singlet];
  8.50 [1H, singlet].

EXAMPLE 32

Dimethyl 2-(N',N'-dimethylaminomethylene)aminogriseolate 583 mg of dimethyl $N^6$-benzyloxy-2-(N',N'-dimethylaminomethylene)aminogriseolate (prepared as described in Example 31) were dissolved in 100 ml of acetone and 75 ml of 1N hydrochloric acid. 10 ml of Raney nickel (W-2) suspended in water were added, and the resulting mixture was stirred at room temperature for 30 minutes keeping the pH not less than 1.0, and monitoring with a pH meter. The Raney nickel was removed by filtration and the filtrate was condensed by evaporation under reduced pressure. When the acetone was almost completely removed, the resulting mixture was mixed with 200 ml of methylene chloride and neutralized with an aqueous sodium bicarbonate solution, and the resulting insoluble substance was removed by filtration. After separation of the organic layer, the aqueous layer was extracted 3 times, each time with 50 ml of methylene chloride. The organic layers were combined and dried over anhydrous magnesium sulfate. The solvent was distilled off under reduced pressure and the residue was subjected to silica gel column chromatography (Merck), eluted with methylene chloride containing 5% v/v methanol. The substance obtained was purified and lyophilized from benzene, to give 180 mg of the title compound as a white powder.

Nuclear Magnetic Resonance Spectrum [$(CD_3)_2SO$] δ ppm:
  3.04 [3H, singlet];
  3.15 [3H, singlet];
  3.67 [3H, singlet];
  3.73 [3H, singlet];
  4.53 [1H, doublet, J=5.0Hz];
  4.64 [1H, singlet];
  5.13 [1H, doublet, J=2.2Hz];
  6.06 [1H, doublet of doublets, J=2.2 & 5.0Hz];
  6.47 [1H, singlet];
  7.33 [1H, singlet].

EXAMPLE 33

Dimethyl 6-desamino-2-(N',N'-dimethylaminomethylene)-amino- 6-hydroxygriseolate 477 mg of dimethyl 2-(N',N'-dimethylaminomethylene)aminogriseolate (prepared as described in Example 32) were dissolved in 50 ml of 80% v/v aqueous acetic acid. 1.34 g of sodium nitrite were added, whilst ice-cooling, and the mixture was allowed to stand at room temperature for 17 hours. After the disappearance of the starting substance had been confirmed by thin layer chromatography, the solvent was distilled off under reduced pressure. Ethanol was added and then distilled off, and this addition and distillation of ethanol was repeated until acetic acid could no longer be smelled. The residue was dissolved in a mixture of 50 ml of methylene chloride, 20 ml of water and 5 ml of a 5% w/v aqueous solution of sodium bicarbonate. The organic layer was separated and extracted 3 times, each time with 30 ml of methylene chloride, and the extracts were combined. The solvent was distilled off under reduced pressure. The residue was purified using a prepacked silica gel chromatography column (Merck), eluted with methylene chloride containing 10% v/v methanol. The main fractions were collected and lyophilized from benzene, to give 310 mg of the title compound as a white powder.

Ultraviolet Absorption Spectrum (methanol) $\lambda_{max}$:
  Acidic: 292 nm
  Neutral: 300 nm
  Basic: 279 nm

EXAMPLE 34

2-Amino-6-desamino-6-hydroxygriseolic acid 130 mg of dimethyl 6-desamino-2-(N',N'-dimethylaminomethylene)amino- 6-hydroxygriseolate (prepared as described in Example 33) were dissolved in 20 ml of concentrated aqueous ammonia, and the mixture was allowed to stand at room temperature for 3 hours. The solution was evaporated to dryness under reduced pressure, and the residue was dissolved in 10 ml of water. The resulting solution was adjusted to a pH value of 2.3, and then subjected to chromatography using an RP-8 prepacked chromatography column (Merck), which was washed with water and eluted with water containing 5% v/v acetonitrile. The main fractions were collected and lyophilized, to give 67 mg of the title compound as a white powder.

Ultraviolet Absorption Spectrum ($H_2O$) $\lambda_{max}$:
  Acidic: 255 nm, 273 (shoulder)nm.
  Neutral: 253 nm, 278 (shoulder)nm.
  Basic: 264 nm.

Nuclear Magnetic Resonance Spectrum [$(CD_3)_2SO$] δ ppm:
  4.48 [1H, singlet];
  4.53 [1H, doublet, J=4.9Hz];
  5.07 [1H, doublet, J=2.4Hz];
  5.79 [1H, doublet of doublets, J=2.4 & 4.9Hz];
  6.25 [1H, singlet];
  7.87 [1Ho singlet].

Thin layer chromatography (Ratio of Rf value to that of griseolic acid, taken as 1.0):
  Silica gel plate (Merck)

0.80 (developing solvent: water: methanol: acetonitrile= 70:15:15 by volume);
Plate RP-8 for reverse phase (Merck)
1.44 (developing solvent: water containing 2% v/v acetonitrile and 0.02% v/v acetic acid).

EXAMPLE 35

Methyl 2-amino-6-desamino-6-hydroxygriseolate 418 mg of silver perchlorate were added to a suspension of 400 mg of 2-amino-6-desamino-6 -hydroxygriseolic acid (prepared as described in Example 34) in 40 ml of methanol, and 0.187 ml of methyl iodide was added to the resulting mixture, whilst stirring at room temperature. The mixture was stirred continuously at room temperature for a further 2.5 hours, and then a further 0.126 ml of methyl iodide was added. The resulting mixture was stirred for a further 8 hours and was then placed in a refrigerator overnight. The insolubles which separated were filtered off and the methanol was distilled off under reduced pressure. The residue was dissolved in water and the resulting solution was adjusted to a pH value of 1.38 with concentrated aqueous hydrochloric acid and purified by column chromatography through an RP-8 prepacked column (Merck), using water containing 5% v/v acetonitrile as the eluent. The resultant main fraction was freeze-dried, to give 170 mg of the title compound as a white powdery substance.

Ultraviolet Absorption Spectrum ($H_2O$) $\lambda_{max}$:
  Acidic: 257.5 nm, 280 (shoulder)nm.
  Neutral: 253.5 nm, 275 (shoulder)nm.
  Basic: 265 nm.
Nuclear Magnetic Resonance Spectrum [$(CD_3)_2SO$] δ ppm:
  4.53 [1H, doublet, J=5.4 Hz];
  4.59 [1H, singlet];
  5.09 [1H, doublet, J=2.0 Hz];
  5.80 [1H, doublet of doublets, J=2.0 & 5.4Hz];
  6.25 [1H, singlet];
  7.88 [1H, singlet].

EXAMPLE 36

2-Amino-6-desamino-6-hydroxygriseolic acid monoamide

A solution of 120 mg of methyl 2-amino-6-desamino-6-hydroxygriseolate (prepared as described in Example 35) in 20 ml of 20% v/v methanolic ammonia was allowed to stand overnight. The solvent was then distilled off under reduced pressure, and the residue was dissolved in 3 ml of a 1N aqueous solution of sodium hydroxide. The resultant solution was adjusted to a pH value of 1.8–1.9 by the addition of concentrated aqueous hydrochloric acid, whilst ice-cooling, to form a gel-like substance in situ. This was then dissolved in about 20 ml of water by adjusting the pH value to 0.5. The resultant solution was then adjusted to a pH value of 1.0 by the addition of an aqueous solution of sodium bicarbonate. The insolubles were then filtered off, and the residue was purified by column chromatography through an RP-8 prepacked column (Merck) using water containing 5% v/v acetonitrile as the eluent. The main traction was freeze-dried, to give 79 mg of the title compound.

Ultraviolet Absorption Spectrum ($H_2O$): $\lambda_{max}$ nm (ε)
  Acidic: 257 (12100), 280 (shoulder) (8400).
  Neutral: 252 (13700), 277 (shoulder) (8800).
  Basic: 264 (12400).
Nuclear Magnetic Resonance Spectrum [$(CD_3)_2SO$] δ ppm:
  4.32 [1H, singlet];
  4.50 [1H, doublet, J=4.9Hz];
  8.05 [1H, doublet, J=2.0Hz];
  5.80 [1H, doublet of doublets, J=2.4 & 4.9Hz];
  6.24 [1H, singlet];
  7.78 [1H, singlet].

EXAMPLE 37

$N^6$-Methyl-7'-desoxy-4'α,5'-dihydrogriseolic acid 1 ml of methyl iodide was added to a solution of 100 mg of 7'-desoxy-4'α,5'-dihydrogriseolic acid in 20 ml of dimethylformamide, and the mixture was allowed to stand at room temperature for 24 hours in a sealed vessel. The solvent was distilled off under reduced pressure to give a residue. 10 ml each of acetone and toluene were added to the residue and the mixture was concentrated by evaporation under reduced pressure. This operation was repeated twice. A solution of the resulting residue in 20 ml of a 0.5M phosphate buffer of pH 7.0 was stirred for 3 hours under reflux, to give a reaction mixture which was purified by column chromatography using an RP-8 prepacked column (Merck) followed by lyophilizing the main fractions to give 67 mg of the title compound as a white powder.

Ultraviolet Absorption Spectrum (ε) $\lambda_{max}$:
  pH 1.0 262 nm (17700).
  $H_2O$ 264 nm (16700).
  pH 13 266 nm (17100).
Nuclear Magnetic Resonance Spectrum [$(CD_3)_2SO+D_2O$] δ ppm:
  2.28–2.31 (2H, multiplet);
  2.80–3.03 (5H, multiplet):
  4.37–4.46 (3H, multiplet):
  6.16 (1H, singlet):
  8.26 (1H, doublet);
  8.28 (1H, singlet).

PREPARATION 1

Dimethyl griseolate 700 mg of griseolic acid were dissolved in 100 ml of dimethylformamide and ice-cooled. A solution of 1.0–1.2 mmole of diazomethane in 1 ml of diethyl ether was added, whilst stirring, to the solution until yellow color indicated the presence of diazomethane. The mixture was then allowed to stand for 10 minutes. Acetic acid was added to decompose the excess diazomethane and was then stripped off by evaporation under reduced pressure to give a residue. The residue was dissolved in methanol and insolubles were filtered off. The filtrate was evaporated under reduced pressure to give a residue, which was recrystallized from water to yield 540 mg of the title compound.

Ultraviolet Absorption Spectrum (methanol) $\lambda_{max}$ nm:
  258 (ε=15600).
Nuclear Magnetic Resonance Spectrum [$(CD_3)_2SO$] δ ppm:
  4.60 [1H, doublet, J=6.0Hz];
  4.66 [1H, singlet];
  5.12 [1H, doublet, J=3.0Hz];
  6.06 [1H, doublet of doublets, J=3.0 & 6.0Hz];
  6.53 [1H, singlet];
  8.33 [1H, singlet];
  8.37 [1H, singlet].

PREPARATION 2

Dimethyl $O^{2'}$, $O^{7'}$-diacetylgriseolate

In a round-bottomed flask, 10 g of dimethyl griseolate (prepared as described in Preparation 1) were dissolved in 150 ml of pyridine, and 33 ml of acetic anhydride were added, whilst ice-cooling. The mixture was allowed to stand at room temperature for 2 hours. At the end of this time, 15 ml of water were added to the reaction mixture, whilst ice-cooling, and the solvent was evaporated off under reduced pressure. The residue was dissolved in 400 ml of methylene chloride, and the resulting solution was washed with 400 ml of a 1N aqueous solution of hydrochloric acid, 400 ml of water and 400 ml of a saturated aqueous solution of sodium bicarbonate, in that order. The solution was then extracted twice with methylene chloride. The methylene chloride extracts were dried over anhydrous magnesium sulfate, and the solvent was stripped off under reduced pressure, to give 6.70 g of the title compound as crystals.
Nuclear Magnetic Resonance Spectrum [$(CD_3)_2SO$] δ ppm:
  5.17 [1H, doublet, J=3.0Hz];
  5.66 [1H, doublet, J=6.0Hz];
  5.73 [1H, singlet];
  6.31 [1H, doublet of doublets, J=3.0 & 6.0Hz];
  6.89 [1H, singlet];
  8.23 [1H, singlet];
  8.36 [1H, singlet].

PREPARATION 3

Dimethyl $O^{2'},O^{7'}$-diacetyl-6-desamino-6-hydroxygriseolate 2.55 g of sodium nitrite were added to a solution of 1.82 g of dimethyl $O^{2'},O^{7'}$-diacetylgriseolate (prepared as described in Preparation 2) in a 80% v/v aqueous solution of acetic acid, whilst ice-cooling, and the mixture was allowed to stand for 16 hours in a tightly stoppered vessel. Thin layer chromatography at this stage showed that the starting material remained in the reaction mixture. A further 1 g of sodium nitrite was added and the mixture was allowed to stand for 3 hours. The residue obtained by evaporation of the solvent under reduced pressure was dissolved in acetone. Toluene was added to the mixture and it was then distilled off. This process was repeated three times.

The residue was dissolved in a mixture of water and chloroform. The organic layer was washed with an aqueous solution of sodium bicarbonate and a saturated aqueous solution of sodium chloride and then dried over anhydrous magnesium sulfate. Evaporation of the solvent gave a pale brown glass-like substance. This substance was purified by silica gel column chromatography and then dissolved in a small quantity of acetone. An appropriate amount of benzene was added to the solution and the mixture was allowed to stand. The resulting white crystals were collected by filtration, to give 1.28 g of the title compound as fine white crystals.
Nuclear Magnetic Resonance Spectrum [$(CD_3)_2SO$] δ ppm:
  5.22 [1H, doublet, J=3.0Hz];
  5.62 [1H, doublet, J=6.0Hz];
  5.73 [1H, singlet];
  6.13 [1H, doublet of doublets, J=3.0 & 6.0Hz];
  6.88 [1H, singlet];
  8.18 [1H, singlet];
  8.34 [1H, singlet].

PREPARATION 4

6-Desamino-6-hydroxygriseolic acid

A solution of 5.31 g of griseolic acid in 80% v/v aqueous acetic acid was prepared by heating and was then cooled to room temperature. 9.60 g of sodium nitrite were added to the mixture, under a nitrogen atmosphere. The mixture was allowed to stand for 16 hours in a tightly stoppered vessel. The solvent of the mixture was stripped off by evaporation under reduced pressure to yield a residue. Ethanol was added to this residue and then distilled off. This process was repeated until the mixture no longer smelled of acetic acid. The residue was dissolved in 50 ml of water and adjusted to a pH value to 1.0 with concentrated hydrochloric acid, whilst ice-cooling. The solution was left standing for 16 hours in a refrigerator and the resulting precipitate was collected by filtration, washed with a small amount of water, and recrystallized from a mixture of water and acetone to give 1.66 g of the title compound. Concentration of the mother liquor yielded 2.20 g of crude crystals, which were recrystallized likewise to give a further 1.2 g of the title compound.
Nuclear Magnetic Resonance Spectrum [$(CD_3)_2SO$] δ ppm:
  4.50 [1H, singlet];
  4.57 [1H, doublet, J=6.0Hz];
  5.12 [1H, doublet, J=3.0Hz];
  5.88 [1H, doublet of doublets, J=3.0 & 6.0Hz];
  6.50 [1H, singlet];
  8.17 [1H, singlet];
  8.33 [1H, singlet].

PREPARATION 5

Dimethyl 6-desamino-6-hydroxy-4'β-chloro-5'-hydro-$O^{2'}$, $O^{7'}$-diacetylgriseolate In a two-necked flask fitted with a condenser, 4 g of dimethyl $O^{2'},O^{7'}$-diacetyl-6-desamino-6 -hydroxygriseolate (prepared as described in Preparation 3) and 40 ml of acetic acid containing 4% w/v hydrogen chloride were placed in an atmosphere of nitrogen. The mixture was heated at 80° C. for 2 hours, and then the solvent was stripped off by evaporation under reduced pressure to give a residue. The residue was dissolved in toluene and methylene chloride, which were then distilled off under reduced pressure. This process was repeated three times. The residue was purified by silica gel column chromatography using methylene chloride containing 4% v/v of methanol as an eluent, to give 2.0 g of the title compound.
Nuclear Magnetic Resonance Spectrum [$(CD_3)_2SO$] δ ppm:
  3.32 [1H, doublet, J=15.0Hz];
  3.75 [1H, doublet, J=15.0Hz];
  5.28 [1H, doublet, J=4.5Hz];
  6.00 [1H, singlet];
  6.28 [1H, doublet of doublets, J=4.5 & 5.9Hz];
  6.55 [1H, doublet, J=5.9Hz];
  8.18 [1H, singlet];
  8.47 [1H, singlet].

PREPARATION 6

Dimethyl 6-desamino-6-hydroxy-$O^{2'},O^{7'}$-diacetyl- 4'β-bromo-5'-hydrogriseolate A mixture of 500 mg of dimethyl $O^{2'},O^{7'}$-diacetyl- 6-desamino-6-hydroxygriseolate (prepared as described in Preparation 3) and 10 ml of acetic acid containing 10% w/v hydrobromic acid was placed in a sealed vessel, and dissolved by the application of ultrasonic waves for 30 minutes. The solution was then allowed to stand at room temperature for 64 hours. The solvent was distilled off under reduced pressure to give a residue, to which acetone and toluene were added and then distilled off. This process was repeated three times. A mixture of the resulting residue with 30 ml of ethyl acetate was treated with ultrasonic waves and filtered to give an insoluble material. This material was dissolved in a mixture of 30 ml of ethyl acetate and 30 ml of a 5% w/v aqueous solution of sodium bicarbonate and separated. The organic layer was washed with 20 ml of a saturated aqueous solution of sodium chloride and dried over anhydrous magnesium sulfate. The solution was evaporated under reduced pressure to give a residue which was purified by silica gel column chromatography using methylene chloride containing 3% v/v methanol as the eluent. The solvent was evaporated under reduced pressure from the main fraction, and the residue was dissolved in benzene. Lyophilization of the benzene solution afforded 60 mg of the title compound as a white powder.

Nuclear Magnetic Resonance Spectrum [(CD$_3$)$_2$SO] δ ppm:
2.98 [1H, doublet, J=15.6Hz];
3.47 [1H, doublet, J=15.6Hz];
5.35 [1H, doublet, J=4.2Hz];
5.57 [1H, singlet];
6.32 [1H, doublet of doublets, J=6.6 & 4.2Hz];
6.53 [1H, doublet, J=6.6Hz];
8.17 [1H, singlet];
8.47 [1H, singlet].

PREPARATION 7

Dimethyl 6-desamino-6-hydroxy-4'β,5'-dihydro-O$^{2'}$,O$^{7'}$-diacetylgriseolate 500 mg of dimethyl 6-desamino-6-hydroxy-4'β-chloro-5'-hydro-O$^{2'}$,O$^{7'}$-diacetylgriseolate (prepared as described in Preparation 5) and 10 mg of 2,2'-azobisisobutyronitrile were placed in a two-necked flask and dissolved in 20 ml of benzene under a nitrogen atmosphere. 3.1 ml of tributyltin hydride were added to the solution using a syringe and the mixture was stirred whilst heating under reflux for 2 hours. At the end of this time, the solvent was stripped off by evaporation under reduced pressure. The residue was dissolved in methylene chloride and purified by silica gel column chromatography, eluted with methylene chloride containing 3% v/v methanol. The main fractions were concentrated by evaporation under reduced pressure, to give 350 mg of the title compound.

Nuclear Magnetic Resonance Spectrum [CDCl$_3$+D$_2$O] δ ppm:
2.40–2.70 [2H, multiplet];
5.00 [1H, doublet, J=4.5Hz];
5.62 [1H, singlet];
5.88 [1H, doublet of doublets, J=4.5 & 7.5Hz];
6.48 [1H, doublet, J=7.5Hz];
8.13 [1H, singlet];
8.48 [1H, singlet].

PREPARATION 8

Dihydrodesoxygriseolic acid 30 litres of a medium having a pH of 7.0 before sterilization and the following composition (percentages are w/v) were prepared:
Glucose 5%
Soybean Meal 1%
Yeast Extract 0.1%
Polypeptone 0.4%
Meat Extract 0.4%
Sodium Chloride 0.25%
Calcium Carbonate 0.5%
Water to 100%

15 litres of this medium were charged into each of two 30 litre jar fermenters, which were then sterilized under pressure at 120° C. for 30 minutes. The culture medium was cooled, and then 150 ml (1% by volume) of a culture broth of *Streptomyces griseoaurantiacus* SANK 63479 (which had previously been incubated in the medium described above by means of a rotatory shaking cultivator at 28° C. for 72 hours) were inoculated into each fermenter. Cultivation was carried out at 28° C. for 96 hours under aeration at the rate of 15 litres per minute and with agitation at the rate of 200 rpm.

The two culture broths were then filtered to remove the mycelial cake and the combined filtrates (pH 7.0), in a total volume of 28 litres, were passed through a column of Diaion HP 20 (a trademark for an ion-exchange resin produced by Mitsubishi Chemical Industries Ltd.) and then adsorbed on a column of activated charcoal. This column was washed with water and then the adsorbed material was eluted with a 60:40 by volume mixture of acetone and water. The acetone was evaporated from the resulting solution under reduced pressure and the remaining aqueous solution was concentrated by evaporation under reduced pressure and then lyophilized, to give 150 mg of a crude powder.

This crude powder was dissolved in a small amount of distilled water and then adsorbed on Dowex 1×4 (Cl$^-$ form, a trademark for an ion-exchange resin produced by the Dow Chemical Company). At this stage, the product was a mixture of griseolic acid and dihydrodesoxy- griseolic acid. This mixture was subjected to gradient elution with a sodium chloride gradient to separate the two components and then the eluate was subjected to column chromatography through Sephadex LH-20 (a trademark for a product of Pharmacia Co) and the dihydrodesoxygriseolic acid was eluted with water. The fractions containing this substance were combined and their pH was adjusted to a value of 2.5 by the addition of 1N aqueous hydrochloric acid. The product was then adsorbed on a column of Diaion HP 20, washed with water and then eluted with a 60:40 by volume mixture of acetone and water. The eluate was left to stand overnight at 4° C., whereupon the dihydrodesoxygriseolic acid separated out as plates. These were separated from the liquor, giving a total of 1.87 mg of dihydrodesoxy- griseolic acid, as white plates melting at 160° C. (with decomposition, accompanied by a brown discoloration). This compound gave a single spot on silica gel thin layer chromatography (silica gel Art. 5715, a product of Merck & Co. Inc.).

We claim:

1. A compound of formula (1):

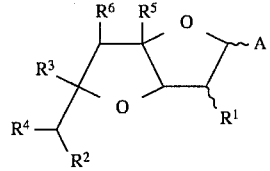

wherein
A represents a group of formula:

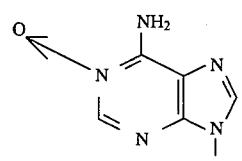

R$^1$ and R$^2$ are independently selected from the group consisting of hydrogen atoms, halogen atoms and groups of formula —OR$^9$;
R$^3$ and R$^4$ are independently selected from the group consisting of carbamoyl groups and carboxy groups;
R$^5$ and R$^6$ both represent hydrogen atoms or together they represent an extra carbon-carbon bond between the carbon atoms to which they are attached; and
R$^9$ represents a hydrogen atom, a C$_1$-C$_6$ alkyl group, an alkylsulfonyl group, a haloalkylsulfonyl group, an arylsulfonyl group or a hydroxy-protecting group;
or a pharmaceutically acceptable salt or ester thereof.

2. A compound as claimed in claim 1, wherein:

$R^1$ and $R^2$ are independently selected from the group consisting of hydrogen atoms, halogen atoms and groups of formula —$OR^{9a}$, where $R^{9a}$ represents a hydrogen atom, an alkoxycarbonyl group, an alkenyloxycarbonyl group, an aralkyloxycarbonyl group, a $C_1$-$C_{20}$ aliphatic carboxylic acyl group or a carbocyclic aromatic carboxylic acyl group.

3. A compound as claimed in claim 1, wherein:
$R^3$ and $R^4$ are independently selected from the group consisting of carboxy groups, carbamoyl groups, $C_2$-$C_5$ alkoxycarbonyl groups, (5-methyl-2-oxo-1,3-dioxolen-4-yl)methoxycarbonyl groups, phthaldyloxycarbonyl groups and $C_2$-$C_5$ alkoxycarbonyl groups having at least one substituent selected from the group consisting of aryl groups, $C_1$-$C_6$ aliphatic carboxylic acyloxy groups and $C_1$-$C_4$ alkoxycarbonyloxy groups.

4. A compound as claimed in claim 1, wherein:
$R^1$ and $R^2$ are independently selected from the group consisting of hydrogen atoms, halogen atoms, hydroxy groups, unsubstituted $C_1$-$C_4$ aliphatic acyloxy groups and aromatic acyloxy groups in which the aromatic part is a $C_6$-$C_{10}$ carbocyclic aryl group which is unsubstituted or has from 1 to 3 substituents selected from the group consisting of nitro groups, halogen atoms, $C_1$-$C_4$ alkyl groups, $C_1$-$C_4$ alkoxy groups, amino groups, hydroxy groups and cyano groups.

5. A compound as claimed in claim 4, wherein:
$R^3$ represents a carboxy group, a $C_2$-$C_5$ alkoxycarbonyl group, a (5-methyl-2-oxo-1,3-dioxolen-4-yl)methoxycarbonyl group, a phthalidyloxycarbonyl group or a $C_2$-$C_5$ alkoxycarbonyl group having 1 or 2 substituents selected from the group consisting of $C_2$-$C_5$ alkanoyloxy groups, $C_1$-$C_4$ alkoxycarbonyloxy groups and $C_6$-$C_{10}$ carbocyclic aryl groups which are unsubstituted or have from 1 to 3 substituents selected from the group consisting of nitro groups, halogen atoms, $C_1$-$C_4$ alkyl groups, $C_1$-$C_4$ alkoxy groups, amino groups, hydroxy groups and cyano groups; and
$R^4$ represents a carbamoyl group or any one of the groups defined above for $R^3$.

6. A compound as claimed in claim 1, wherein the compound is dimethyl 1'-deadenino-1'β-(2-imino-[1,2,4]-oxadiazolo-[3,2-i]purin-7-yl)griseolate hydrobromide.

* * * * *